US012605398B2

(12) United States Patent
Wang et al.

(10) Patent No.: US 12,605,398 B2
(45) Date of Patent: Apr. 21, 2026

(54) CRISPR-BASED COMPOSITIONS FOR TREATING VASCULAR DISORDERS

(71) Applicant: The Administrators of the Tulane Educational Fund, New Orleans, LA (US)

(72) Inventors: Shusheng Wang, New Orleans, LA (US); Bo Yu, New Orleans, LA (US)

(73) Assignees: The Administrators of the Tulane Educational Fund, New Orleans, LA (US); NATIONAL INSTITUTES OF HEALTH (NIH), U.S DEPT OF HEALTH AND HUMAN SERVICES (DHHS), U.S. GOVERNMENT, Bethesda, MD (US)

( * ) Notice: Subject to any disclaimer, the term of this patent is extended or adjusted under 35 U.S.C. 154(b) by 1055 days.

(21) Appl. No.: 17/425,494

(22) PCT Filed: Jan. 27, 2020

(86) PCT No.: PCT/US2020/015230
§ 371 (c)(1),
(2) Date: Jul. 23, 2021

(87) PCT Pub. No.: WO2020/159880
PCT Pub. Date: Aug. 6, 2020

(65) Prior Publication Data

US 2022/0079972 A1 Mar. 17, 2022

Related U.S. Application Data

(60) Provisional application No. 62/797,747, filed on Jan. 28, 2019.

(51) Int. Cl.
*A61K 31/7105* (2006.01)
*A61K 45/06* (2006.01)
(Continued)

(52) U.S. Cl.
CPC .......... *A61K 31/7105* (2013.01); *A61K 45/06* (2013.01); *C12N 9/22* (2013.01);
(Continued)

(58) Field of Classification Search
CPC ....... A61P 9/00; A61K 31/7105; A61K 45/06; C12N 2310/20
See application file for complete search history.

(56) References Cited

U.S. PATENT DOCUMENTS

2011/0184043 A1* 7/2011 Lagos-Quintana .......................... C12N 15/1136 435/375
2011/0196017 A1* 8/2011 Olson ....................... A61P 9/12 514/44 R (Continued)

FOREIGN PATENT DOCUMENTS

WO 2011011061 A2 1/2011
WO 2014152432 A2 9/2014

OTHER PUBLICATIONS

Gilbert et al., vol. 154, Issue 2, Jul. 18, 2013, pp. 442-451 (Year: 2013).*

(Continued)

*Primary Examiner* — Ram R Shukla
*Assistant Examiner* — Shabana S Meyering
(74) *Attorney, Agent, or Firm* — DENTONS DAVIS BROWN PC; Matthew Coryell

(57) ABSTRACT

CRISPR-based compositions and methods of their use to impair or promote angiogenesis in a patient to treat indications including, but not limited to, tumor growth, age-related macular degeneration, and metastasis. Single-guide ribonucleic acids sg-RNA-1 (SEQ ID NO: 2) or sg-RNA-2 (SEQ ID NO: 3) are shown to affect angiogenesis.

3 Claims, 44 Drawing Sheets

Specification includes a Sequence Listing.

(51) Int. Cl.
*C12N 9/22* (2006.01)
*C12N 15/11* (2006.01)
*C12N 15/86* (2006.01)

(52) U.S. Cl.
CPC ............ *C12N 15/111* (2013.01); *C12N 15/86* (2013.01); *C12N 2310/20* (2017.05)

(56) References Cited

U.S. PATENT DOCUMENTS

2016/0201089 A1 7/2016 Gersbach et al.
2017/0275619 A1* 9/2017 Wang .................. A61K 31/713
2018/0237771 A1 8/2018 Kim et al.

OTHER PUBLICATIONS

Li et al., Biomaterials. Jul. 2018 ; 171: 207-218. doi: 10.1016 (Year: 2018).*
Jinek et al., Science. Jun. 28, 2012;337(6096):816-821 (Year: 2012).*
Zhou Q et al., Elife. Feb. 11, 2019;8:e40470 (Year: 2019).*
Derrien, T .; Johnson, R; Bussotti, G.; Tanzer, A.; Djebali, S.; Tilgner, H.; Guernec, G.; Martin, D.; Merkel, A.; Knowles, D. G.; Lagarde, J.; Veeravalli, L.; Ruan.; X.; Ruan, Y.; Lassman, T.; Carnici, P.; Brown, J. B.; Liovich, L.; Gonzalez, J. M.; Thomas, M,; Davis, C. A.; Shiekhattar, R.; Gingerad, T. R.; Hubbard, T. J.; Notredame, C.; Harrow, J.; Guigo, R. "The GENCODE v7 catalog of human long noncoding RNAs: Analysis of their gene structure, evolution, and expression." Genome Research 22, 1775-1789 (2012).
Harris, T. A.; Yamakuchi, M.; Ferlito, M.; Mendell, J. T.; Lowenstein, C. J. "MicroRNA-126 regulates endothelial expression of vascular cell adhesion molecule 1." Proc Natl Acad Sci 105. 1516-1521, (2008).
Mattes, J.; Collison, A.; Plank, M.; Phipps, S.; Foster, P. S. Antagonism of microRNA-126 suppresses the effector function of TH2 cells and the development of allergic airways disease. Proc Natl Acad Sci 106, 18704-18709 (2009).
Agudo, J.; Ruzo, A.; Tung, N.; Salmon, H.; Leboeuf, M.; Hashimoto, D.; Becker, C.; Garrett-Sinha, L-A.; Baccarini, A.; Merad, M.; Brown, B. D. "The miR-126-VEGFR2 axis controls the innate response to pathogen-associated nucleic acids." Nat Immunol 15, 54-62 (2014).
Zhou, Q.; Anderson, C.; Hanus, J.; Zhao, F.; Ma, J.; Yoshiura, A.; Wang, S. "Strand and Cell Type-specific Function of microRNA-126 in Angiogenesis." Mol Ther 24, 1823-1835, (2016).
Amati, B.; Land, H. "Myc-Max-Mad: a transcription factor network controlling cell cycle progression, differentiation and death." Curr Opin Genet Dev 4, 102-108 (1994).
Jager, R. D.; Mieler, W. F.; Miller, J. W. "Age-related macular degeneration." The New England Journal of Medicine 358, 2606-2617, (2008).
Folk, J. C.; Stone, E. M. "Ranibizumab therapy for neovascular age-related macular degeneration." The New England Journal of Medicine 363, 1648-1655, (2010).
Falk, M. K.; Kemp, H.; Sorensen, T. L. "Four-year treatment results of neovascular age-related macular degeneration with Ranibizumab and causes for discontinuation of treatment." American Journal of Ophthalmology, 155, 7, 89-95 (2013).
Skovseth, D. K.; Kuchler, A. M.; Haraldsen, G. "The HUVEC/Matrigel assay: an in vivo assay of human angiogenesis suitable for drug validation." Methods Mol Biol 360, 253-268, (2007).
Zhou, Q.; Anderson, C.; Zhang, H.; Li, X.; Inglis, F.; Jayagopal, A.; Wang, S. "Repression of choroidal neovascularization through actin cytoskeleton pathways by microR NA-24." Mol Ther 22, 378-389, (2014).
Wang, S.; Li, X.; Parra, M.; Verdin, E.; Bassel-Duby, R.; Olson, E. N. "Control of endothelial cell proliferation and migration by VEGF signaling to histone deacetylase 7." Proc Natl Acad Sci 105, 7738-7743, (2008).
Wagatsuma, A.; Sadamoto, H.; Kitahashi, T.; Lukowiak, K.; Urano, A.; Ito, E. "Determination of the exact copy numbers of particular mRNAs in a single cell by quantitative real-time RT-PCR." J Exp Biol 208. 2389-2398 (2005).
Nelson, J. D.; Denisenko, O.; Bomsztvk, K. "Protocol for the fast chromatin immunoprecipitation (Chip) method." Nature Protocols, 1, 179-185 (2006).
Larson, M. H.; Gilbert, L. A.; Wang, X.; Lim, W. A.; Weissman, J. S., Qi, L. S. "Crispr interference (CRISPRi) for sequence-specific control of gene expression." Nat Protoc., 8, 2180-2196, (2013).
Huang, Z. P.; Pu, W. T.; Wang, D-Z. "Cardiomyocyte-enriched protein CIP protects against pathophysiological stresses and regulates cardiac homeostasis." The Journal of Clinical Investigation, 125, 4122-4134 (2015).
Goyal, A.; Myacheva, K.; Grob, M.; Klingenberg, M.; Arque, B. D.; Diederichs, S. "Challenges of CRISPR/Cas9 applications for long non-coding RNA genes." Nucleic Acids Research, vol. 45, No. 3, e12 (2017).
Hong, G.; Kuek, V.; Shi, J.; Zhou, L.; Han, X.; He, W.; Tickner, J.; Qiu, H.; Wei, Q.; Xu, J. "EGFL7: Master regulator of cancer pathogenesis, angiogenesis and an emerging mediator of bone homeostasis." J. Cell Physiol, 233, 8526-8537 (2018).
Liu, Y.; Chen, Z.; He, A.; Zhan, Y.; Li, J.; Liu, L.; Wu, H.; Zhuang, C.; Lin, J.; Zhang, Q.; Huang, W. "Targeting cellular mRNAs translation by CRISPR-Cas9" Scientific Reports, 6, 29652 (2016).
Zhou, Q.; Yu, B.; Anderson, C.; Huang, Z-P.; Hanus, J.; Zhang, W.; Han, Y.; Bhattacharjee, P. S.; Srinivasab, S.; Zhang, K.; Wang, D-Z.; Wang, S. "LncEGF7OS regulated human angiogenesis by interacting with MAX at the EGFL7/miR-126 locus" eLIFE, 8, e40470 (2019).
Wang, S.; Zhou, Q.; Ma, J.; Yu, B. Paper presented at the 2018 Annual Meeting of the Association for Research in Vision and Ophthalmology, ARVO (2018) (Abstract).
Carmeliet, P. Angiogenesis in health and disease. Nature Medicine, 9, 653-660(2003).
Roura, S.; Planas, F.; Prat-Vidal, C.; Leta, R.; Soler-Botija, Carreras, F.; Llach, A.; Hove-Madsen, L.; Llado, G. P.; Farre, J.; Cinca, J.; Bayes-Genis, A. "Indiopathic dilated cardiomyopathy exhibits defects vascularization and vessel formation." European Journal of Heart Failure, 9, 995-1002 (2007).
Gavin, .J B .; Maxwell, L; Edgar, S. G. "Microvascular involvement in cardiac pathology." (1998) J Mol Cell Cardiol 30, 2531-2540. do: 10.1006/mcc.1998.0824 (1998).
De Boer, R. A.; Pinto, Y. M.; Van Veldhuisen, D. .J. "The imbalance between oxygen demand and supply as a potential mechanism in the pathophysiology of heart failure: The role of microvascular growth and abnormalities." Microcirculation 10, 113-126 (2003).
Yla-Herttuala, S.; Bridges, C.; Katz, M. G.; Korpisalo, P. "Angiogenic gene therapy in cardiovascular diseases: dream or vision?" European Heart Journal 38, 1365-1371 (2017).
Brown, D. M.; Kaiser, P. K.; Michels, M.; Soubrane, G.; Heier, J. S.; Kim, R. Y.; Sy, J. P.; Scheider, S. "Ranibizumab versus verteporfin for neovascular age-related macular degeneration." The New England Journal of Medicine, 355, 1432-1444 (2006).
Rosenfeld, P. .J; Brown, D. M.; Heier, J. S.; Boyer, D. S.; Kaiser, P. K.; Chung, C. Y. Kim, R. Y. "Ranibizumab for neovascular age-related macular degeneration." The New England Journal of Medicine, 355, 1419-1431 (2006).
Zampros, I.; Praidu, A.; Braitikos, P.; Ekonomidis, P.; Androudi, S. "Antivascular endothelial growth factor agents for neovascular age-related macular degeneration." J Ophthalmol. vol. 2012, Article: 319728 (2012).
Hurwitz, H.; Fehrenbacher, L.; Novotny, W.; Cartwright, T.; Hainsworth, J; Heim, W.; Berlin, J.; Baron, A.; Griffing, S.; Holmgren, E.; Ferrara, N.; Fyfe, G.; Rogers, B.; Ross, R.; Kabbinavar, F. "Bevacizubmab plus irinotecan, fluorouracil, and leucovorin for metastatic colorectal cancer." The New England Journal of Medicine, 350, 2335-2342 (2004).
Miller, K.; Wang, M.; Gralow, J.; Dickler, M.; Cobleigh, M.; Perez, E. A.; Shenkier T.; Cella, D.; Davidson, N. E. "Paclitaxel plus bevacizumab versus paclitaxel alone for metastatic breast cancer." The New England Journal of Medicine 357, 2667-2676, (2007).

(56) References Cited

OTHER PUBLICATIONS

Sandler, A.; Gray, R.; Perry, M. C.; Brahmer, J.; Schiller, J. H.; Dowlati, A.; Lilenbaum, R.; Johnson, D. H. "Paclitaxel-carboplatin alone or with bevacizumab for non-small-cell lung cancer." The New England Journal of Medicine, 355, 2542-2550 (2006).

Shojaei, F.; Napoleone, F. "Antiangiogenic therapy for cancer: an update." Cancer Journal 13, 345-348 (2007).

Kapranov, P.; Willingham, A. T.; Gingreras, T. R. "Genome-wide transcription and the implications for genomic organization." Nature Reviews Genetics 8, 413-423, (2007).

Gerstein, M. "Encode leads the way on big data." Nature 489, 208-208 (2012).

Ecker, J. R.; Bickmore, W. A.; Barroso, I.; Pritchard, J. K.; Gilad, Y.; Segal, E. "ENCODE explained." Nature 489, 52-53 (2012).

Wang, S.; Olsen, E. N. "AngiomiRS—key regulators of angiogenesis." Curr Opin Genet Dev 19, 205-211 (2009).

Ulitsky, I.; Bartel, D. P. "lincRNAs: genomics, evolution, and mechanisms." Cell 154. 26-46 (2013).

Yu, B.; Wang, S. "Angio-LncRs: LncRNAs that regulate angiogenesis and vascular disease." Theranosctics, 8, 3654-3675 (2018).

Kumar, M. M.; Goyal, R.; "lncRNA as a Therapeutic Target for Angiogenesis." Current Topics in Medicinal Chemistry, 17, 1750-1757 (2016).

Michalik, K. M.; You, X.; Manavski, Y.; Doddaballapur, A.; Zornig, M.; Braun, T.; John, D.; Ponomareva, Y.; Chen, W.; Uchida, S.; Boon, R. A.; Dimmerler, S. "Long noncoding RNA MALAT1 regulates endothelial cell function and vessel growth." Circ Reg 114, 1389-1397, (2014).

Liu, J-Y.; Yao, J.; Li, X-M.; Song, Y-C.; Wang, X-Q.; Li, Y-J, Yan, B.; Jiang, Q. "Pathogenic role of lncRNA-MALAT1 in endothelial cell dysfunction in diabetes mellitus." Cell death and disease, 5, e1506 (2014).

Leisegang, M. S.; Fork, C.; Josipovic, T.; Richter, F. M.; Preussner, J.; Hu, J.; Miller, M. J.; Epah, J.; Hofmann, P.; Gunther, S.; Moll, F.; Valasarajan, C.; Heidler, J.; Ponomareva, Y.; Freiman, T. M.; Maegdefessel, L. ; Plate, K. H.; Mittelbronn, M.; Uchida, S.; Kunne, C.; Stellos, K.; Shermurly, R. T.; Weissmann, N.; Devraj, K.; Wittig, I.; Boon, R. A.; Simmeler, S.; Pullamsetti, S. S.; Looso, M.; Miller< F. J., Brandes, R, P. "Long Noncoding Rna Mantis Facilitates Endothelial Angiogenic Function." Circulation, Jul. 4, 2017;136(1) :65-79.

Kurian, L.; Aguirre, A.; Sancho-Martinez, I.; . L. et al. Identification of novel long noncoding RNAs underlying vertebrate cardiovascular d e v e l o p m e n t . Circulation 131. 1278-1290. do: 10.1161/CIRCULATIONAHA.114.013303 (2015).

He, C.; Yang, W.; Yang, J.; Ding, J.; Li, S.; Wu, W.; Zhou, F.; Jiang, Y.; Teng, L.; Yang, J. "Long noncoding RNA MEG3 negatively regulates proliferation and angiogenesis in vascular endothelial cells." DNA and Cell Biology 36, 475-481, (2017).

Qiu, G-Z.; Tian, W.; Fu, H-T.; Li, C-P, Li, B. "Long noncoding RNA-MEG3 is involved in diabetes mellitus-related microvascular dysfunction." Biochemical and Biophysical Research Communications 471, 135-141, (2016).

Yan, B.; Yao, J.; Liu, J-Y.; Li, X-M.; Wang, X-Q.; Li, Y-J.; Tao, Z-F.; B. A et al. lncRNA-MIAT Regulates Microvascular Dysfunction by Functioning as a Competing Endogenous RNA. Circulation Research 116, 1143-1144 (2015).

Boulberdaa, M.; Scott, E.; Ballantyne, M,; Garcia, R.; Descamps, B.; Angelini, G. D.; Brittan, M.; Hunter, A.; Mcbride, M.; Mcclure, J.; Miano, J.M.; Emanueli, C.; Mills, M. N.; Mountford, J. C.; Baker, A. H. "A role for the long noncoding RNA SENCR in commitment and function of endothelial cells." American Society of Gene and Cell Therapy, vol. 24, 5, 978-990 (2016).

Neumann, P.; Jae, N.; Knau, A.; Glaser, S. F.; Fouani, Y.; Rossbach, O.; Kruger, M.; John, D.; Bindereif, A.; Grote, P.; Boon, R. A.; Dimmeler, S. "The lncRNA GATA6-AS epigenetically regulates endothelial gene expression via interaction with LOXL2." Nature Communications, 9, 237 (2018).

Man, H. S. .J; Sukumar, A. N.; Lam, G. C.; Turgeon, P. J.; Yan, M. S.; Ku, K. H.; Dubinsky, M. K.; Ho, D. J. J.; Wang, J. J.; Das, S.; Mitchell, N.; Oettgen, P.; Sefton, M. V.; Marsden, P. A. "Angiogenic patterning by STEEL, an endothelial-enriched long noncoding RNA." Proc Natl Acad Sci, 115, 10, 2401-2406 (2018).

Orom, U. A.; Derrien, T.; Beringer, M.; Gumireddy, K.; Gardini, A.; Bussotti, G.; Lai, F.; Zytnicki, M.; Notredame, C.; Huang, Q.; Guigo, R.; Shiekhattar, R. "Long noncoding RNAs with enhancer-like function in human cells." Cell 143, 46-58 (2010).

Bell, R. D.; Long, X.; Lin, M.; Bergmann, J. H.; Nanda, V.; Cowan, S. L.; Zhou, Q.; Han, Y.; Spector, D. L.; Zheng, D.; Miano, J. M. "Identification and initial functional characterization of a human vascular cell enriched long noncoding RNA." Arterioscler Thromb Vasc Biol 34(6), 1249-1259 (2014).

Diehn, M.; Sherlock, G.; Binkley, G.; Jin, H.; Matese, J. C.; Hernandez-Broussard, T.; Rees, C. A.; Cherry, J. M.; Bolstein, D.; Brown, P. O.; Alizadeh, A. A.; "SOURCE: a unified genomic resource of functional annotations, ontologies, and gene expression data." Nucleic Acids Res 31, 219-223 (2003).

Fish, J. E.; Santoro, M. M.; Morton, S. U.; Yu, S.; Yeh, R-F.; Wythe, J. D.; Bruneau, B. G.; Stainier, D. Y. R.; Srivastava, D. "miR-126 regulates angiogenic signaling and vascular integrity." Dev Cell 15, 272-284 (2008).

Wang, S.; Aurora, A. B.; Johnson, B. A.; Qi, X.; Mcanally, J.; Hill, J. A.; Richardson, J. A.; Bassel-Duby, R.; Olson, E. N. "The endothelial-specific microRNA miR-126 governs vascular integrity and angiogenesis." Dev cell 15, 261-271 (2008).

Kuhnert, F.; Mancuso, M. R.; Hampton, J.; Stanjunas, K.; Asano, T.; Chen, C-Z.; Kuo, C. J. "Attribution of vascular phenotypes of the murine Bgfl7 locus to the microRNA miR-126." Development 135, 3989-3993 (2008).

Durrans, A.; Stuhlmann, H. "A role for Egfl7 during endothelial organization in the embroid body model system." J Angiogenes Res 2, 4, 12 pages (2010).

Parker, L. H.; Schmidt, M.; Jin, S-W.; Gray, A. M.; Beis, D.; Pham, T.; Frantz, G.; Palmieri, S.; Hillan, K.; Stainier, D. Y. R.; De Sauvage, F. J.; Ye, W. L. "The endothelial-cell-derived secreted factor Egfl7 regulates vascular tube formation." Nature 428, 754-758 (2004).

Schmidt, M.; Paes, K.; Maziere, A. D.; Smyczek, T.; YaNG, S.; Gray, A.; French, D.; Kasman< I.; Klumperman, J.; Rice, D. S.; Ye, W. "EGFL7 regulates the collective migration of endothelial cells by restricting their spatial distribution." Development 134, 2913-2923 (2007).

Zhang, Q.; Chen, C. Y.; Yedavalli, V. S.; Jeang K. T. "Neati long noncoding RNA and paraspeckle bodies modulate HIV-1 post-transcriptional expression." MBio 4, e00596-00512 (2013).

Cabili, M. N.; Dunagin, M. C.; Mcclanahan, P. D.; Biaesch, A.; Padovan-Merhar, O.; Regev, A.; Rinn, J. L.; Raj, A. "Localization and abundance analysis of human lncRNAs at single-cell and single-molecule resolution." Genome Biol 16, 20, (2015).

Antequera, F. "Structure, function and evolution of CpG island promoters." Cell Mol Life Sci 60, 1647-1658, (2003).

Uesaka, M.; Nishimura, O.; Go, Y.; Nakashima, K.; Agata, K.; Imamura, T. "Bidirectional promoters are the major source of gene activation-associated non-coding RNAs in mammals." BMC Genomics 15, 35, (2014).

Harris, T. A.; Yamakuchi, M.; Kondo, M.; Oettgen, P.; Lowenstein, C. J. Harris, T.J "Ets-1 and Ets-2 regulate the expression of microRNA-126 in endothelial cells." Arterioscler Thromb Vasc Biol 30, 1990-1997 (2010).

Hetheridge, C.; Mavria, G.; Mellor, H. "Uses of the in vitro endothelial-fibroblast organotypic co-culture assay in angiogenesis research." Biochem So Trans 39, 1597-1600, (2011).

Shao, Z.; Friedlander, M.; Hurst, C. G.; Cui, Z.; Pei, D. T.; Evans, L. P.; Juan, A. M. ; Tahir, H.; Duhamel, F.; Chen, J.; Sapieha, P.; Chemtob, S.; Joyal, J-S.; Smith, L. E. H. "Choroid sprouting assay: an ex vivo model of microvascular angiogenesis." PLoS One 8, e69552, (2013).

Bellucci, M.; Agostini, F.; Masin, M.; Tartaglia, G. G. "Predicting protein associations with long noncoding RNAs." Nat Methods 8, 444-445 (2011).

Vervoorts, J.; Luscher-Firzlaff, J. M.; Rottmann, S.; Lilischkis, R.; Walsemann< G.; Dohmann, K.; Austen, M.; Luscher, B. "Stimula-

(56) References Cited

OTHER PUBLICATIONS tion of c-MYC transcriptional activity and acetylation by recrument of the cofactor CBP." EMBO Ken 484-490 (2003).
Mai, S.; Jalava, A. "C-Myc binds to 5' flanking sequence motifs of the dihydrofolate reductase gene in cellular extracts: role in proliferation." Nucleic Acids Res 22, 2264-2273 (1994).
Bouchard, C.; Dittrich, O.; Kiermaier, A.; Dohmann, K.; Menkel, A.; Eilers, M.; Luscher, B. "Regulation of cyclin D2 gene expression by the Myc/Max/Mad network: Myc-dependent T R A P recruitment and histone acetylation at the cyclin D2 promoter." Genes Dev 15, 2042-2047, (2001).
Qi, L. S.; Larson, M. H.; Gilbert, L. A.; Doudna,, J. A.; Weissman< J. S.; Arkin, A. P.; Lim, W. A. "Repurposing CRISPR as an RNA-guided platform for sequence-specific control of gene expression." Cell, 152 (5), 1173-1183 (2013).

* cited by examiner

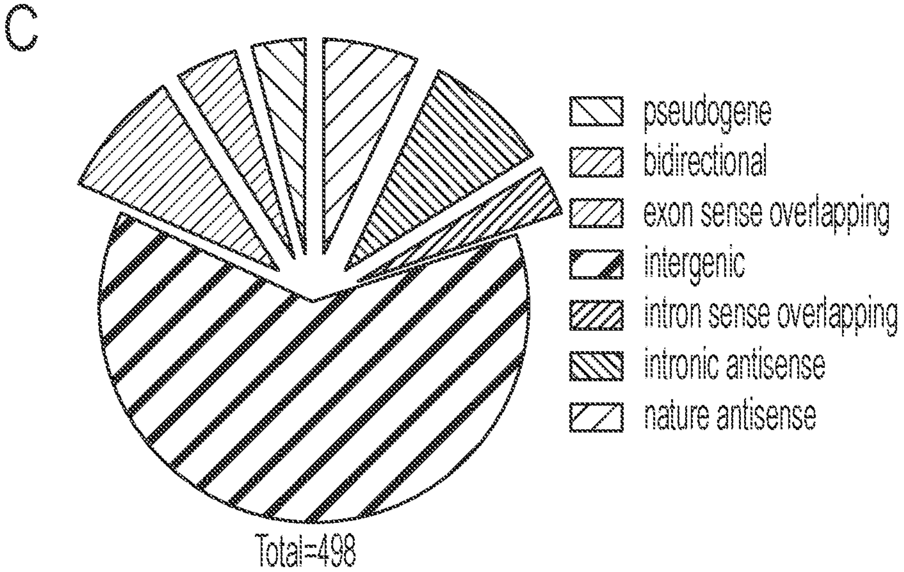
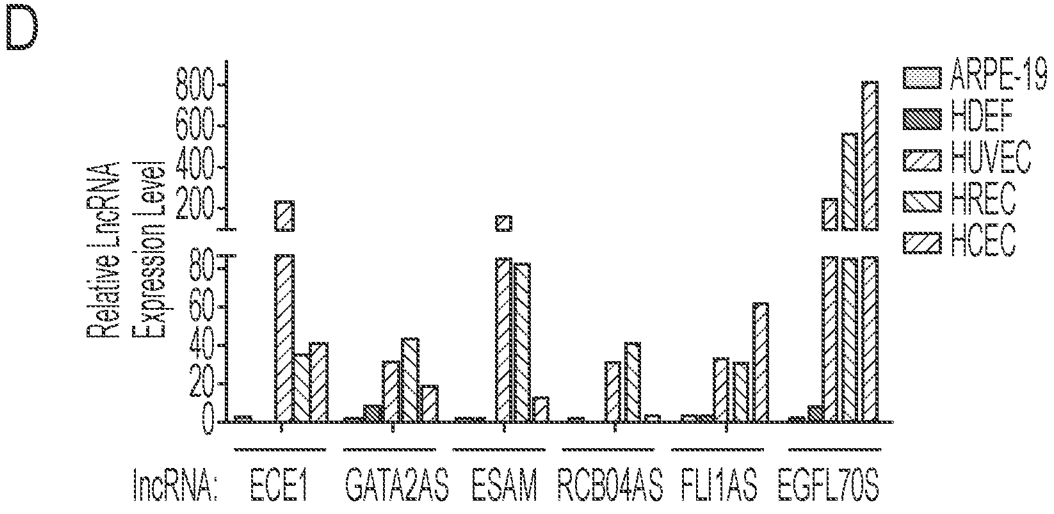
FIGS. 1C-D

A

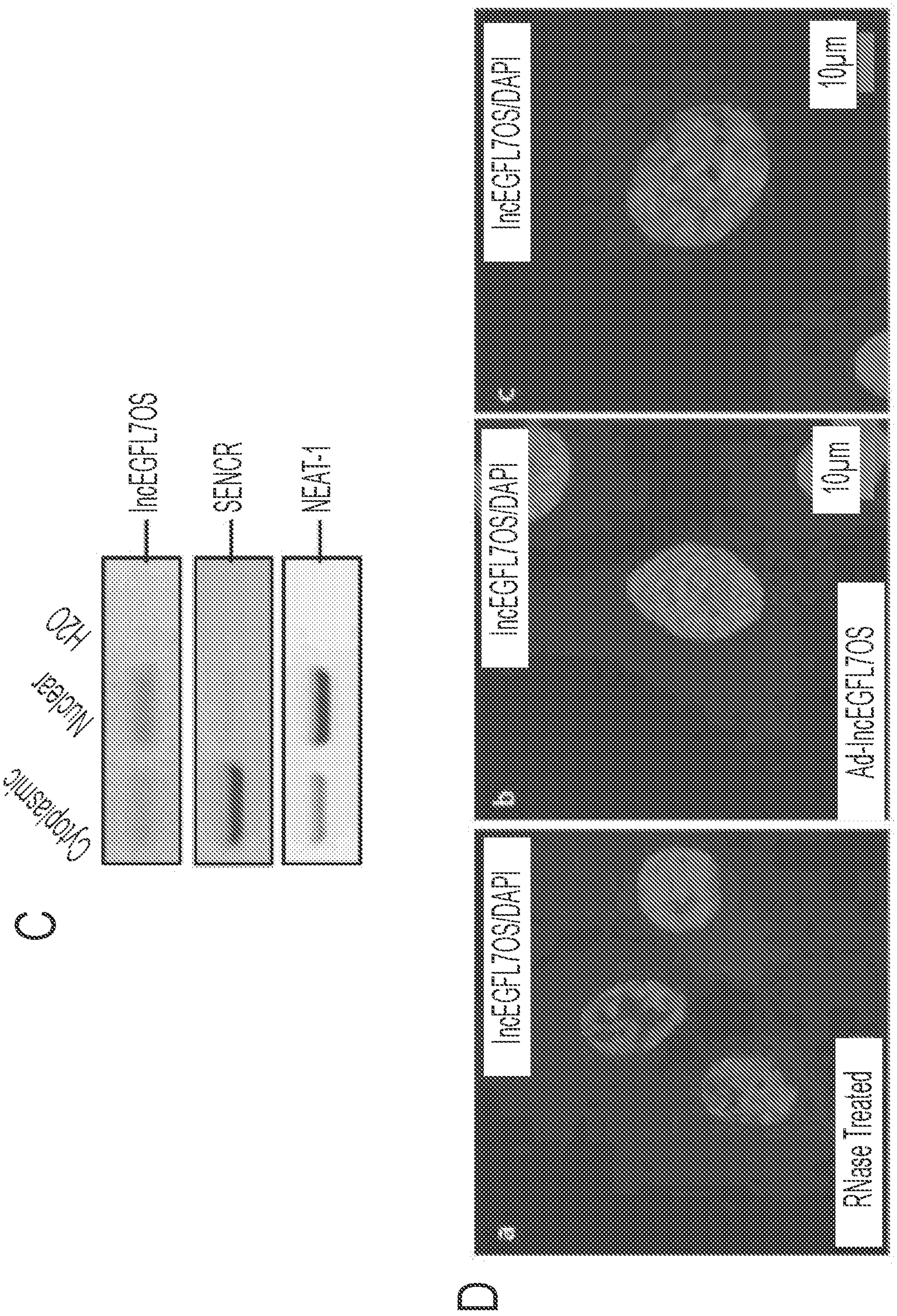
FIGS. 2C-D

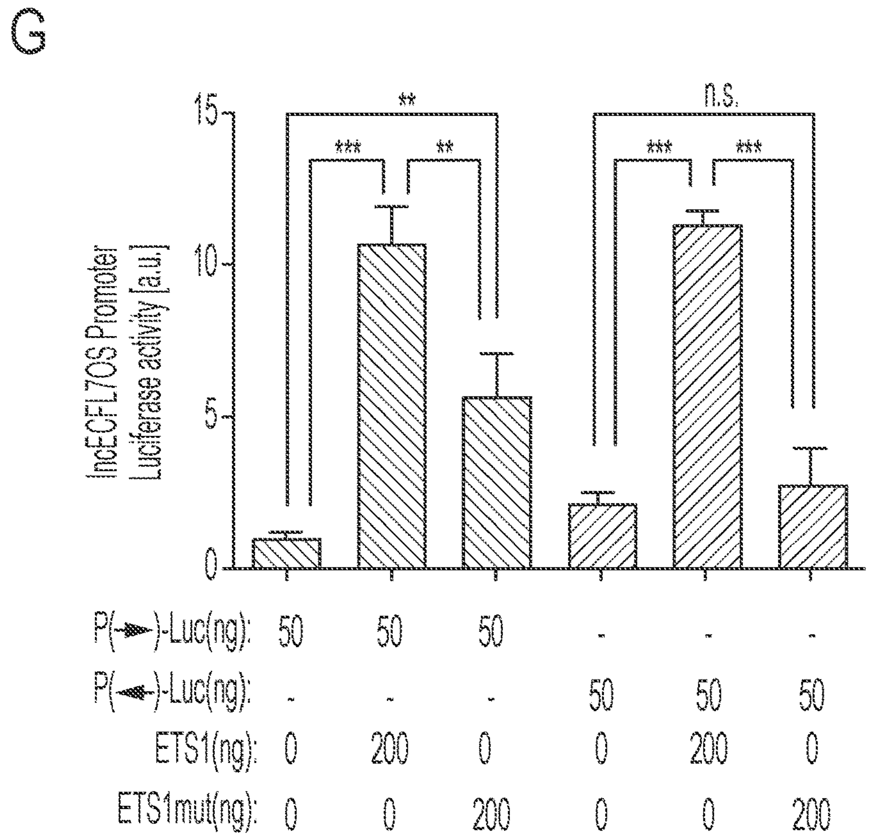
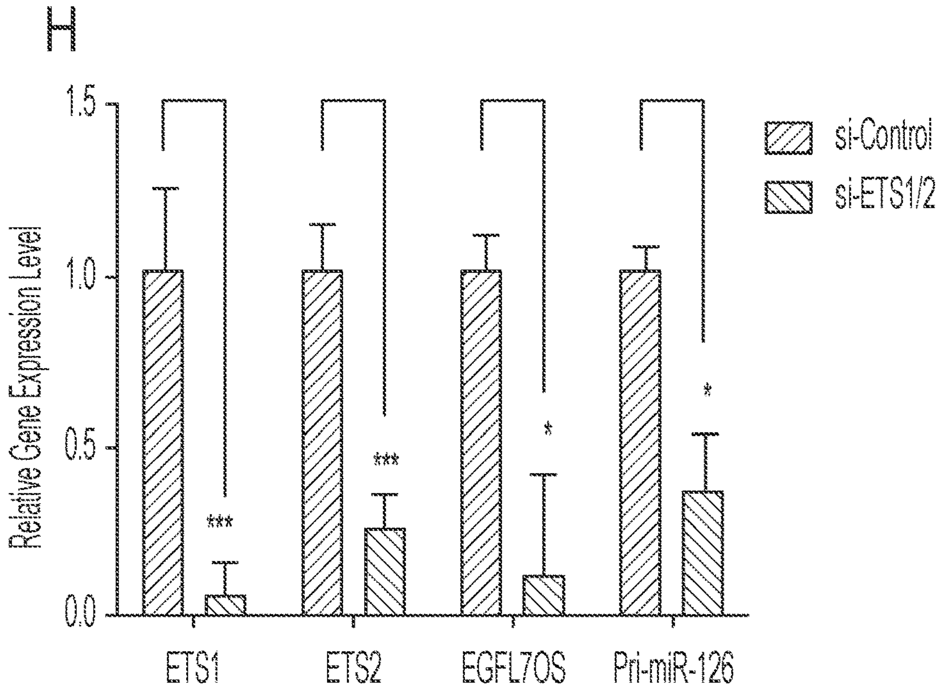
FIGS. 2G-H

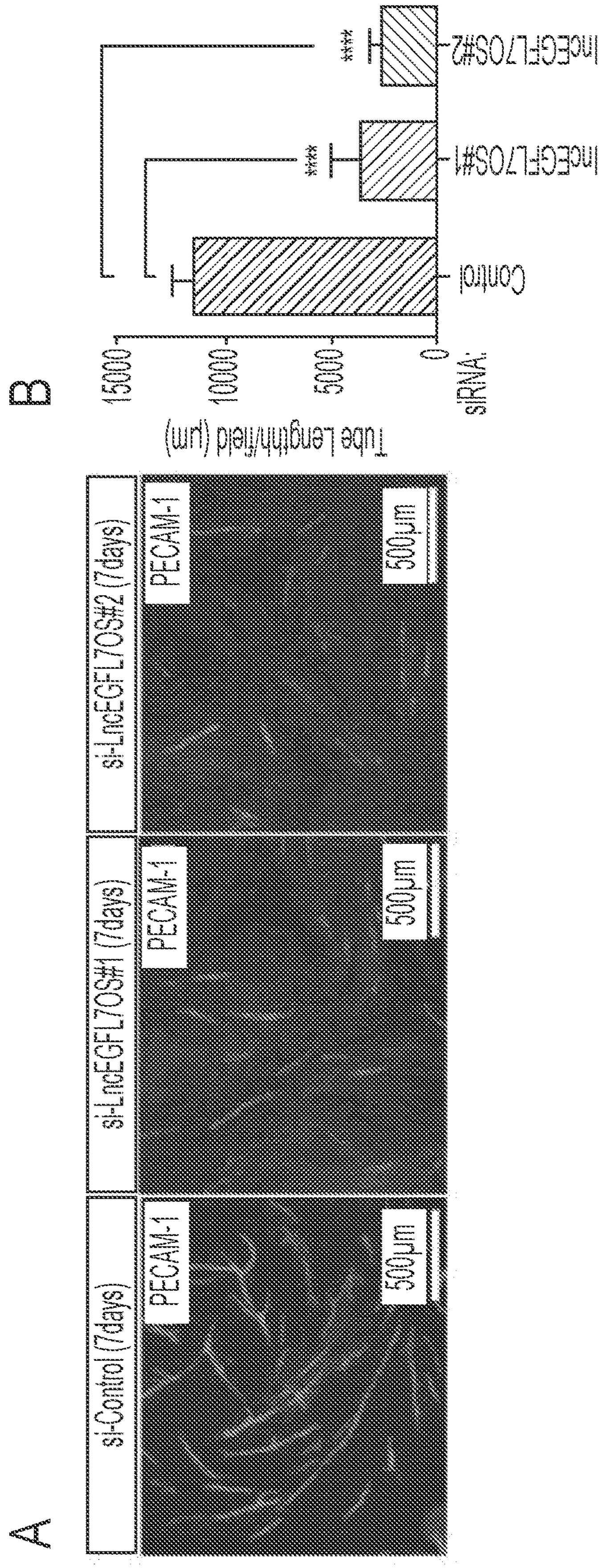
FIGS. 3A-B

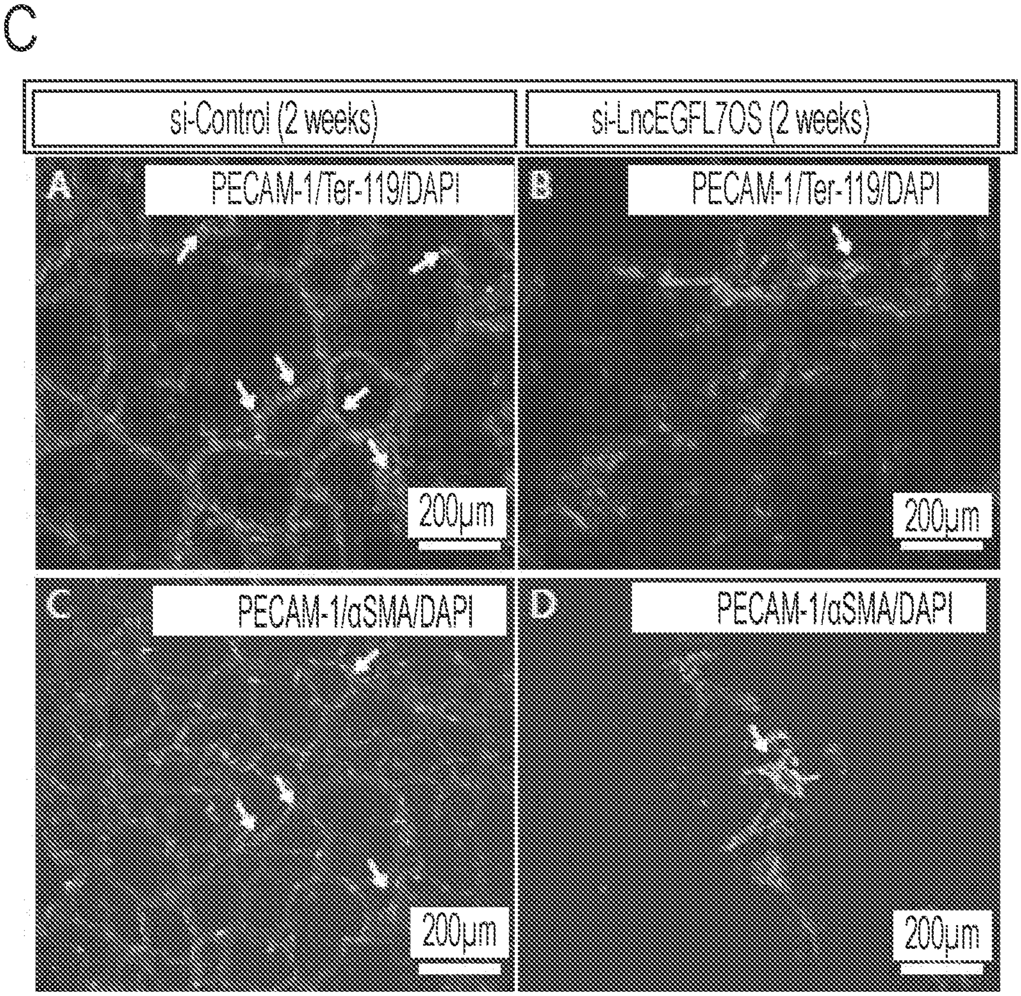
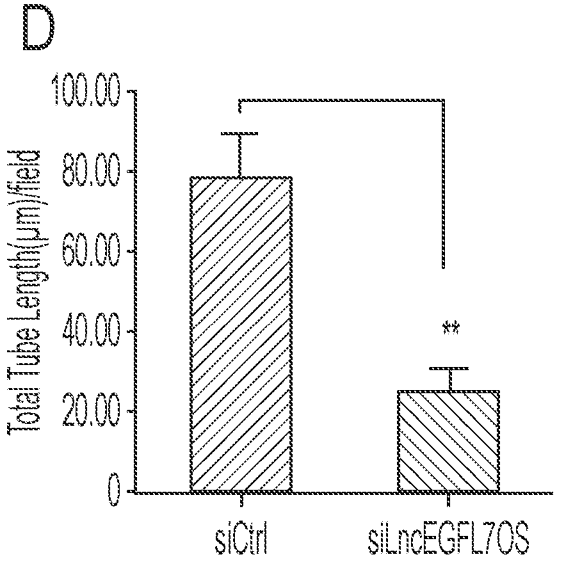
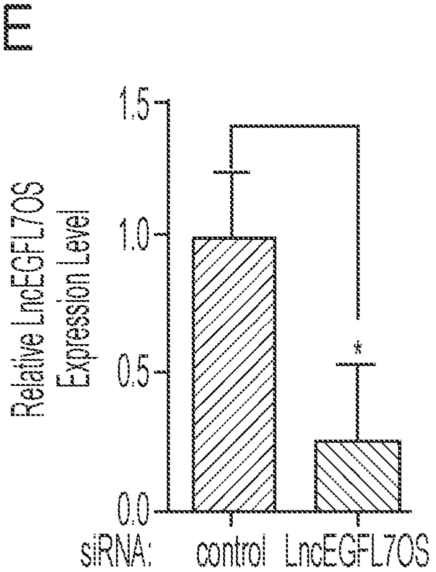
FIGS. 3C-E

F
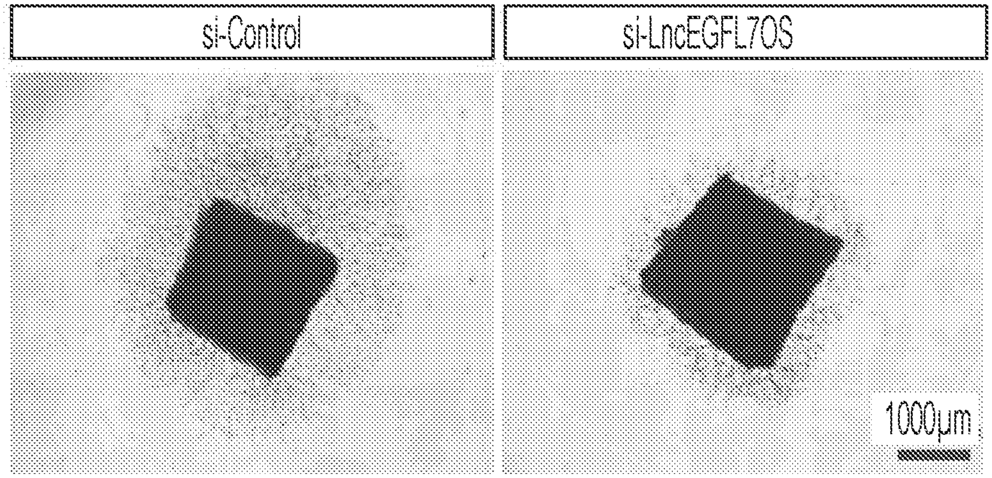
G
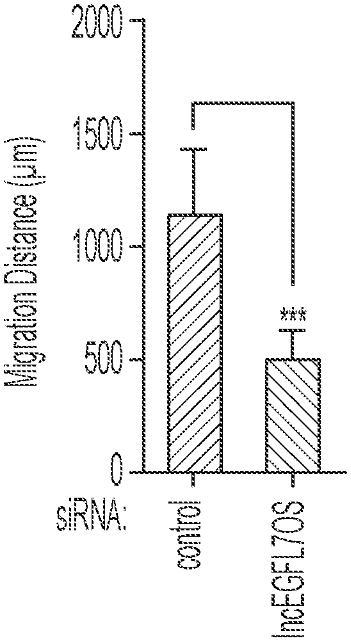
FIGS. 3F-G

H

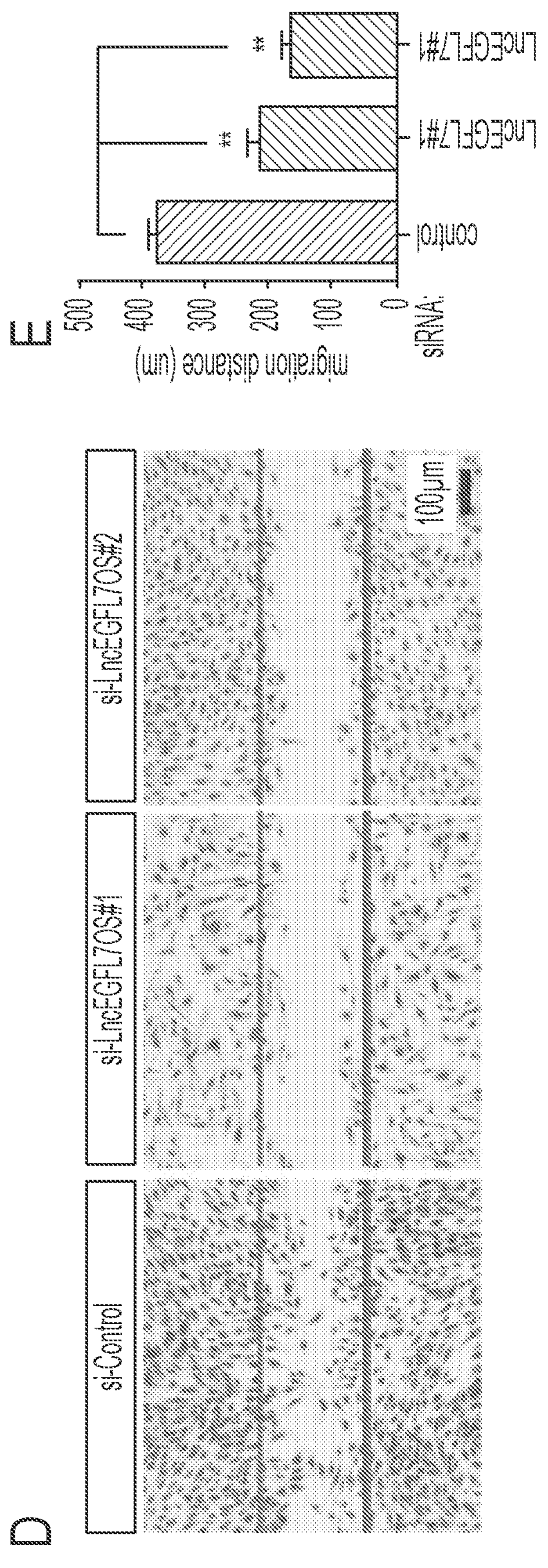
FIGS. 4D-E

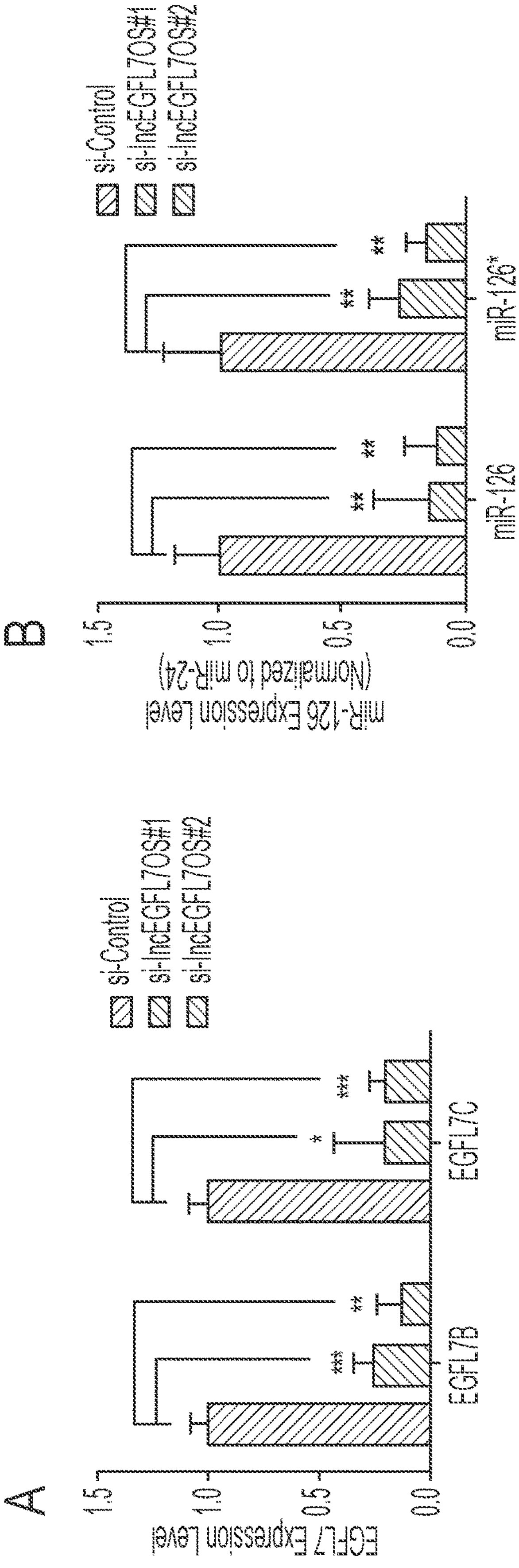
FIGS. 5A-B

C

| | | | | | | |
|---|---|---|---|---|---|---|
| Control siRNA: | + | - | - | + | - | - |
| si-lncEGFL7OS#1: | - | + | - | - | + | - |
| si-lncEGFL7OS#2: | - | - | + | - | - | + |
| VEGF-A: | - | - | - | + | + | + |

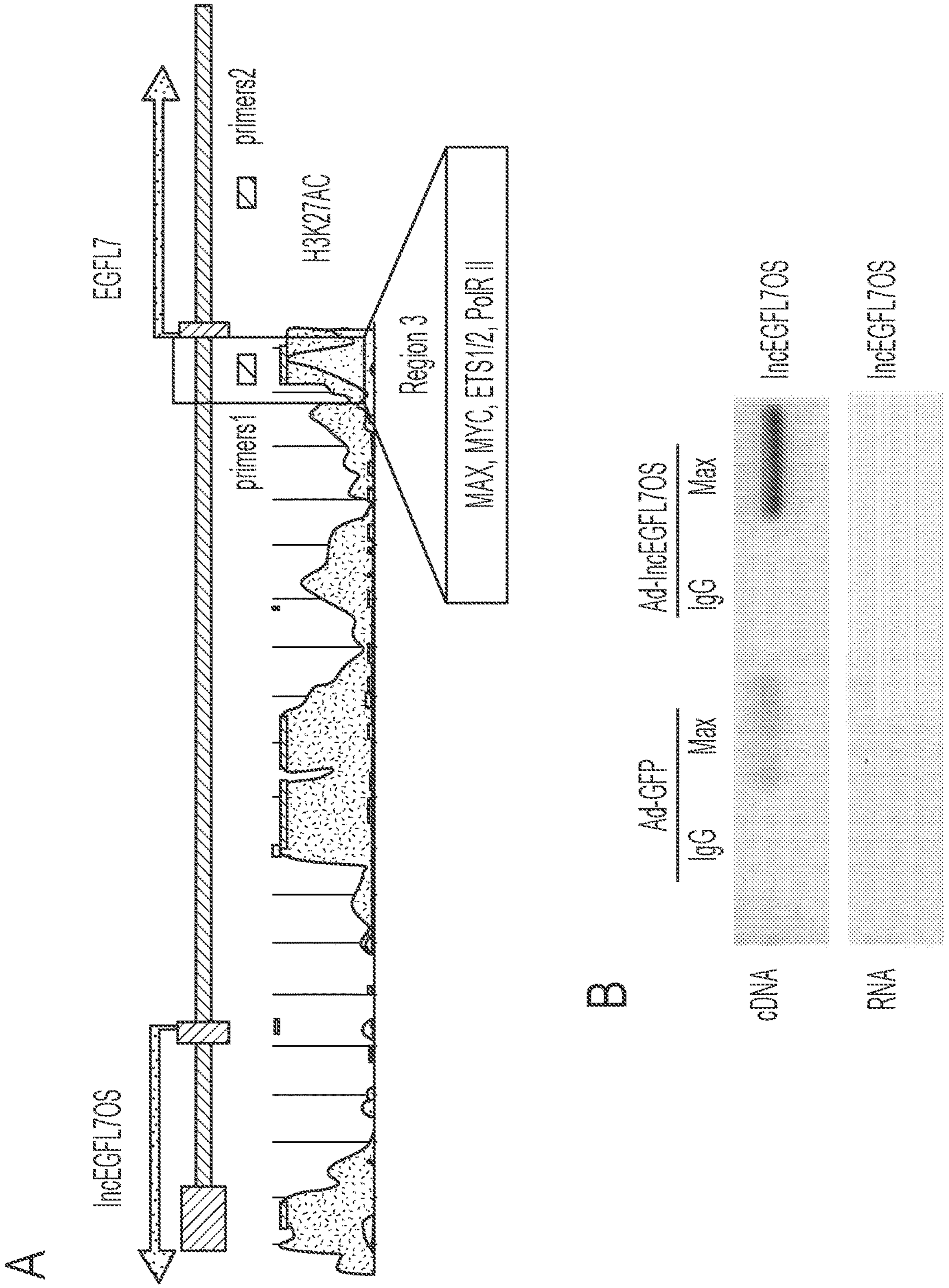
FIGS. 6A-B

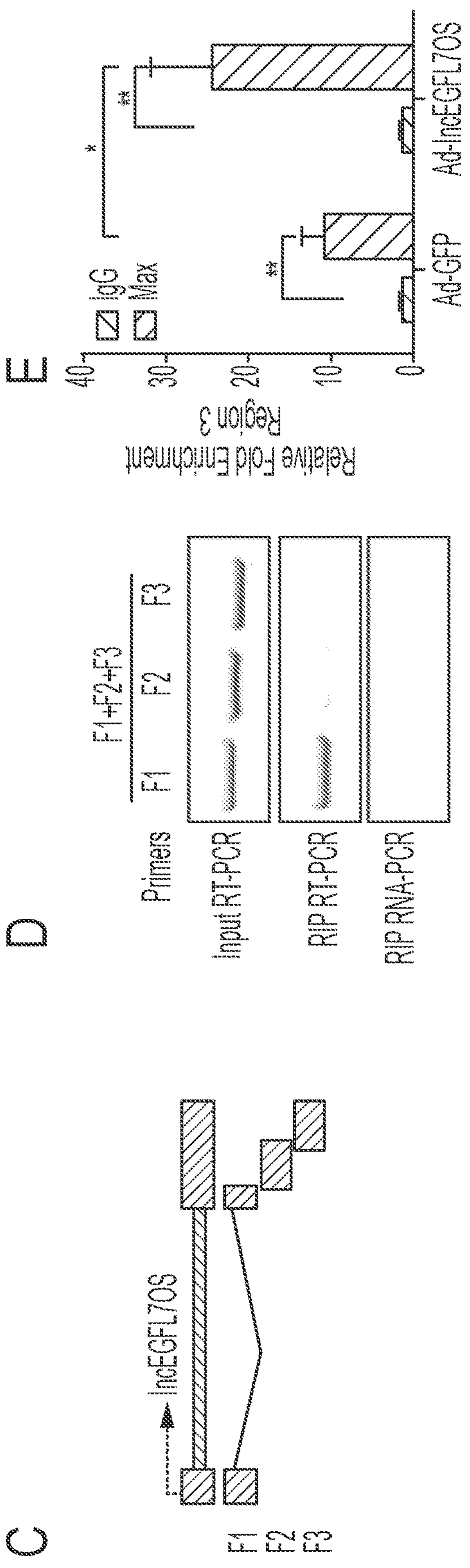
FIGS. 6C-E

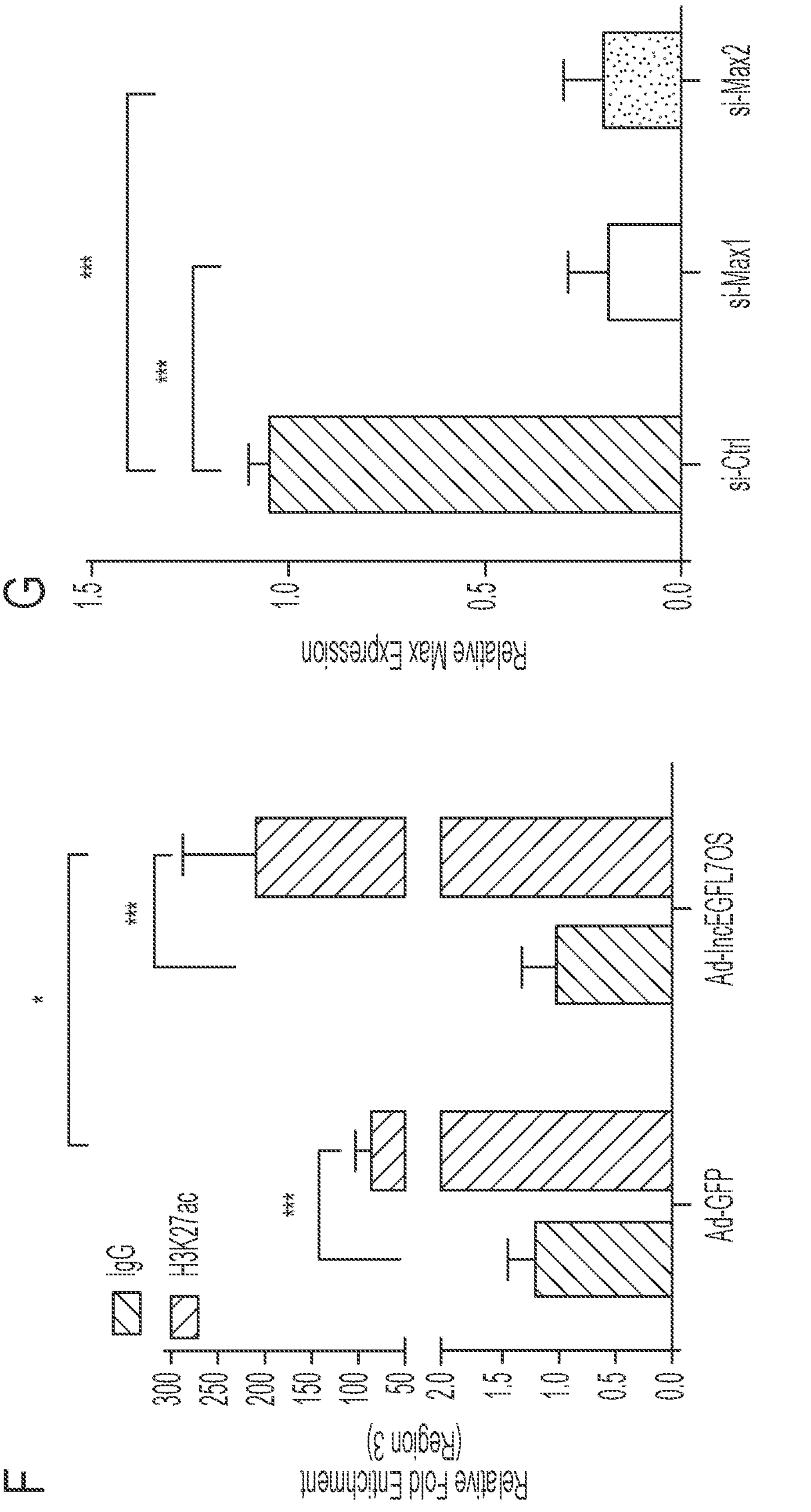
FIGS. 6F-G

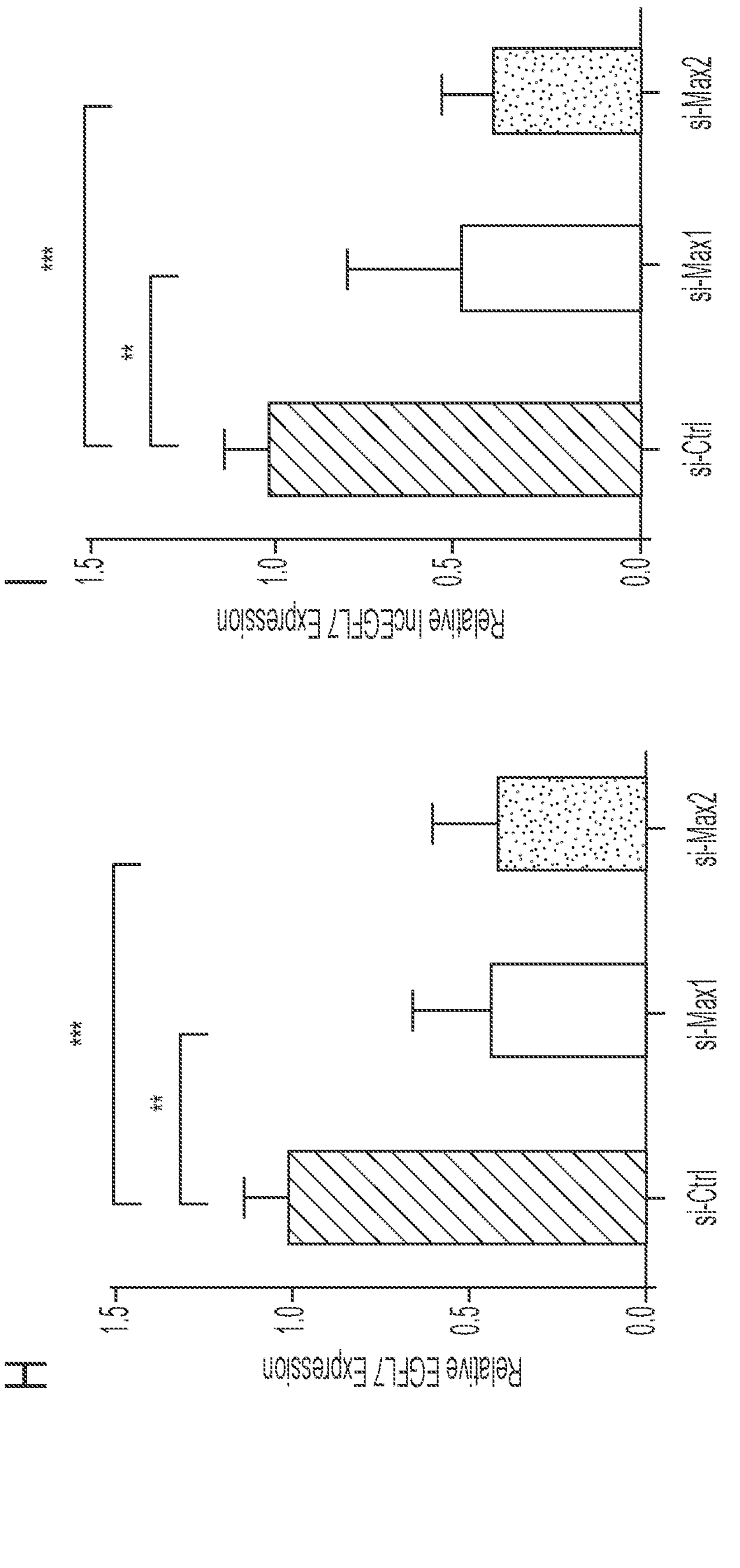
FIGS. 6H-I

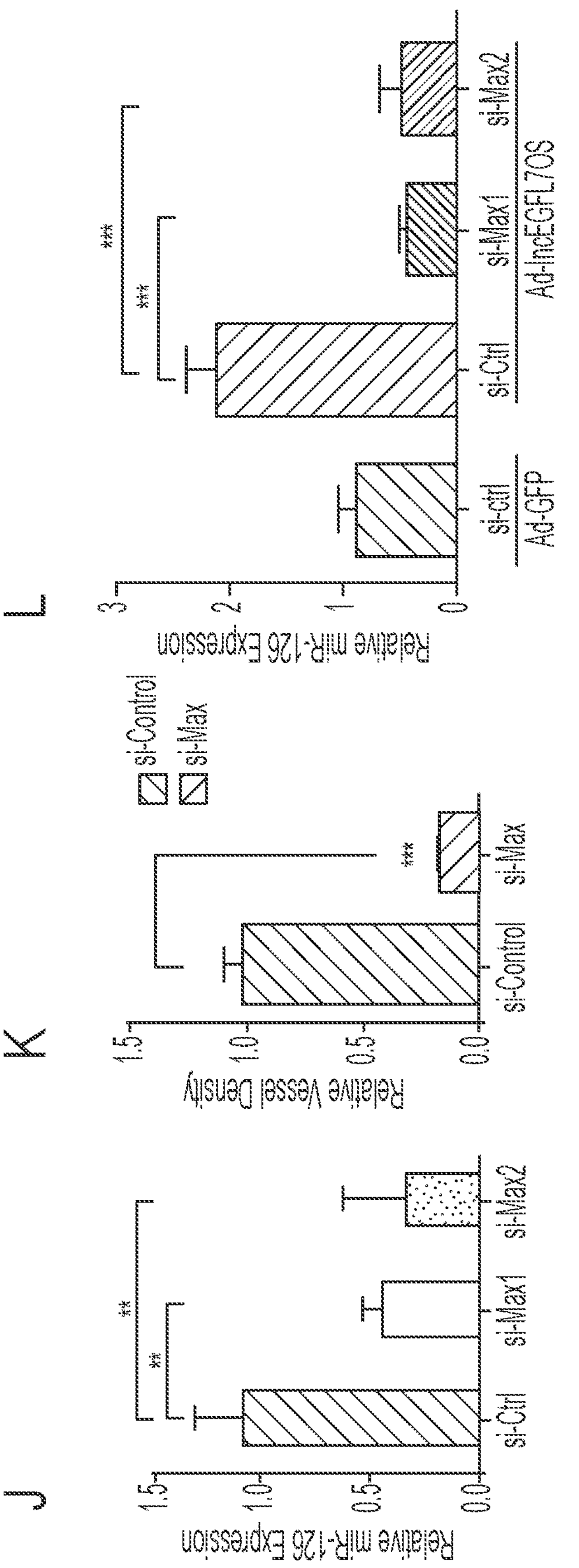
FIGS. 6J-L

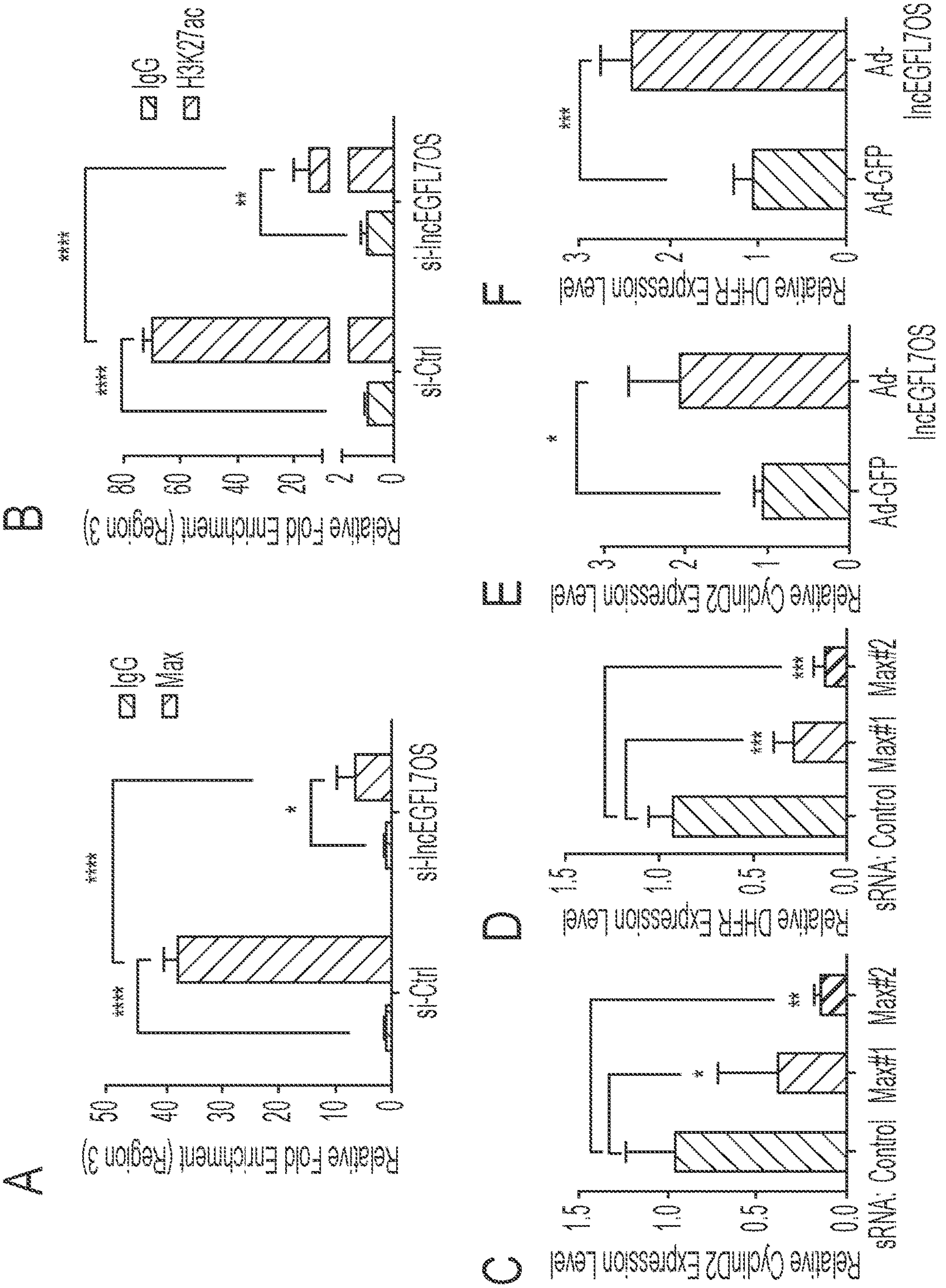
FIGS. 7A-F

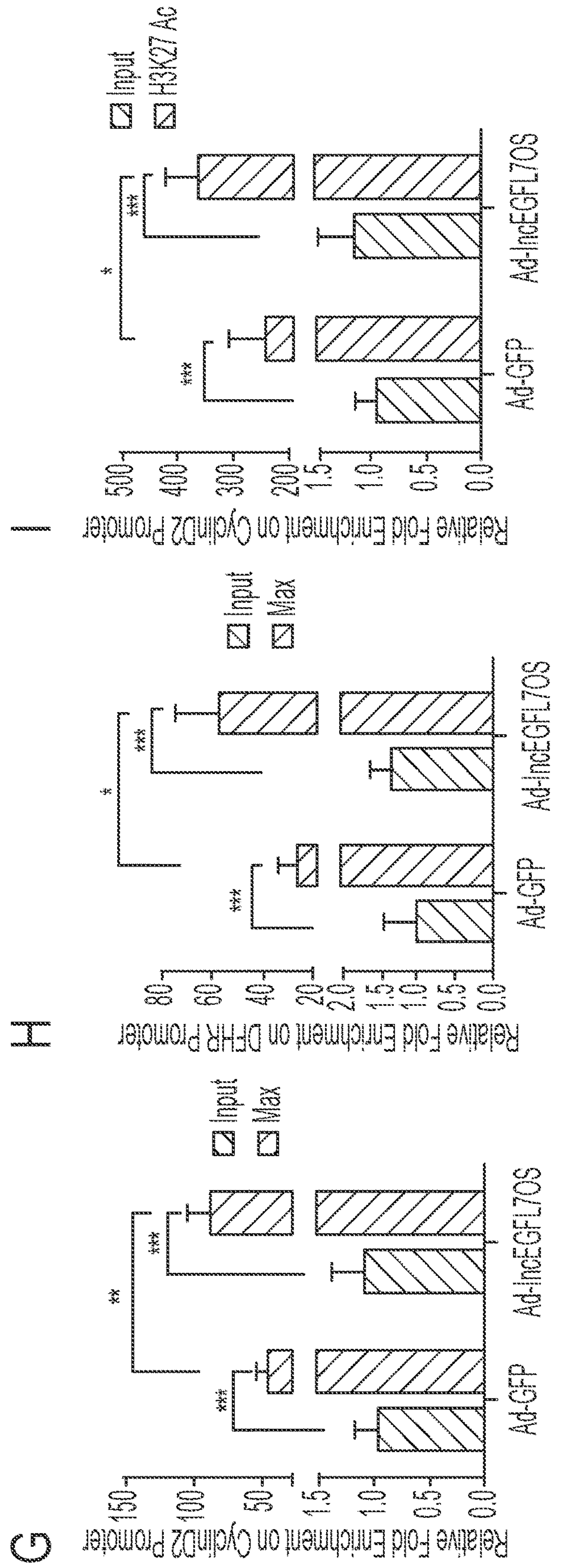
FIGS. 7G-I

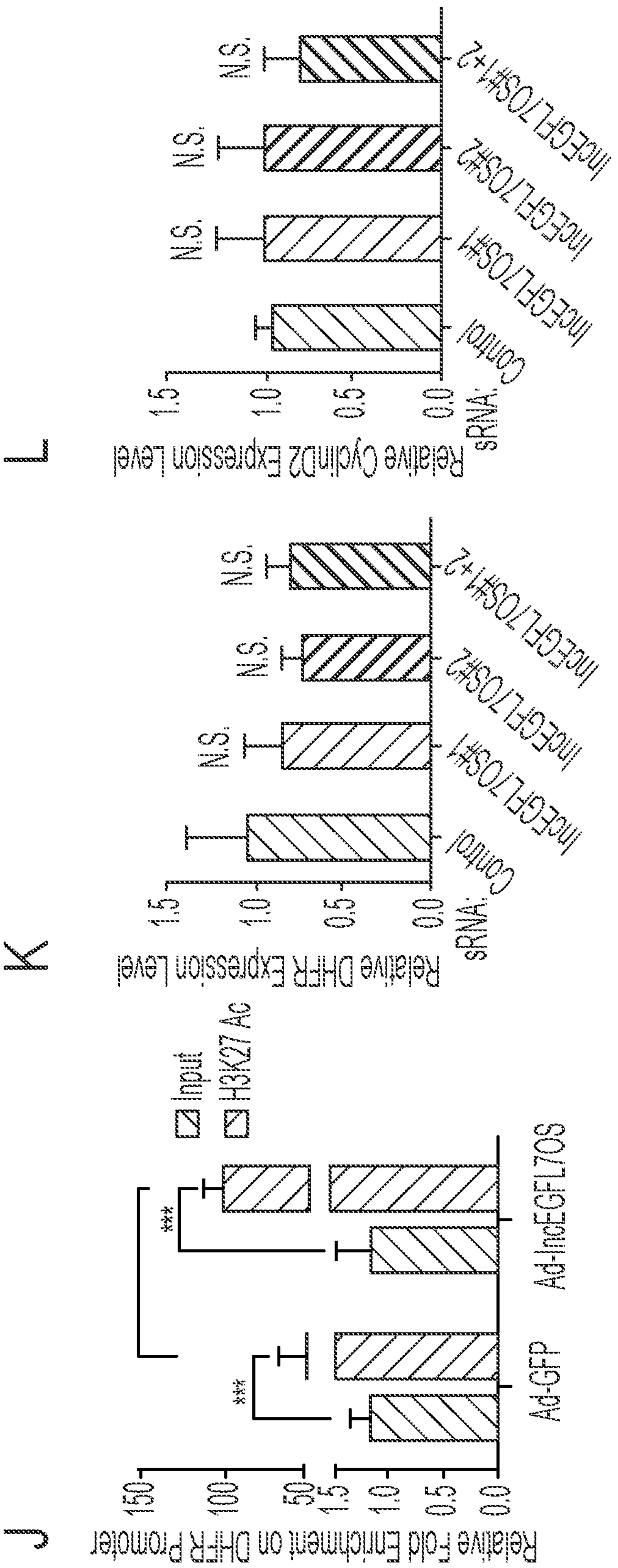
FIGS. 7J-L

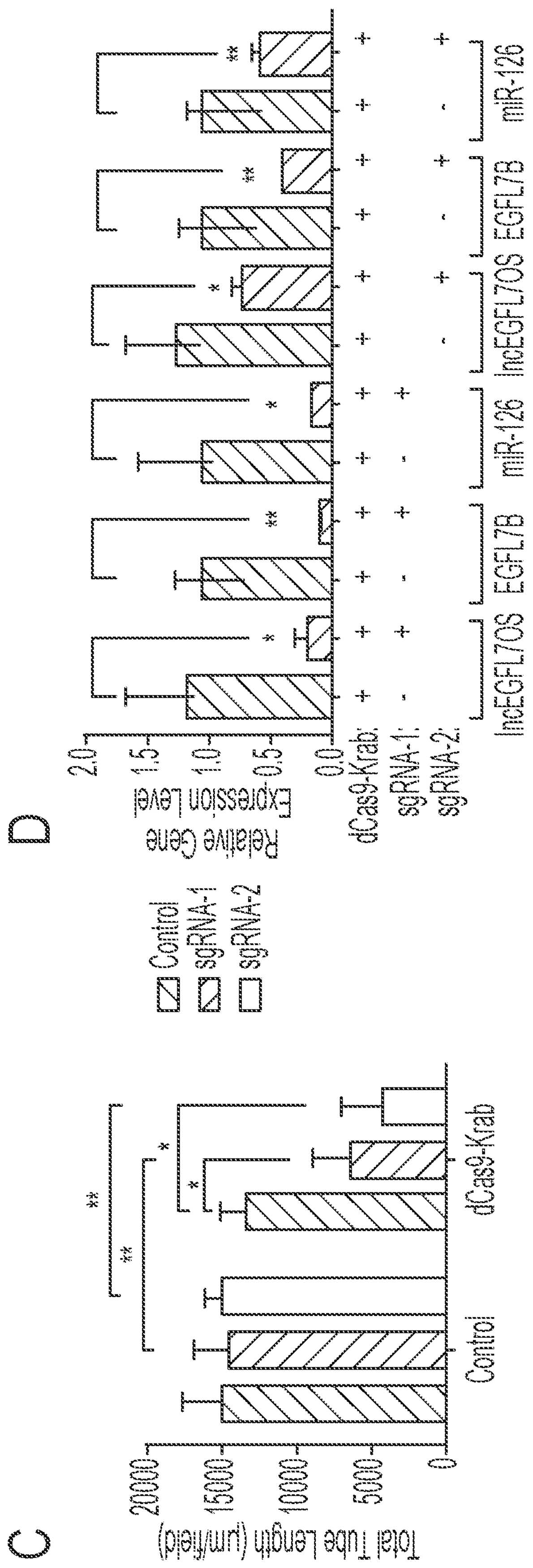
FIGS. 8C-D

B

| lncRNA gene symbol | Associated gene | Lung | Placenta | White Blood Cell | Heart | Liver | Adipose | Adrenal | Brain | Breast | Colon | Skin | Kidney | Lymph Node | Ovary | Prostate | Skeletal Muscle | Testes | Thyroid |
|---|---|---|---|---|---|---|---|---|---|---|---|---|---|---|---|---|---|---|---|
| SRGN | SRGN | 92 | 10 | 100 | 5 | 5 | 30 | 13 | 5 | 6 | 17 | 2 | 14 | 31 | 3 | 10 | 2 | 4 | 4 |
| Rp11-251M1.1 | EGFL7 | 100 | 3 | 0 | 0 | 2 | 3 | 4 | 0 | 4 | 0 | 0 | 0 | 0 | 0 | 0 | 0 | 2 | 0 |
| AC147651.4 | PRKAR1B | 100 | 8 | 16 | 2 | 4 | 8 | 25 | 3 | 3 | 1 | 1 | 2 | 14 | 1 | 4 | 4 | 6 | 2 |
| RP11-389C8.2 | | 32 | 61 | 20 | 100 | 8 | 84 | 57 | 9 | 90 | 68 | 0 | 57 | 85 | 39 | 42 | 11 | 42 | 28 |
| XLOC_003195 | | 100 | 0 | 0 | 1 | 11 | 0 | 0 | 3 | 17 | 0 | 0 | 0 | 0 | 12 | 0 | 0 | 0 | 16 |
| RP13-317D12_3 | PTDS52 | 2 | 101 | 19 | 0 | 8 | 7 | 4 | 3 | 13 | 12 | 12 | 3 | 78 | 17 | 50 | 17 | 36 | 31 |
| RP11-566K19.6 | | 4 | 6 | 2 | 8 | 0 | 5 | 6 | 100 | 7 | 7 | 8 | 13 | 9 | 4 | 13 | 0 | 21 | 4 |
| XLOC_009994 | | 84 | 0 | 0 | 10 | 10 | 0 | 95 | 14 | 14 | 0 | 102 | 0 | 0 | 37 | 92 | 0 | 71 | 25 |
| AC002480.4 | STEAP1B | 40 | 47 | 0 | 8 | 0 | 2 | 100 | 0 | 4 | 5 | 15 | 5 | 63 | 3 | 6 | 0 | 5 | 0 |
| LOC100505495 | | 100 | 11 | 0 | 9 | 2 | 16 | 28 | 1 | 16 | 48 | 0 | 20 | 28 | 14 | 12 | 3 | 9 | 5 |
| FUI-A51 | FU1 | 2 | 2 | 4 | 1 | 0 | 3 | 3 | 0 | 2 | 1 | 0 | 0 | 2 | 1 | 0 | 1 | 0 | 0 |
| AC116035.1 | | 39 | 0 | 0 | 20 | 0 | 43 | 100 | 0 | 41 | 0 | 0 | 9 | 51 | 8 | 21 | 15 | 45 | 3 |
| AC156455.1 | | 6 | 75 | 0 | 1 | 3 | 21 | 0 | 10 | 17 | 12 | 5 | 12 | 0 | 60 | 100 | 9 | 24 | 5 |
| AC226119.4 | | 100 | 118 | 0 | 1 | 0 | 0 | 3 | 18 | 0 | 0 | 0 | 0 | 0 | 7 | 0 | 0 | 24 | 0 |
| RP11-536K7.3 | | 100 | 36 | 0 | 0 | 5 | 16 | 17 | 0 | 1 | 3 | 16 | 0 | 6 | 3 | 6 | 0 | 0 | 10 |
| BCRP2 | | 63 | 22 | 35 | 17 | 11 | 23 | 64 | 83 | 58 | 42 | 12 | 78 | 85 | 49 | 30 | 2 | 100 | 75 |

FIG. 10B

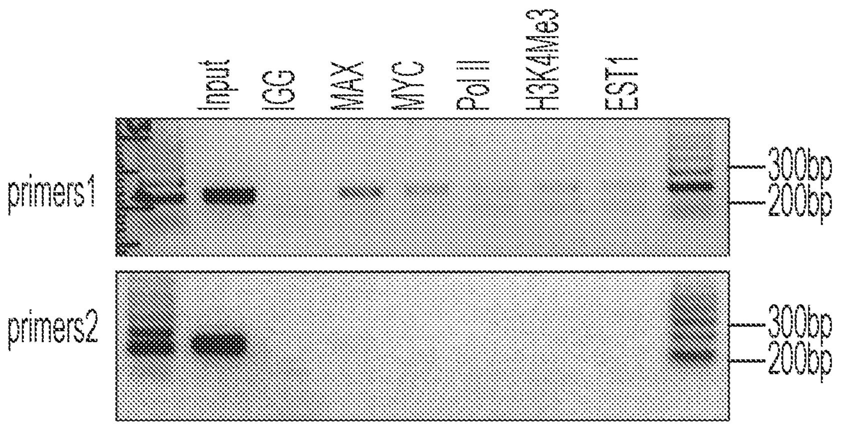
FIG. 11E
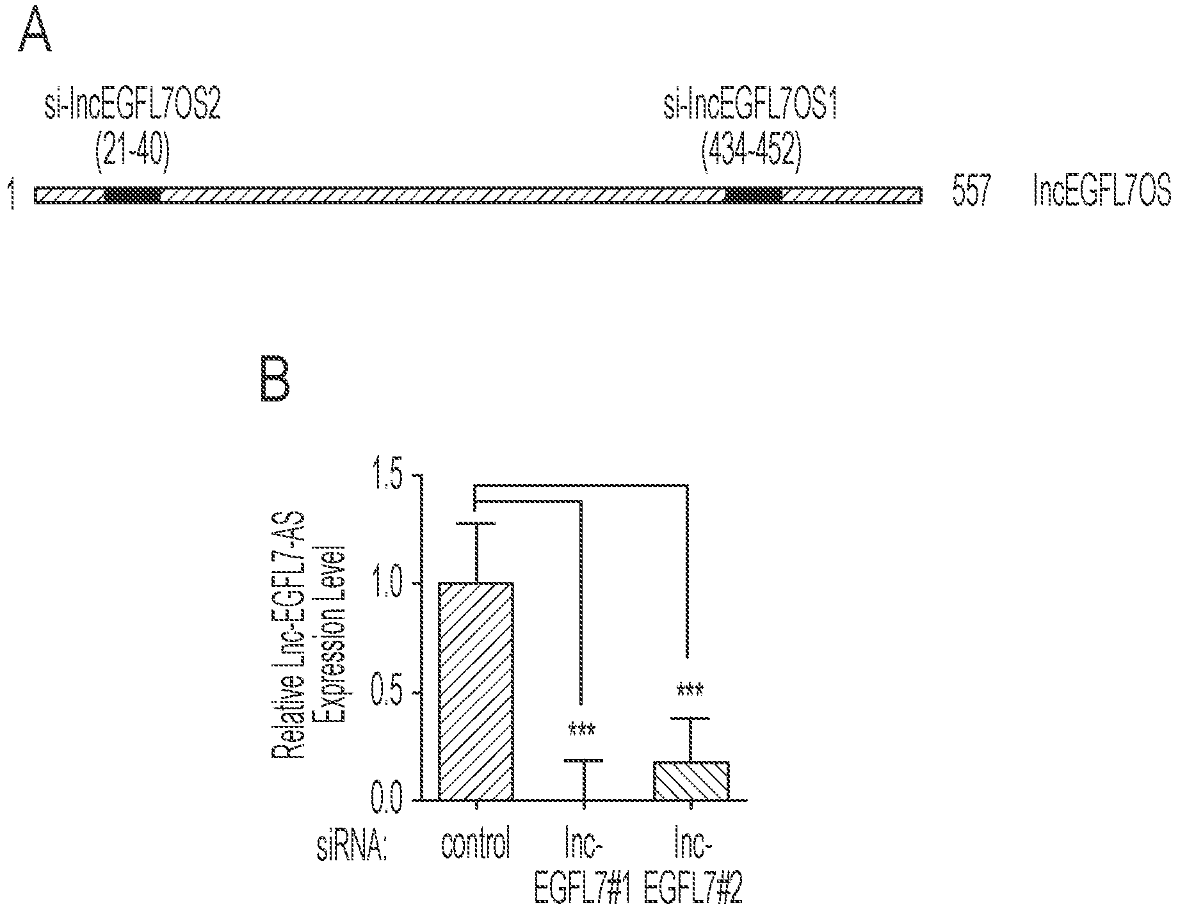
FIGS. 12A-B

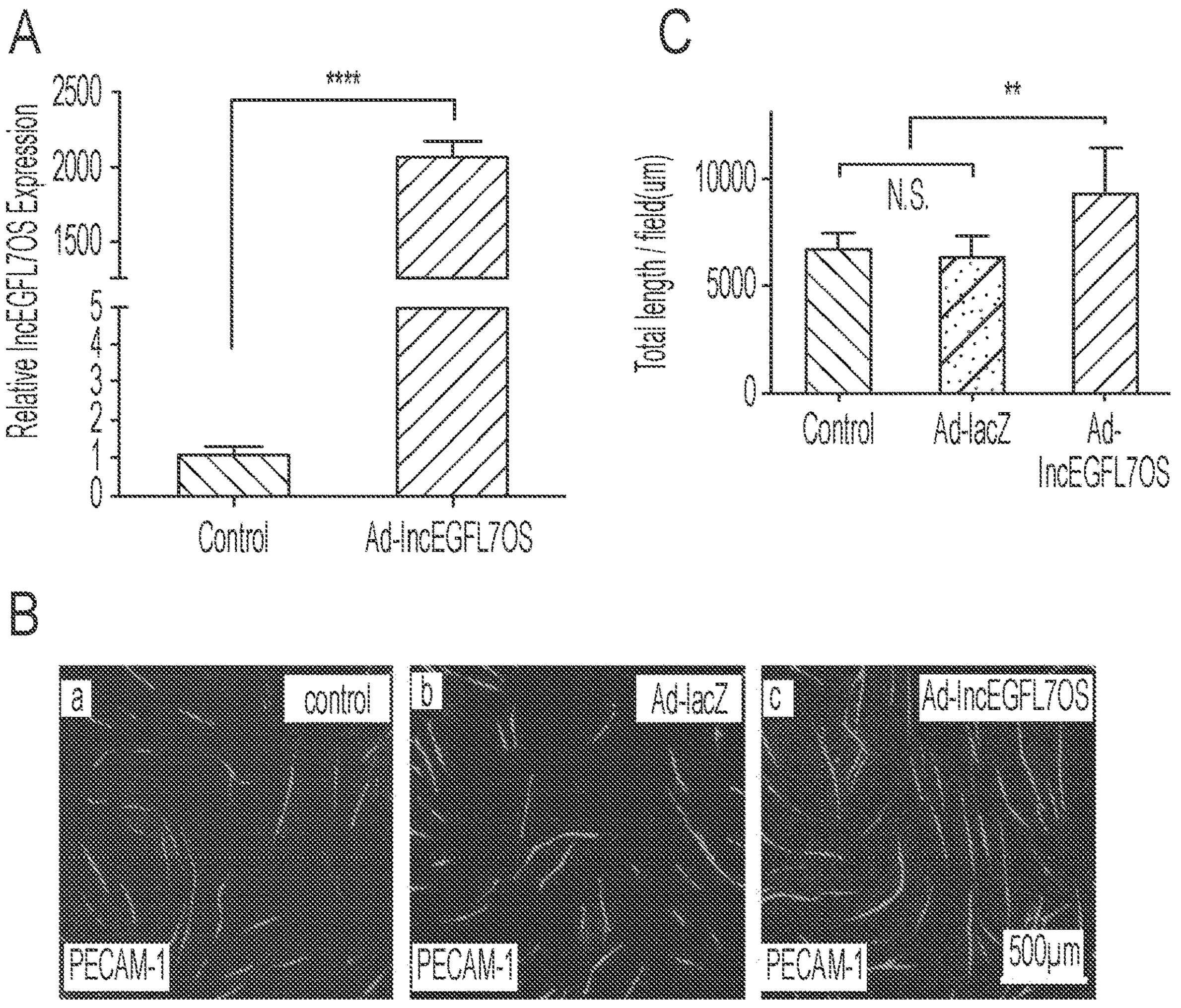
FIGS. 13A-C
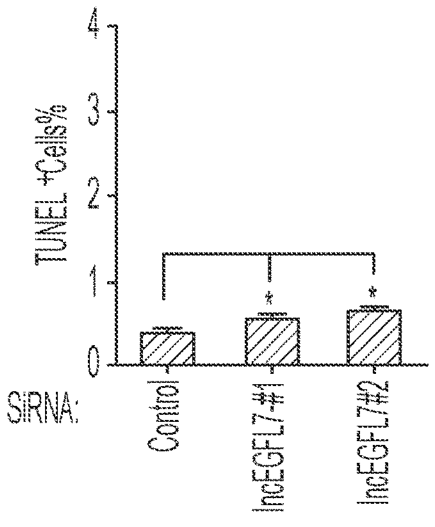
FIG. 13D

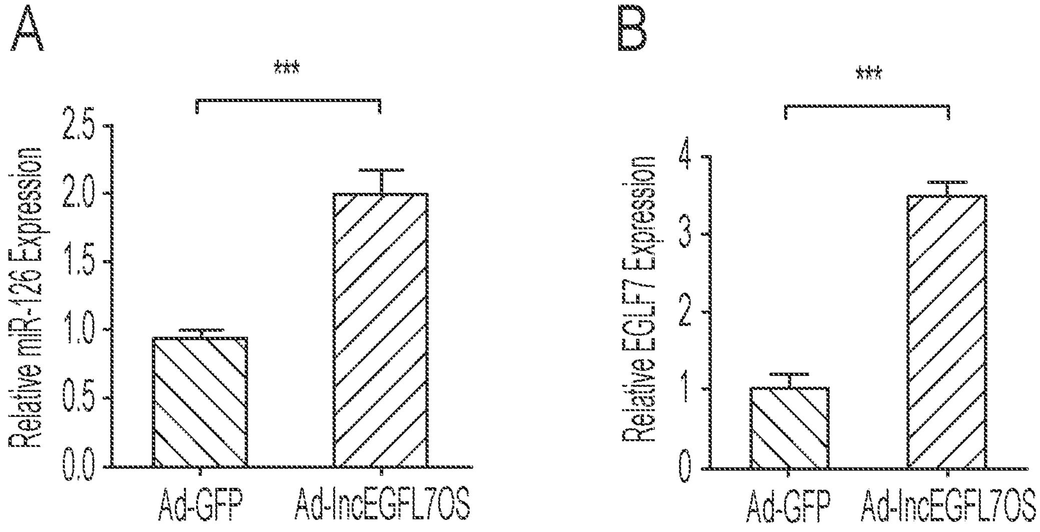
FIGS. 14A-B
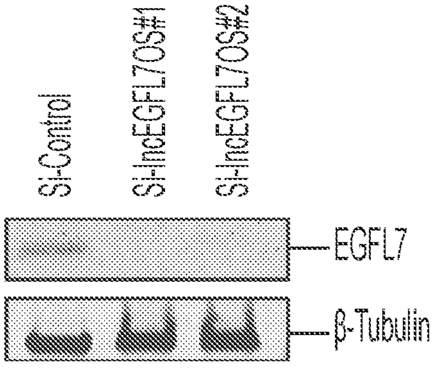
FIG. 14C

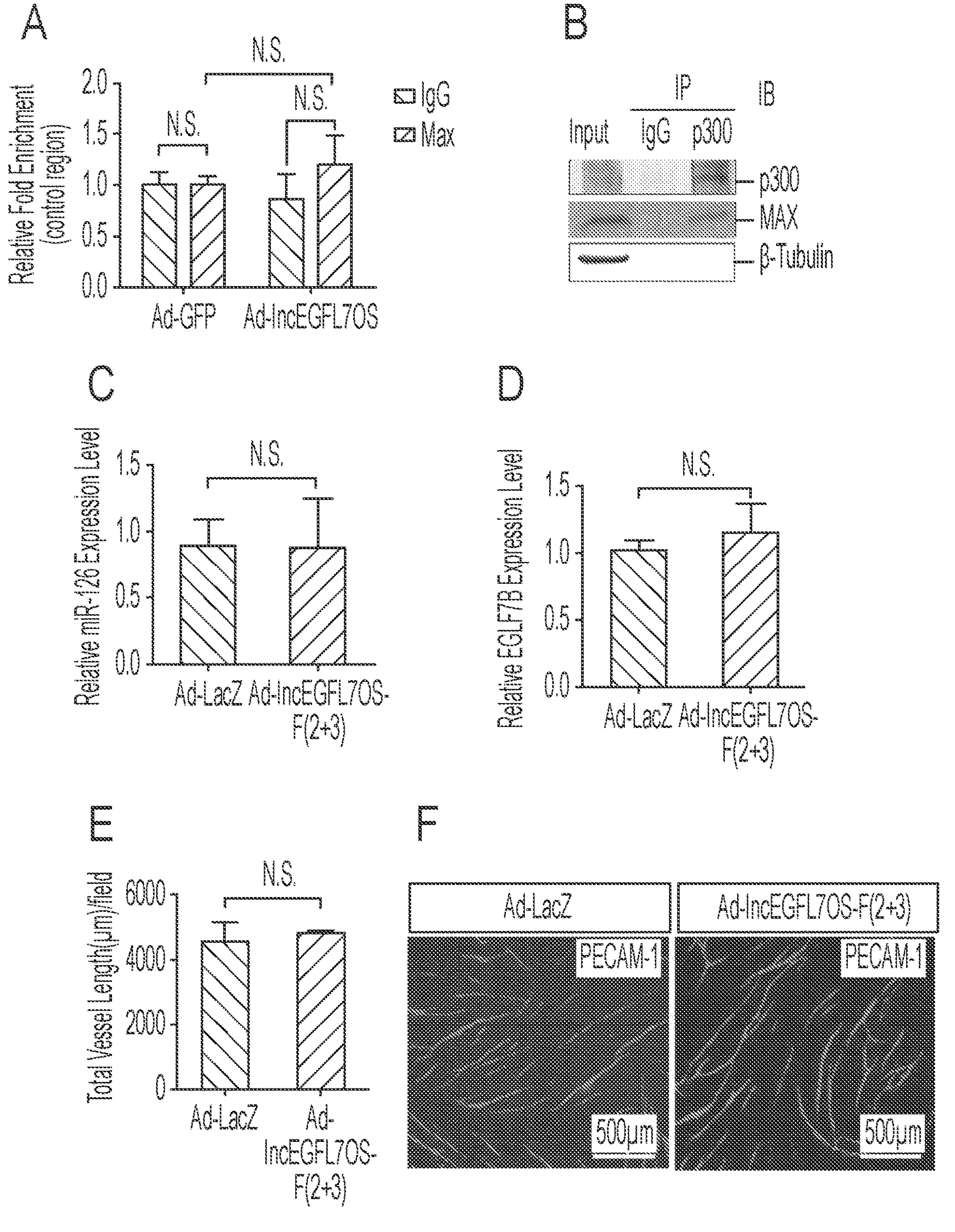
FIGS. 15A-F

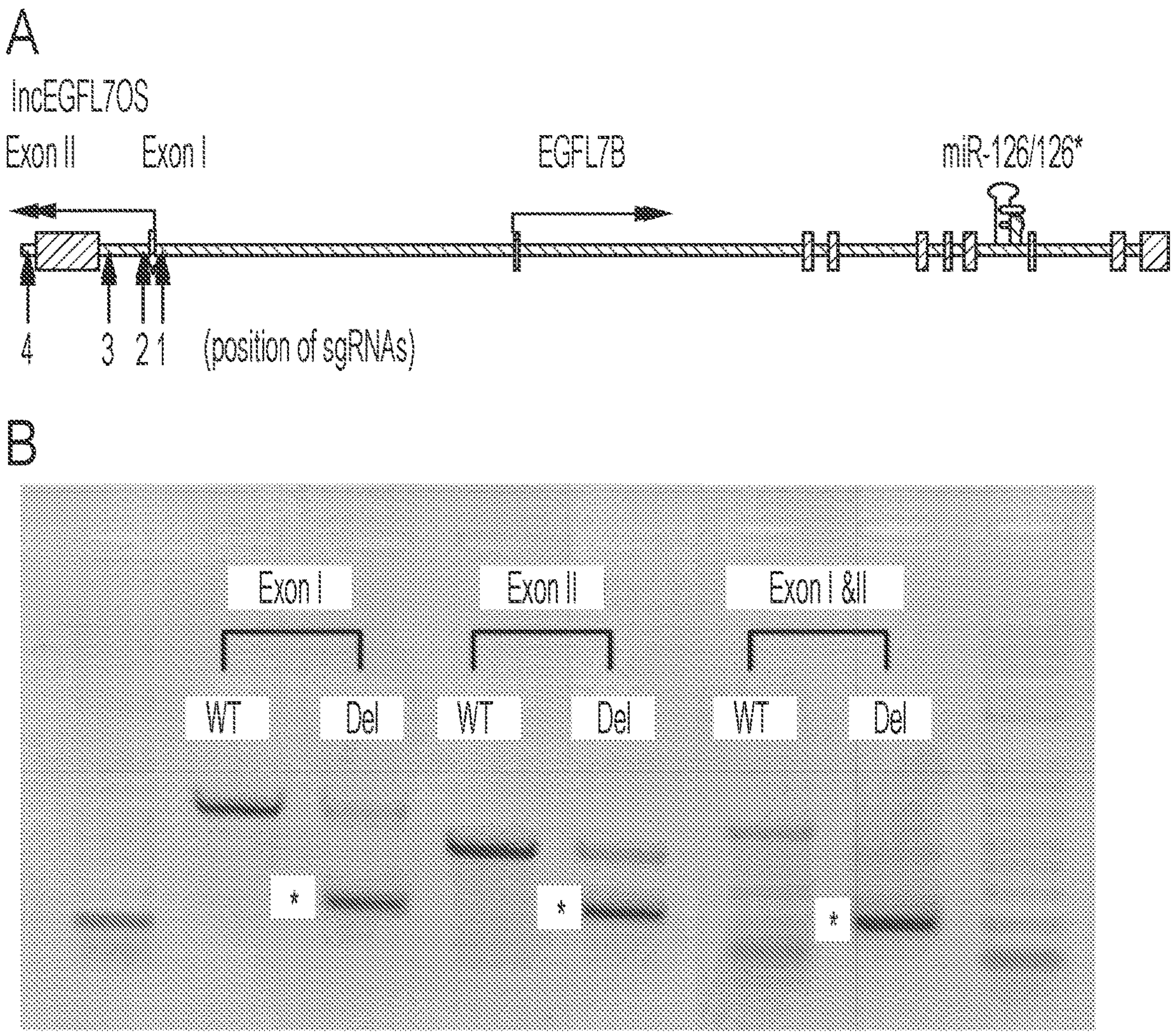
FIGS. 16A-B

CRISPR-BASED COMPOSITIONS FOR TREATING VASCULAR DISORDERS

PRIORITY CLAIM

This application is a national phase application under 35 U.S.C. § 371 of International Application No. PCT/US2020/015230, filed Jan. 27, 2020, which claims benefit of priority to U.S. Provisional Application Ser. No. 62/797,747, filed Jan. 28, 2019, the entire contents of each of which are hereby incorporated by reference.

STATEMENT REGARDING FEDERALLY SPONSORED RESEARCH

This invention was made with U.S. government support under National Institutes of Health Grant Nos. EY021862 and EY026069. The U.S. government has certain rights in this invention.

INCORPORATION BY REFERENCE OF PRIOR APPLICATIONS

This application also incorporates the entire contents of U.S. Provisional Application Ser. No. 62/304,015, filed Mar. 4, 2016, and U.S. application Ser. No. 15/448,225, filed on Mar. 2, 2017.

BACKGROUND

Angiogenesis plays a critical role in tissue development and homeostasis. Aberrant angiogenesis has been associated with numerous diseases, including heart disease, tumor growth, metastasis and age-related macular degeneration (AMD)[1]. Defective vascularization, usually associated with compensatory angiogenesis and vasculogenesis, has been observed in human dilated cardiomyopathy (DCM) patients[2-4]. Methods to augment angiogenesis have been tested clinically for DCM[5]. Anti-angiogenic therapy, such as antibodies to vascular endothelial growth factors (VEGF), has shown efficacy clinically in treating wet AMD, the leading blinding disease in the elderly[6-9]. However, some patients failed to respond to anti-VEGF treatment. Similarly, anti-angiogenic therapies have shown efficacy in certain cancers when used alone or combined with chemotherapy[10, 11]. However, anti-angiogenic therapy has met several hurdles on its way to be an main option for cancer therapy, mainly due to drug resistance[12]. Identifying novel human angiogenesis mechanism would provide important insights and potential therapeutic options for angiogenesis-related diseases.

It is now established that up to 90% of the human genome is transcribed, and the majority of these transcripts are non-coding RNAs (ncRNAs) that do not encode proteins[13-15]. NcRNAs can be classified as short noncoding RNAs such as microRNAs (miRNAs), long noncoding RNAs (lncRNAs) and other classic ncRNAs. miRNAs include a group of small noncoding RNAs sized ~22 nucleotides that play important regulatory functions in numerous physiological and pathological processes, including angiogenesis[16]. LncRNAs represent a large group of long (typically >200 nt) noncoding RNAs, whose function is still largely enigmatic[17]. The study of lncRNAs in vascular biology is still in its infancy[18,19]. Several lncRNAs, including MALATI[20,21], MANTIS[22], PUNISHER[23], MEG3[24,25], MIAT[26], SENCR[27]. GATA6-AS[28] and STEEL[29], have been shown to regulate angiogenesis. Dependent on their subcellular localizations, these lncRNAs function by regulating promoter and enhancer activities of angiogenesis-related genes in cis or modulating gene expression by in trans mechanism through interaction with DNA/RNA-binding proteins or chromatin modifying proteins or functioning as antisense RNAs to mRNAs or sponge for miRNAs in the cytoplasm. Additional information is urgently needed in order to employ ncRNAs in diagnosis and therapy.

SUMMARY

In one embodiment the present disclosure provides compositions comprised of single-guide ribonucleic acids (sgRNAs), a modified version of Cas9, and an expression vector and methods of use thereof to silence lncEGFL7OS, EGFL7, and miR-126, and repress angiogenesis in humans. In another embodiment the present disclosure provides compositions comprised of single-guide ribonucleic acids (sgRNAs), a modified version of Cas9, and an expression vector and methods of use thereof to activate lncEGFL7OS, EGFL7, and miR-126 to promote angiogenesis in humans. In another embodiment, overexpression or silencing of the genes that regulate lncEGFL7OS, EGFL7, and miR-126 expression to promote or inhibit angiogenesis also are contemplated. Such genes include ETS1, ETS2 and MAX.

In another embodiment, there is provided a composition comprising an agonist or antagonist of lncEGFL7OS, EGFL7, and miR-126 function in a pharmaceutically acceptable buffer, diluent or medium. The antagonist may comprise one or more of an sgRNA, dCas9-Krab, and an expression vector. The agonist may be an sgRNA, dCas9-VP16, and an expression vector. The expression vector may be a viral vector or a non-viral vector.

In yet another embodiment, there is provided a method of promoting vascular integrity and/or vascular repair comprising administering to a subject at risk of or suffering from vascular damage an agonist of lncEGFL7OS, EGFL7, and miR-126 function. The subject may be suffering from vascular damage, such as a cardiac tissue, and/or from an ischemic event. The ischemic event may comprise an infarct, ischemia-reperfusion injury or arterial stenosis. The vascular damage may be directed to a non-cardiac tissue, such as from trauma or vascular leakage. The subject may be at risk of vascular damage, such as due to hypertension, late stage atherosclerosis cardiac hypertrophy, osteoporosis, neurodegeneration, fibrosis or respiratory distress. The subject may be a non-human animal or a human.

The agonist may be sgRNA coupled with dCas9-VP16. The agonist may be an expression vector comprising an lncEGFL7-encoding nucleic acid segment under the control of a promoter active in a target cell. The target cell may be an endothelial cell or a hematopoietic cell. The promoter may be a tissue selective/specific promoter, such as one active in an endothelial cell or a hematopoietic cell. The expression vector may be a viral vector or a non-viral vector.

The method may further comprise administering to said subject a secondary therapy. The administering comprises systemic administration, such as oral, intravenous, or intra-arterial. Administering may be by osmotic pump or catheter. Administration may be directly to or local to vascular damaged tissue or a tissue at risk of vascular damage, such as to cardiac tissue, blood vessel tissue, bone tissue, neuronal tissue, respiratory tissue, eye tissue or placental tissue.

In still a further embodiment, there is provided a method of inhibiting pathologic vascularization in a subject in need thereof comprising administering to the subject at risk of or suffering from pathologic vascularization an antagonist of lncEGFL7OS, EGFL7, and miR-126. The subject may be suffering from pathologic vascularization, such as that associated with early stage atherosclerosis, retinopathy, cancer, age-related macular degeneration or stroke. The subject may be at risk of pathologic vascularization, such as that associated with hyperlipidemia, obesity, asthma, arthritis, psoriasis and/or blindness. The subject may be a non-human animal or a human.

The antagonist may be an sgRNA coupled with dCas9-Krab, or an inhibitor of ETS1, ETS2 and/or MAX expression or function. The antagonist may be delivered to a vasculature tissue, smooth muscle, ocular tissue, hematopoietic tissue, bone marrow, lung tissue or an epicardial tissue. The method may further comprise administering to said subject a secondary anti-angiogenic therapy. Administering may comprise systemic administration, such as oral, intravenous, intra-arterial administration. Administration may be directly to or local to pathologic vascularization or a tissue at risk of pathologic vascularization, such as to ocular tissue, a vascular tissue, bone tissue, fat tissue or lung tissue. Administering may be by osmotic pump or catheter.

In still yet an additional embodiment, the present disclosure provides compositions comprised of single-guide (sgRNAs) coupled with Cas9-KRAB and methods of use thereof to activate or silence the following EC-enriched lncRNAs to repress or activate angiogenesis in humans: Friend leukemia integration 1 (FLI1) antisense lncRNA (lncFLI1, ASHGA5P026051 (also known as SENCR), GATA binding protein 2 (GATA2) antisense lncRNA (lncGATA2, ASHGA5P019223, RP11-475N22.4), endothelial converting enzyme 1 (ECE1) intron sense-overlapping lncRNA (lncECE1, ASHGA5P032664, AX747766), endothelial cell-selective adhesion molecule (ESAM) bidirectional lncRNA (lncESAM, ASHGA5P021448, RP11-677M14.3), roundabout homolog 4 (ROBO4) nature antisense RNA (lncROBO4, ASHGA5P026882, RP 11-664I21.5).

While certain features of this disclosure shown and described below are pointed out in the annexed claims, the disclosure is not intended to be limited to the details specified, since a person of ordinary skill in the relevant art will understand that various omissions, modifications, substitutions and changes in the forms and details of the disclosure illustrated and in its operation may be made without departing in any way from the spirit of the present disclosure. No feature of the disclosure is critical or essential unless it is expressly stated as being "critical" or "essential."

Wherever any of the phrases "for example," "such as," "including" and the like are used herein, the phrase "and without limitation" is understood to follow unless explicitly stated otherwise. Similarly, "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function. The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

BRIEF DESCRIPTION OF THE DRAWINGS

The following drawings form part of the present specification and are included to further demonstrate certain aspects of the present disclosure. The disclosure may be better understood by reference to one or more of these drawings in combination with the description of specific embodiments presented herein.

FIGS. 1A-D. lncRNA profiling in ECs. (FIG. 1A) Hierarchy cluster analysis of lncRNA and mRNA expression data from 5 different cell lines. (FIG. 1B) Heatmap showing the top-50 enriched lncRNAs in three EC lines compared to the two non-EC lines. Several highlighted lncRNAs were used in the subsequent qRT-PCR confirmation in FIG. 1D. (FIG. 1C) A pie chart showing different classes of annotated lncRNAs that are enriched more than 2 folds in ECs compared to non-ECs. (FIG. 1D) Quantitative (q) RT-PCR confirmation of candidate EC-enriched lncRNAs. n=3. Error bars represent the standard error from three technical repeats from each line. GAPDH was used as normalization control.

FIGS. 2A-H. Expression, regulation and subcellular localization of lncEGFL7OS, as well as its regulation in DCM patients. (FIG. 2A) Genomic organization of lncEGFL7OS and its host gene EGFL7/miR-126. Exons are shown in orange and the introns are shown in blue. Direction of gene transcription is indicated by arrows. Scale=1 kb. (FIG. 2B) Relative lncEGFL7OS expression level in different human tissues. GAPDH served as the normalization control. (FIG. 2C) Expression of lncEGFL7OS in the nucleus and cytoplasm of HUVECs shown by semi-quantitative RT-PCR. RT-PCR showing nuclear and cytoplasmic expression of lncEGFL7OS. SENCR was used a marker for cytoplasmic-enriched lncRNA, while NEAT-1 was used as a marker for nuclear-enriched lncRNA. (FIG. 2D) Expression of lncEGFL7OS in the nucleus and cytoplasm of HUVECs shown by high-resolution RNA FISH analysis (a-c). RNaseA-treated samples were used as negative control (a) and Ad-lncEGFL7OS-overexpressed HUVECs were used as positive control (b). Scale Bar equals 10 μm. (FIG. 2E) Upregulation of lncEGFL7OS, EGFL7B and C, and pri-miR-126 om the hearts of DCM patients. *, $p<0.05$; , $p<0.01$. N=6 for control samples and N=7 for DCM samples. (FIG. 2F) Schematic potential promoter region (boxed) for EGFL7/lncEGFL7OS. Exons are shown in orange and the introns are shown in blue. Direction of gene transcription is indicated by red arrows. The peaks show regions with elevated H3K4Me1. H3K4Me3 and H3K27Ac binding as predicted by ENCODE, respectively. The boxed region was shown by ENCODE to bind MAX, MYC, ETS1, RNA PolR II, H3K4Me1, H3K4Me3 and H3K27Ac (genome.ucsc.edu). Eight cell types were tracked in the image. Light blue indicates HUVEC cells, while dark color indicates H7-ES cells. Scale=1 kb. (FIG. 2G) Testing bidirectional lncEGFL7OS promoter. LncEGF7OS promoter was fused to a promoter-less Luciferase vector in forward (F) and reverse (R) directions and tested for Luciferase activity with or without co-transfection of ETS1 or ETS1 mutant expression plasmid in 293T cells. Shown here is the representative results from 3 repeats. (FIG. 2**H) qRT-PCR showing that silencing of ETS1/2 result in the downregulation of lncEGFL7OS and pri-miR-126 (n=3). *, p<0.05; ***, p<0.001.

FIGS. 3A-H. Regulation of angiogenesis by lncEGFL7OS in vitro, ex vivo and in vivo. (FIG. 3A) Decreased capillary tube formation at 7 days after lncEGFL7OS silencing in HUVECs in an EC-fibroblast co-culture assay. The capillaries are stained with PECAM-1 antibody. Scale bar equals to 500 μm. (FIG. 3B) Quantification of total tube length in A (n=3 each). Two independent lncEGFL7OS siRNAs were used for quantification. **, p<0.0001. (FIG. 3C) Defective EC networking at 14 days after lncEGFL7OS silencing in an in vivo Matrigel implantation model. A mix of si-linEGFL7OS #1 and si-lncEGFL7OS #2 was use for the experiments. HUVEC cells in the Matrigel were stained with human PECAM-1 antibody (Red), mouse red blood cells were stained with mouse Ter-119 (Green) antibody and mouse smooth muscle cells were stained with α-SMA (Green) antibody. Arrows label the representative areas with overlapping staining in the Matrigel. DAPI was used to stain nucleus. Scale bar equals to 200 μm. (FIG. 3D) Quantification of tubule length in C (n=3 mice each). , p<0.01. (FIG. 3E) Inhibition of lncEGFL7OS expression by si-lncEGFL7OS-1/2 in human choroids cultured ex vivo, as revealed by qRT-PCR (n=3). (FIG. 3F) Representative picture of human choroid sprouting angiogenesis after lncEGFL7OS knockdown. (FIG. 3G) Quantification of choroid sprouting distance in FIG. 3F (n=6). (FIG. 3H) Representative ICAM2 (green) and Isolectin B4 (red) staining of the choroid sprouts in FIG. 3F. Scale bar equals to 250 μm.

FIGS. 4A-E. Regulation of EC proliferation and migration by lncEGFL7OS. (FIG. 4A) Quantification of EC proliferation in response to VEGF-A as indicated by BrDU incorporation after lncEGFL7OS silencing (n=3). (FIG. 4B) Representative ell cycle profile in ECs after lncEGFL7OS silencing. (FIG. 4C) Statistics of the percentage of cells in different phases of cell cycle after lncEGFL7 silencing (n=3). *, p<0.05; , p<0.01; *, p<0.001. (FIG. 4D) Repression of cell migration in a scratch wound assay in ECs after lncEGFL7OS silencing. Dashed lines indicate the initial position of cells. Scale bar equals to 100 μm. (FIG. 4E) Quantification of EC migration in D (n=3). **, p<0.01.

FIGS. 5A-E. Regulation of EGFL7/miR-126 and angiogenic signaling by lncEGFL7OS. (FIG. 5A) Expression of EGFL7 B and EGFL7C by qRT-PCR after lncEGFL7OS knockdown in ECs (n=3). GAPDH served as normalization control. (FIG. 5B) Expression of miR-126 and miR-126* after lncEGFL7OS knockdown in ECs (n=3). U6 served as normalization control. (FIG. 5C) Regulation of ERK1/2 and AKT phosphorylation by lncEGFL7OS knockdown in ECs in response to VEGF treatment, as revealed by Western blot. Total ERK1/2 and AKT were used as controls. β-Tubulin was used as a loading control. (FIG. 5D) Rescue of the lncEGFL7OS-knockdown angiogenic phenotype by EGFL7 protein/Adeno-miR-126 in an EC-fibroblast co-culture assay. Scale bar equals to 500 μm. (FIG. 5E) Quantification of the total tube length in D (n=3). *, P<0.05. *, p<0.001, **, p<0.0001.

FIGS. 6A-L. lncEGFL7OS regulates EGFL7/miR-126 transcription by interaction with MAX transcription factor. (FIG. 6A) Schematic EGFL7/miR-126 enhancer/promoter region. The boxed region is predicted by ENCODE to bind MAX and H3K27Ac. (FIG. 6B) RIP-PCR showing binding of MAX to lncEGFL7OS in ECs. Overexpression of lncEGFL7OS by adenovirus enhances MAX binding. The bottom line shows a non-RT control for PCR (FIG. 6C) Schematics of the lncEGFL7OS fragments for the MAX binding assay. (FIG. 6D) RIP PCR showing specific binding of F1 fragment of lncEGFL7OS to MAX protein. Input RT-PCR showed the expression of lncEGFL7 fragments in transfected RPE-19 cells. RIP RT-PCR showed the specific binding of F1 fragment to MAX by RIP assay. RIP RNA-PCR showed the DNase I treated non reverse transcription control. (FIG. 6E) ChIP-PCR showing specific binding of MAX to region 3 in A. Overexpression of lncEGFL7OS enhances MAX binding to the region. *, p<0.05; **, p<0.01. (FIG. 6F) ChIP-PCR showing specific binding of H3K27ac to region 3 in A. Overexpression of lncEGFL7OS enhances H3K27ac binding to the region. *, p<0.05; *, p<0.001. (FIG. 6G) Silencing of MAX expression by two independent siRNAs as shown by qRT-PCR. *, p<0.001. (FIG. 6H) Downregulation of EGFL7B by MAX silencing in ECs. , p<0.01, *, p<0.001. (FIG. 6I). Downregulation of lncEGFL7OS by MAX silencing in ECs. , p<0.01, *, p<0.001. (FIG. 6J) Downregulation of miR-126 by MAX silencing in ECs. , p<0.01. (FIG. 6K) Quantification of vessel density in an EC-Fibroblast co-culture assay after MAX silencing. A mix of two independent MAX siRNAs was used in the assay. , p<0.01. (FIG. 6L) MAX silencing blunts the induction of miR-126 by lncEGFL7OS-expressing adenovirus. ***, p<0.001.

FIGS. 7A-L. lncEGFL7OS-depedent MAX-regulated gene expression is locus dependent. (FIG. 7A) ChIP-PCR showing specific binding of MAX to region 3 (as in FIG. 6A). Silencing of lncEGFL7OS decreased MAX binding to the region (n=3). *, p<0.05; *, p<0.001. (FIG. 7B) ChIP-PCR showing specific binding of H3K27ac to region 3 (as in FIG. 6A). Silencing of lncEGFL7OS decreased H3K27ac binding to the region (n=3). , p<0.01; ***, p<0.001. (FIG. 7C) Repression of Cyclin D2 expression in HUVEC cells by MAX knockdown using two independent siRNAs (n=3). *, p<0.05; **, p<0.01. (FIG. 7D) Repression of DHFR expression in HUVEC cells by MAX knockdown using two independent siRNAs (n=3). *, p<0.05; **, p<0.01. (FIG. 7E) lncEGFL7OS overexpression enhances Cyclin D2 expression (n=3). *p<0.05. (FIG. 7F) lncEGFL7OS overexpression enhances DHFR expression (n=3). *, p<0.001. (FIG. 7G). ChIP-PCR showing specific binding of MAX to the Cyclin D2 promoter. Overexpression of lncEGFL7OS further enhances MAX binding to the region (n=3). , p<0.01; ***, p<0.001. (FIG. 7H) ChIP-PCR showing specific binding of MAX to the DHFR promoter. Overexpression of lncEGFL7OS further enhances MAX binding to the region (n=3). *, p<0.05; ***, p<0.001. (FIG. 7I). ChIP-PCR showing increased H3K27 acetylation at the Cyclin D2 promoter. Overexpression of lncEGFL7OS further enhances H3K27 acetylation at the region (n=3). *, p<0.05; *, p<0.001. (FIG. 7J) ChIP-PCR showing increased H3K27 acetylation at the DHFR promoter. Overexpression of lncEGFL7OS further enhances H3K27 acetylation at the region (n=3). , p<0.01; ***, p<0.001. (FIG. 7K) qRT-PCR showing no effect of lncEGFL7 knockdown on Cyclin D2 expression (n=3). N.S., non-significant. (FIG. 7L) qRT-PCR showing no effect of lncEGFL7 knockdown on DHFR expression (n=3). N.S., non-significant.

FIGS. 8A-D. Inhibition of angiogenesis by CRISPR-mediated targeting of the EGFL7/miR-126/lncEGFL7OS locus. (FIG. 8A) Schematic locations of the sgRNAs in the EGFL7/miR-126/lncEGFL7OS genes. (FIG. 8B) Representative images showing sgRNA mediated repression of angiogenesis in an EC-fibroblast co-culture assay. The capillaries are stained with PECAM-1 antibody. Scale bar equals to 500 μm. All constructs were made into lentivirus. Lenti-control vector: pLJM1-EGFP; Lenti-dCas9-Krab: pHR-SFFV-dCas9-BFP-KRAB: sgRNA-1: lentiGuide-gRNA1: sgRNA-2: lentiGuide-gRNA2: Control: lentiGuide-Puro. (FIG. 8C) Quantification of total tube length in B (n=3 each). Two independent sgRNAs were used for quantification. *, p<0.05; , p<0.01. (FIG. 8**D) Expression of lncEGFL7OS, EGFL7B and miR-126 at 48 hours after transduction in B by qRT-PCR. *, p<0.05; **, p<0.01.

FIGS. 10A-C. (FIG. 10A) Functional enrichment analysis of EC-enriched lncRNAs and their associated genes. P-values are indicated. (FIG. 10B) Tissue distribution of the candidate lncRNAs from the top-50 EC-enriched lncRNA list based on bioinformatics data. The tissue expression data of the top-50 EC-enriched lncRNAs were searched from the Stanford Source database, and the available information was shown in the table. Expression level was shown and was visualized artificially with heat-map (green represents high expression and red represents low expression). FIG. 10C (upper panels). Uptake of DiI labeled Acetyl-LDL in the EC lines (HUVEC, HREC and HCEC); (lower panels). Staining of the EC lines with antibody to EC marker vWF.

FIGS. 11A-E. (FIG. 11A) Gel picture of RACE-PCR product of lncEGFL7OS from RACE-ready human placenta cDNA. Marker size was shown. (FIG. 11B) Expression of EGFL7B and EGFL7C by qRT-PCR in different human tissues. GAPDH served as the normalization control. (FIG. 11C) Relative miR-126 expression level in different human tissues. U6 served as normalization control. (FIG. 11D) qRT-PCR detection of ANP and PECAM-1 in the hearts of DCM patients. 5 controls and 7 DCM patients were used in the study. *, p<0.05. (FIG. 11E) ChIP assay showing binding for the indicated factors to the promoter region (n=3 each). IgG was used as control. The positions for PCR primers were shown in FIG. 2F. Size of the marker was shown.

FIGS. 12A-C. (FIG. 12A) Schematics of the siRNA locations in lncEGFL7OS. (FIG. 12B) Silencing of lncEGFL7OS by siRNAs as shown by qRT-PCR (n=3). *, p<0.001. (FIG. 12C) (upper panel) Single channel image of the Matrigel assay in FIG. 3C. HUVEC cells were stained with human PECAM-1 antibody (Red) and mouse red blood cells were stained with mouse Ter-119 (Green) antibody. DAPI was used to stain nucleus; (lower panel) Single channel image of the Matrigel assay in FIG. 3**C. HUVEC cells were stained with human PECAM-1 antibody (Red) and mouse smooth muscle cells were stained with α-SMA (Green) antibody. DAPI was used to stain nucleus.

FIGS. 13A-D. (FIG. 13A) qRT-PCR showing overexpression of lncEGFL7OS in ECs infected with lncEGFL7OS expressing adenovirus. LacZ expression virus was used as control. (FIG. 13B) Representative images showing enhanced angiogenesis at 7 days after lncEGFL7OS overexpression in an EC-fibroblast co-culture assay. LacZ or noninfection samples were used as controls. Scale bar equals to 500 μm. (FIG. 13C) Quantification of tube length/area in B (n=3). , P<0.01. (FIG. 13**D) Quantification of TUNEL positive cells in ECs transfected siRNAs for lncEGFL7OS (n=3). *, p<0.05.

FIGS. 14A-C. (FIG. 14A) qRT-PCR showing upregulation of miR-126 expression in ECs infected with lncEGFL7OS expressing adenovirus. GFP expression virus was used as control (n=3). *, p<0.001. (FIG. 14B) qRT-PCR showing upregulation of EGFL7B expression in ECs infected with lncEGFL7OS expressing adenovirus. GFP expression virus was used as control (n=3). *, p<0.001. (FIG. 14C) Expression of EGFL7 protein by Western blot after lncEGFL7OS knockdown in ECs (n=3). β-Tubulin was used as a loading control.

FIGS. 15A-F. (FIG. 15A) ChIP-PCR showing no specific binding of MAX to a control region (primer1 2 set in material and method section). Overexpression of lncEGFL7OS does not affect MAX binding to the region (n=3). N.S., non-significant. (FIG. 15B) Interaction of MAX and p300 in HUVECs by co-immunoprecipitation assay. HUVEC cell lysate was immunoprecipitated with antibody to p300, and blotted with MAX, p300, β-Tubulin antibodies. (FIG. 15C) qRT-PCR showing overexpression of lncEGFL7OS-F (2+3) does not affect miR-126 expression. ECs were infected with incEGFL7OS-F (2+3)-expressing adenovirus. LacZ expression virus was used as control. N.G., non-significant. (FIG. 15D) qRT-PCR showing overexpression of lncEGFL7OS-F (2+3) does not affect EGFL7B expression. ECs were infected with lncEGFL7OS-F (2+3)-expressing adenovirus. LacZ expression virus was used as control. N.G., non-significant. (FIG. 15E) Quantification of the total vessel length in an EC-fibroblast co-culture assay showing that overexpression of lncEGFL7OS-F (2+3) does not affect angiogenesis in vitro (n=3). ECs were infected with lncEGFL7OS-F (2+3)-expressing adenovirus. LacZ expression virus was used as control. N.G., non-significant. (FIG. 15F) Representative images of the experiments in E after PECAM-1 staining of ECs. Scale bar equals to 500 μm.

FIGS. 16A-B. (FIG. 16A) Strategy for generation of lncEGFL7OS knockout ECs using CRISPR technology. Positions of guide RNAs to delete Exon I and Exon II of lncEGFL7OS were shown. (FIG. 16B) Efficient deletion of Exon I and/or Exon II in 293T cells using the strategy in FIG. 16A. * indicates the bands after exon I and/or II deletion.

DETAILED DESCRIPTION OF THE DISCLOSURE

Figure 1A:
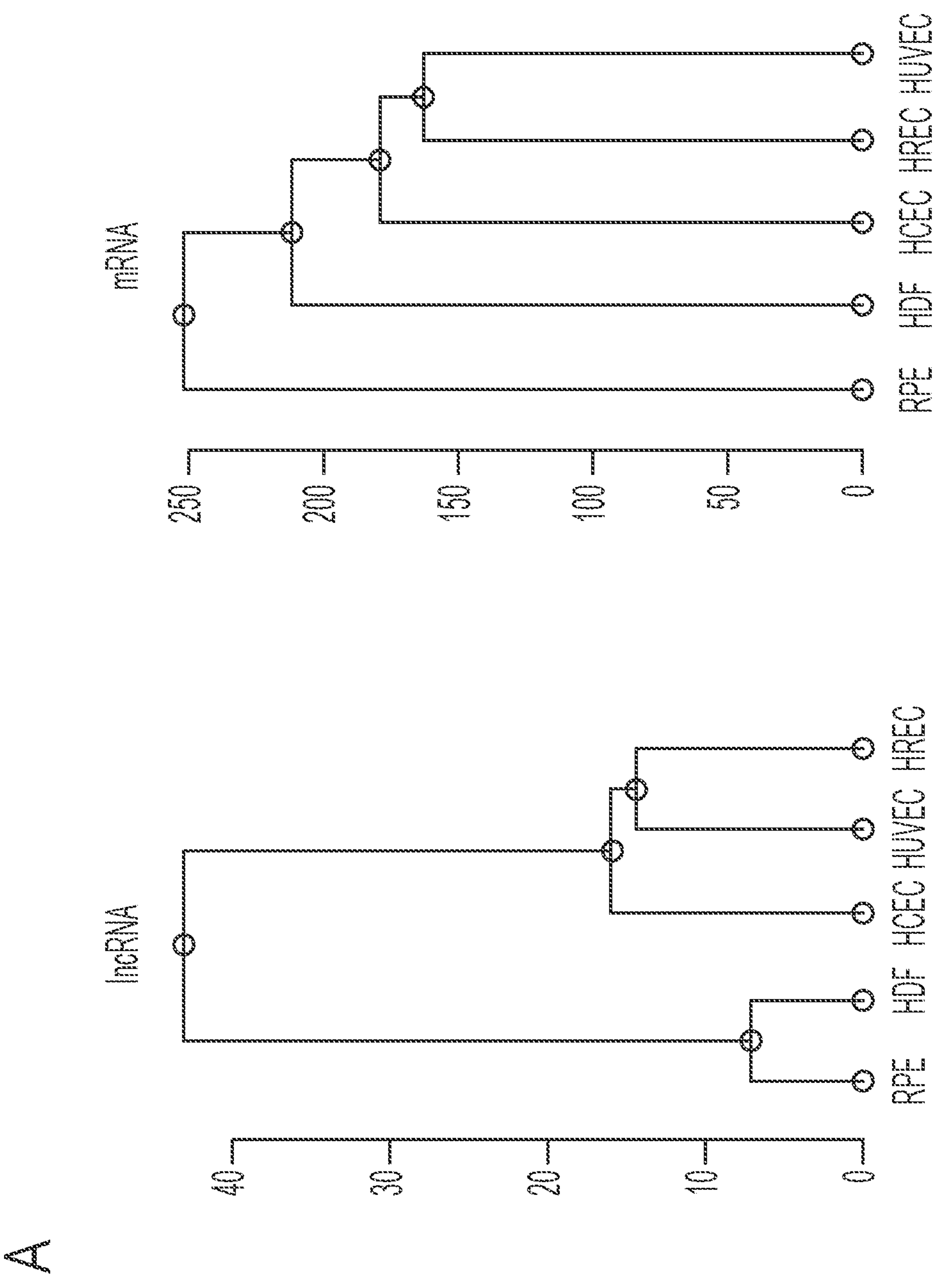

By profiling more than 30,000 lncRNAs in several primary human EC lines, the inventors have identified ~500 human EC-restricted lncRNAs. Among them, the inventors focused on lncEGFL7OS, which is located in the opposite strand of the EGFL7/miR-126 gene. Through a series of in vitro and in vivo experiments, the inventors established lncEGFL7OS as a disease-relevant, human/primate-specific, EC-enriched lncRNA that is critical for angiogenesis through regulating MAX transcription factor activity at the EGFL7/miR-126 locus. These and other aspects of the disclosure are set out in detail below.

I. LNCEGFL7OS

As described below, in an effort to identify potential angiogenesis-related lncRNAs, the inventors set up a screening for lncRNAs enriched in several EC lines compared to non-ECs. The inventors identified ~500 EC-enriched lncRNAs, one of which is lncEGFL7OS. This lncRNA is located in the antisense strand of the EGFL7/miR-126 gene. lncEGFL7OS is a human/primate-specific lncRNA and its expression is highly specific to ECs and vascularized tissues. The inventors found that silencing of lncEGFL7OS results in G1 arrest and represses both EC proliferation and migration. The requirement of lncEGFL7OS for angiogenesis is also demonstrated by impaired tube formation in Matrigel assay in vitro and in vivo and repressed vasculogenesis/angiogenesis in an EC/fibroblast co-culture assay upon lncEGFL7OS knockdown.

Moreover, the inventors have developed a human choroid sprouting assay system and found that silencing of lncEGFL7OS significantly represses human choroid sprouting ex vivo. Mechanistically, lncEGFL7OS functions as an enhancer lncRNA that regulates EGFL7/miR-126 expression in ECs through repressing DNA methylation in the EGFL7/miR-126 promoter. Taken together, the inventors have identified EC-enriched lncRNAs, including lncEGFL7OS that are critical for angiogenesis in humans. The present disclosure provides compositions and methods of treatment for therapeutics of vascular disorders in humans. Vascular disorders that can be treated with the present disclosure include tumor growth and metastasis associated with cancers, age-related macular degeneration (AMD), diabetic retinopathy, psoriasis, arthritis, ischemic heart disease, neurodegeneration, hypertension, respiratory distress, and atherosclerosis and other inflammatory diseases.

lncEGFL7OS is deposited as RP11-251M1.1. The sequence is as below:

(SEQ ID NO: 1)

```
TGGGCTCAGGCCCAGAGTGCCAGCTTTGCCCTATCCCATAGCCTGGAGCC
ACCACAGGAGGGGCACTCCACTCTCTTGGGCTCCTGGAGCCTCAGAGGCA
GAGCCAGCCGGGAGTGCAGGAGGGAGAACTTTCCTGTGGACGTCCTGTGT
TCTCCAGACGCAGAGAACCCTCATCAACCGAGGGGGAGGTCACTTCCGAA
TCCACAGATGGCGTGTGAGTGCATGGCGAGCGCCTCCAGGACACACTTAC
TGTTCCCTTGCTCTGGCCAGACGCCAGCCGGACCCTGTGTGTGCGCGCCG
TGCTGCTCTTTGCAGCTGCCTGCAAGGGGTTCCTGCGAAGACCAGCACCT
TGGGGAAGAGCCTGCGGCTGAACTTGAACTCGCAGCTACCTGAGTCAGAC
CTGTGCTTTTTCACCTCTACGGAAGATGTCAGAGCGTTTCCCTAGCAATG
TTTTAGAAGTTACTTCTGTCTGGAAAAAAATGGAAAAAATGGCAAATTAT
GTTATGTATAATTTGATAATTTTAAAGAATTAATGATGTAATTATTACTC
AAACCCA.
```

A. Evolution of lncEGFL7OS/EGFL7/miR-126 Locus

The evolution of EGFL7/miR-126 locus exemplifies the evolution of the vascular system. EGFL7 encodes an EGF-like domain containing protein that is specifically secreted by vascular ECs. It is conserved among vertebrates, but an orthologue is also found in *Drosophila melanogaster* (CG7447). miR-126 and miR-126* are encoded by the intron of EGFL7 and are conserved from Fugu in vertebrates to *Homo sapiens* 34. They are the only miRNAs that are known to be specifically in EC lineage and hematopoietic stem cells. Loss-of-function studies in mice and zebrafish revealed an important function of miR-126 in governing vascular integrity and angiogenesis. Egfl7−/− mice display similar vascular abnormalities to MiR126−/− mice, including edema, defective cranial vessel and retinal vascularization. However, an independent study suggests that the vascular phenotype of Egfl7−/− mice could be attributed to the MiR126 deletion (or downregulation) in the mice. The important regulatory function of miR-126 in vascular integrity and angiogenesis is correlated with its appearance during the evolution of vascular system in vertebrates. Besides, miR-126 also has documented functions in vascular inflammation, as well as innate and adaptive immunity. That also correlates with the evolutionary innovation of adaptive immune system in vertebrates. These support an important function of EGFL7/miR-126 locus from the evolutionary point of view. To further dissect the function and regulation of the locus during evolution from vertebrates to humans, the inventors identified lncEGFL7OS, which is located in the opposite strand neighboring the EGFL7/miR-126 gene. It only exists in humans and several other primates, including rhesus monkeys, but not in other lower vertebrate species including mice. Although they showed significant function of lncEGFL7OS in human angiogenesis, the full spectrum of lncEGFL7OS function remains to be established.

B. lncEGFL7OS is a Human/Primate-Specific EC-Restricted lncRNA Required for Proper Human Angiogenesis The expression of lncEGFL7OS is restricted to ECs and highly vascularized tissues, which is consistent with the expression of its host genes EGFL7 and miR-126. As to its regulatory mechanisms, the inventors found that both lncEGFL7OS and miR-126 are regulated by ETS1/2 factors in ECs through a bidirectional promoter. They found that lncEGFL7OS is required for proper angiogenesis in vitro by using EC-fibroblast co-culture vasculogenesis/angiogenesis assays. Conversely, overexpression of lncEGFL7OS enhances angiogenesis. Using a human choroid sprouting angiogenesis model the inventors developed, they further demonstrated that lncEGFL7OS is required for human sprouting angiogenesis. This study indicates that three different transcripts from the EGFL7/miR-126 locus, including lncEGFL7OS, EGFL7 and miR-126, have important functions in angiogenesis. EGFL7 and miR-126 have been previously shown to regulate angiogenesis. EGFL7 is essential for vascular tube formation during vasculogenesis in zebrafish. The importance of miR-126 in angiogenesis was demonstrated by loss-of-function studies in both mouse and zebrafish. Targeted deletion of miR-126 in mice or miR-126 knockdown in zebrafish resulted in loss of vascular integrity and defective angiogenesis, while overexpression of miR-126 regulates angiogenesis in a cell-type and strand-specific manner. It is intriguing that, in contrast to EGFL7 and miR-126, lncEGFL7OS represents a human/primate-specific mechanism in regulating angiogenesis, since lncEGFL7OS only exists in human and several other primates. New angiogenesis mechanism through lncEGF7OS has evolved during evolution, which underscores the importance and delicacy of EFGL7/miR-126 locus in angiogenesis. This study also highlights the importance of using human (and/or primate) system to study the mechanism of angiogenesis.

C. Mechanism of lncEGFL7OS Action

The inventors showed that the action of lncEGFL7OS reflects at least partially the regulation of expression of EGFL7 and miR-126. miR-126 has been shown to promote MAP kinase and PI3K signaling in response to VEGF and FGF by targeting negative regulators of these signaling pathways, including Spred-I and PIK3R2. Consistent with the downregulation of miR-126 by lncEGFL7OS silencing, the inventors found that the phosphorylation of ERK1/2 and AKT in response to VEGF is repressed by lncEGFL7OS silencing. Mechanistically, MAX transcription factor was identified as a lncEGFL7OS interaction protein required for lncEGFL7OS-regulated gene expression and angiogenesis in ECs. Under normal conditions, the lncEGFL7OS/MAX interaction is likely locus dependent since several other MAX target genes were not affected by lncEGFL7OS silencing. This is possibly due to the low expression of lncEGFL7OS. LncEGFL7OS enhances the transcription of EGFL7/miR-126 by binding to MAX protein that is recruited to the bidirectional 509 promoter/enhancer region in EGFL7/miR-126. MAX knockdown blunts the induction of miR-126 by lncEGFL7OS in ECs. MAX transcription factor has been shown to interact with MYC to control cell proliferation and cell death. MYC has been shown to stimulate histone acetylation and gene transcription by recruitment of cAMP-response element-binding protein (CBP) and p300. Based on the results showing interaction of MAX and p300, the enrichment of H3K27 acetylation by lncEGFL7OS likely result from the recruitment of CBP and P300 by MAX/MYC. Taken together, lncEGFL7OS acts in cis by interacting with MAX transcription factor to enhance H3K7 acetylation and promote EGFL7/miR-126 expression.

D. Therapeutic Implications

Identifying angiogenic mechanisms that are conserved to human is critical for developing therapeutics for human vascular disorders. These studies have demonstrated that lncEGFL7OS is a human/primate-specific lncRNA critical for human angiogenesis. This may be directly translatable for human diseases involving abnormal angiogenesis. The inventors' studies showed increased expression of both lncEGFL7OS and EGFL7/miR-126 in the heart of DCM patients. Although the causative role of lncEGFL7OS in DCM is still unclear, lncEGFL7OS upregulation may reflect the compensatory vascularization/angiogenesis in DCM. It would be intriguing to test whether manipulating the lncEGFL7OS/EGFL7/miR-126 axis has therapeutic benefits for DCM patients. AMD is the leading cause of blindness in the elderly, and choroidal neovascularization is a hallmark for wet AMD. Although anti-VEGF agents can markedly improve the clinical outcome of wet AMD, they have been unable to induce complete angiogenesis regression, and only 30-40% of individuals experienced vision improvement after treatment. The inventors developed a human choroid sprouting angiogenesis model and showed that silencing of lncEGFL7OS represses human choroid sprouting angiogenesis. It would be appealing to develop and test lncEGFL7OS-based therapy to treat choroidal neovascularization in wet AMD and other vascular disorders in the future. In this regard, the data that CRISPR-mediated targeting of EGLF7/miR-126/lncEGFL7OS locus inhibits angiogenesis could have therapeutic implications in angiogenesis-related diseases. Targeting this locus could be a potent approach for inhibiting angiogenesis than targeting the three genes individually.

E. Antagonists of lncEGFL7OS, EGFL7, and miR-126

Another approach to regulating lncEGFL7OS is through the design of CRISPR guide RNAs that target lncEGFL7OS genomic DNA, thereby silencing lncEGFL7OS expression. CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced eubacteria genomes and 90% of sequenced archaea. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

CRISPR was first shown to work as a genome engineering/editing tool in human cell culture by 2012 It has since been used in a wide range of organisms including baker's yeast (*S. cerevisiae*), zebra fish, nematodes (*C. elegans*), plants, mice, and several other organisms. Additionally, CRISPR has been modified to make programmable transcription factors that allow scientists to target and activate or silence specific genes. Libraries of tens of thousands of guide RNAs are now available.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apem, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype Ecoli) proteins (called CasA-E in *E. coli*) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in *E. coli* requires Cascade and Cas3, but not Cas1 and Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes.

See also U.S. Patent Publication 2014/0068797, which is incorporated by reference in its entirety.

Cas9 is a nuclease, an enzyme specialized for cutting DNA, with two active cutting sites, one for each strand of the double helix. The team demonstrated that they could disable one or both sites while preserving Cas9's ability to home located its target DNA. Jinek et al. (2012) combined tracrRNA and spacer RNA into a "single-guide RNA" molecule that, mixed with Cas9, could find and cut the correct DNA targets. Jinek and coworkers proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of *Francisella novicida* uses a unique, small, CRISPR/Cas-associated RNA (scaRNA) to repress an endogenous transcript encoding a bacterial lipoprotein that is critical for *F. novicida* to dampen host response and promote virulence. Wang et al. showed that coinjection of Cas9 mRNA and sgRNAs into the germline (zygotes) generated nice with mutations. Delivery of Cas9 DNA sequences also is contemplated.

Clustered Regularly Interspaced Short Palindromic Repeats from *Prevotella* and *Francisella* 1 or CRISPR/Cpf1 is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

As a RNA guided protein, Cas9 (and Cfp1 as well) requires a short RNA to direct the recognition of DNA targets (Mali et al., 2013a). Though Cas9 preferentially interrogates DNA sequences containing a PAM sequence NGG it can bind here without a protospacer target. However, the Cas9-gRNA complex requires a close match to the gRNA to create a double strand break (Cho et al., 2013; Hsu et al., 2013). CRISPR sequences in bacteria are expressed in multiple RNAs and then processed to create guide strands for RNA (Bikard et al., 2013). Because Eukaryotic systems lack some of the proteins required to process CRISPR RNAs the synthetic construct gRNA was created to combine the essential pieces of RNA for Cas9 targeting into a single RNA expressed with the RNA polymerase type III promoter U6 (Mali et al., 2013a, b). Synthetic gRNAs are slightly over 100 bp at the minimum length and contain a portion which is targets the 20 protospacer nucleotides immediately preceding the PAM sequence NGG; gRNAs do not contain a PAM sequence.

II. ANGIOGENESIS

Angiogenesis is the physiological process through which new blood vessels form from pre-existing vessels. In precise usage this is distinct from vasculogenesis, which is the de novo formation of endothelial cells from mesoderm cell precursors, and from neovascularization, although discussions are not always precise. The first vessels in the developing embryo form through vasculogenesis, after which angiogenesis is responsible for most, if not all, blood vessel growth during development and in disease.

Angiogenesis is a normal and vital process in growth and development, as well as in wound healing and in the formation of granulation tissue. However, it is also a fundamental step in the transition of tumors from a benign state to a malignant one, leading to the use of angiogenesis inhibitors in the treatment of cancer.

Angiogenesis may be a target for combating diseases characterized by either poor vascularization or abnormal vasculature. Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

The modern clinical application of the principle of angiogenesis can be divided into two main areas: anti-angiogenic therapies, which angiogenic research began with, and pro-angiogenic therapies. Whereas anti-angiogenic therapies are being employed to fight cancer and malignancies, which require an abundance of oxygen and nutrients to proliferate, pro-angiogenic therapies are being explored as options to treat cardiovascular diseases, the number one cause of death in the Western world. One of the first applications of pro-angiogenic methods in humans was a German trial using fibroblast growth factor 1 (FGF-1) for the treatment of coronary artery disease. Clinical research in therapeutic angiogenesis is ongoing for a variety of atherosclerotic diseases, like coronary heart disease, peripheral arterial disease, wound healing disorders, etc.

Also, regarding the mechanism of action, pro-angiogenic methods can be differentiated into three main categories: gene-therapy, targeting genes of interest for amplification or inhibition: protein-therapy, which primarily manipulates angiogenic growth factors like FGF-1 or vascular endothelial growth factor, VEGF; and cell-based therapies, which involve the implantation of specific cell types.

There are still serious, unsolved problems related to gene therapy. Difficulties include effective integration of the therapeutic genes into the genome of target cells, reducing the risk of an undesired immune response, potential toxicity, immunogenicity, inflammatory responses, and oncogenesis related to the viral vectors used in implanting genes and the sheer complexity of the genetic basis of angiogenesis. The most commonly occurring disorders in humans, such as heart disease, high blood pressure, diabetes and Alzheimer's disease, are most likely caused by the combined effects of variations in many genes, and, thus, injecting a single gene may not be significantly beneficial in such diseases.

In contrast, pro-angiogenic protein therapy uses well-defined, precisely structured proteins, with previously defined optimal doses of the individual protein for disease states, and with well-known biological effects. On the other hand, an obstacle of protein therapy is the mode of delivery. Oral, intravenous, intra-arterial, or intramuscular routes of protein administration are not always as effective, as the therapeutic protein may be metabolized or cleared before it can enter the target tissue. Cell-based pro-angiogenic therapies are still early stages of research, with many open questions regarding best cell types and dosages to use.

III. METHODS OF TREATING DISEASE STATES

The present disclosure provides methods of treating various disease states by administering to a subject agonists or antagonists of lncEGFL7OS, EGFL7, and miR-126. For the purposes of the present application, treatment comprises reducing one or more of the symptoms of associated with the disease states discussed below. Any level of improvement will be considered treatment, and there is no requirement for a particular level of improvement or a "cure." It is also sufficient in treatment that symptoms be stabilized, i.e., that the disease condition will not worsen.

The present disclosure provides a method of promoting vascular integrity and/or vascular repair comprising administering to a subject suffering from a vascular condition an agonist of lncEGFL7OS, EGFL7, and miR-126 function. The vascular condition may include, but is not limited to, myocardial infarction, ischemia-reperfusion injury, stenosis, fibrosis, vascular trauma, vascular leakage, psoriasis, arthritis, neurodegeneration, hypertension, and respiratory distress.

A. Conditions Impairing Vascular Integrity or Causing the Need for Vascular Repair As discussed above, the present disclosure provides for the use of agonists of lncEGFL7OS to improve the integrity of vascular tissue, and also to promote vascular repair and neovascularization following injury, including ischemic insults. The following disease states/conditions are specifically contemplated for treatment according to the present disclosure but are not limiting.

Treatment regimens would vary depending on the clinical situation. However, long-term maintenance would appear to be appropriate in most circumstances. It also may be desirable treat vascular conditions with modulators of lncEGFL7OS intermittently, such as within a brief window during disease progression.

Myocardial infarction. Myocardial infarction (MI), occurs when the blood supply to part of the heart is interrupted. This is most commonly due to occlusion (blockage) of a coronary artery following the rupture of a vulnerable atherosclerotic plaque, which is an unstable collection of lipids (like cholesterol) and white blood cells (especially macrophages) in the wall of an artery. The resulting ischemia (restriction in blood supply) and oxygen shortage, if left untreated for a sufficient period, can cause damage and/or death (infarction) of heart muscle tissue (myocardium).

Classical symptoms of acute myocardial infarction (AMI) include sudden chest pain (typically radiating to the left arm or left side of the neck), shortness of breath, nausea, vomiting, palpitations, sweating, and anxiety (often described as a sense of impending doom). Women may experience fewer typical symptoms than men, most commonly shortness of breath, weakness, a feeling of indigestion, and fatigue. Approximately one quarter of all myocardial infarctions are silent, without chest pain or other symptoms. A heart attack is a medical emergency, and people experiencing chest pain are advised to alert their emergency medical services, because prompt treatment is beneficial.

Immediate treatment for suspected acute myocardial infarction includes oxygen, aspirin, and sublingual glyceryl trinitrate (colloquially referred to as nitroglycerin and abbreviated as NTG or GTN). Pain relief is also often given, classically morphine sulfate. The patient will receive a number of diagnostic tests, such as an electrocardiogram (ECG, EKG), a chest X-ray and blood tests to detect elevations in cardiac markers (blood tests to detect heart muscle damage). The most often used markers are the creatine kinase-MB (CK-MB) fraction and the troponin I (TnI) or troponin T (TnT) levels. On the basis of the ECG, a distinction is made between ST elevation MI (STEMI) or non-ST elevation MI (NSTEMI). Most cases of STEMI are treated with thrombolysis or if possible with percutaneous coronary intervention (PCI, angioplasty and stent insertion), provided the hospital has facilities for coronary angiography. NSTEMI is managed with medication, although PCI is often performed during hospital admission. In patients who have multiple blockages and who are relatively stable, or in a few extraordinary emergency cases, bypass surgery of the blocked coronary artery is an option.

Ischemia-reperfusion injury. Ischemia-reperfusion injury is caused at least in part by the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

Glisodin, a dietary supplement derived from superoxide dismutase (SOD) and wheat gliadin, has been studied for its ability to mitigate ischemia-reperfusion injury. A study of aortic cross-clamping, a common procedure in cardiac surgery, demonstrated a strong potential benefit with further research ongoing.

Stenosis. A stenosis is an abnormal narrowing in a blood vessel or other tubular organ or structure. Stenoses of the vascular type are often associated with a noise (bruit) resulting from turbulent flow over the narrowed blood vessel. This bruit can be made audible by a stethoscope. Other, more reliable methods of diagnosing a stenosis are imaging methods including ultrasound, Magnetic Resonance Imaging/Magnetic Resonance Angiography, Computed Tomography/CT-Angiography which combine anatomic imaging (i.e., the visible narrowing of a vessel) with the display of flow phenomena (visualization of the movement of the bodily fluid through the bodily structure). Vascular stenoses include intermittent claudication (peripheral artery stenosis), angina (coronary artery stenosis), carotid artery stenosis which predispose to (strokes and transient ischemic episodes) and renal artery stenosis.

Other Conditions. Trauma and vascular leakage are also conditions which may be treated with lncEGFL7OS or agonists thereof.

Risks. The present disclosure also contemplates treating individuals at risk for any of the aforementioned disease states. These individuals would include those persons suffering from fibrosis, hypertension, cardiac hypertrophy, osteoporosis, neurodegeneration, and/or respiratory distress.

B. Pathologic Neovascularization

As discussed above, the present disclosure provides for the use of antagonists of lncEGFL7OS to impede neovasculariziation that leads to or contributes to disease. The following disease states/conditions are specifically contemplated for treatment according to the present disclosure but are not limiting.

The present disclosure provides a method of inhibiting pathologic vascularization in a subject in need thereof comprising administering to a subject an antagonist of lncEGFL7OS, EGFL7, and miR-126. A condition associated with pathologic vascularization includes, but is not limited to, atherosclerosis, retinopathy, cancer, and stroke.

Early Stage Atherosclerosis. Atherosclerosis is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high-density lipoproteins (HDL). It is commonly referred to as a "hardening" of the arteries. It is caused by the formation of multiple plaques within the arteries.

Atherosclerosis develops from low-density lipoprotein cholesterol (LDL), colloquially called "bad cholesterol." When this lipoprotein gets through the wall of an artery, oxygen free radicals react with it to form oxidized-LDL. The body's immune system responds by sending specialized white blood cells (macrophages and T-lymphocytes) to absorb the oxidized-LDL. Unfortunately, these white blood cells are not able to process the oxidized-LDL, and ultimately grow then rupture, depositing a greater amount of oxidized cholesterol into the artery wall. This triggers more white blood cells, continuing the cycle. Eventually, the artery becomes inflamed. The cholesterol plaque causes the muscle cells to enlarge and form a hard cover over the affected area. This hard cover is what causes a narrowing of the artery, reduces the blood flow and increases blood pressure.

Atherosclerosis typically begins in early adolescence, and is usually found in most major arteries, yet is asymptomatic and not detected by most diagnostic methods during life. The stage immediately prior to actual atherosclerosis is known as subclinical atherosclerosis. It most commonly becomes seriously symptomatic when interfering with the coronary circulation supplying the heart or cerebral circulation supplying the brain and is considered the most important underlying cause of strokes, heart attacks, various heart diseases including congestive heart failure, and most cardiovascular diseases, in general. Atheroma in arm, or more often in leg arteries, which produces decreased blood flow is called Peripheral artery occlusive disease (PAOD). Most artery flow disrupting events occur at locations with less than 50% lumen narrowing (~20% stenosis is average).

Although the disease process tends to be slowly progressive over decades, it usually remains asymptomatic until an atheroma obstructs the bloodstream in the artery. This is typically by rupture of an atheroma, clotting and fibrous organization of the clot within the lumen, covering the rupture but also producing stenosis, or over time and after repeated ruptures, resulting in a persistent, usually localized stenosis. Stenoses can be slowly progressive, whereas plaque rupture is a sudden event that occurs specifically in atheromas with thinner/weaker fibrous caps that have become "unstable."

Repeated plaque ruptures, ones not resulting in total lumen closure, combined with the clot patch over the rupture and healing response to stabilize the clot, is the process that produces most stenoses over time. The stenotic areas tend to become more stable, despite increased flow velocities at these narrowings. Most major blood-flow-stopping events occur at large plaques, which, prior to their rupture, produced very little if any stenosis.

From clinical trials, 20% is the average stenosis at plaques that subsequently rupture with resulting complete artery closure. Most severe clinical events do not occur at plaques that produce high-grade stenosis. From clinical trials, only 14% of heart attacks occur from artery closure at plaques producing a 75% or greater stenosis prior to the vessel closing.

If the fibrous cap separating a soft atheroma from the bloodstream within the artery ruptures, tissue fragments are exposed and released, and blood enters the atheroma within the wall and sometimes results in a sudden expansion of the atheroma size. Tissue fragments are very clot-promoting, containing collagen and tissue factor; they activate platelets and activate the system of coagulation. The result is the formation of a thrombus (blood clot) overlying the atheroma, which obstructs blood flow acutely. With the obstruction of blood flow, downstream tissues are starved of oxygen and nutrients. If this is the myocardium (heart muscle), angina (cardiac chest pain) or myocardial infarction (heart attack) develops.

If atherosclerosis leads to symptoms, some symptoms such as angina pectoris can be treated. Non-pharmaceutical means are usually the first method of treatment, such as cessation of smoking and practicing regular exercise. If these methods do not work, medicines are usually the next step in treating cardiovascular diseases, and, with improvements, have increasingly become the most effective method over the long term. However, medicines are criticized for their expense, patented control and occasional undesired effects.

In general, the group of medications referred to as statins has been the most popular and are widely prescribed for treating atherosclerosis. They have relatively few short-term or longer-term undesirable side-effects, and multiple comparative treatment/placebo trials have fairly consistently shown strong effects in reducing atherosclerotic disease 'events' and generally ~-25% comparative mortality reduction in clinical trials, although one study design, ALLHAT, was less strongly favorable.

The newest statin, rosuvastatin, has been the first to demonstrate regression of atherosclerotic plaque within the coronary arteries by IVUS (intravascular ultrasound evaluation). The study was set up to demonstrate effect primarily on atherosclerosis volume within a 2 year time-frame in people with active/symptomatic disease (angina frequency also declined markedly) but not global clinical outcomes, which was expected to require longer trial time periods; these longer trials remain in progress.

However, for most people, changing their physiologic behaviors, from the usual high risk to greatly reduced risk, requires a combination of several compounds, taken on a daily basis and indefinitely. More and more human treatment trials have been done and are ongoing that demonstrate improved outcome for those people using more-complex and effective treatment regimens that change physiologic behavior patterns to more closely resemble those that humans exhibit in childhood at a time before fatty streaks begin forming.

Retinopathy. Retinopathy is a general term that refers to some form of non-inflammatory damage to the retina of the eye. Most commonly it is a problem with the blood supply that is the cause for this condition. Frequently, retinopathy is an ocular manifestation of systemic disease. Retinopathy is diagnosed by an optometrist or an ophthalmologist during ophthalmoscopy. Treatment depends on the cause of the disease.

The main causes of retinopathy are diabetes—diabetic retinopathy; arterial hypertension—hypertensive retinopathy; prematurity of the newborn—retinopathy of prematurity (ROP); sickle cell anemia; genetic retinopathy; direct sunlight exposure—solar retinopathy; medicinal products—drug-related retinopathy; and retinal vein or artery occlusion. Many types of retinopathy are progressive and may result in blindness or severe vision loss or impairment, particularly if the macula becomes affected.

Age-Related Macular Degeneration. Macular degeneration, also known as age-related macular degeneration (AMD or ARMD), is a medical condition which may result in blurred or no vision in the center of the visual field. Early on there are often no symptoms. Over time, however, some people experience a gradual worsening of vision that may affect one or both eyes. While it does not result in complete blindness, loss of central vision can make it hard to recognize faces, drive, read, or perform other activities of daily life. Visual hallucinations may also occur but these do not represent a mental illness.

Macular degeneration typically occurs in older people. Genetic factors and smoking also play a role. It is due to damage to the macula of the retina. Diagnosis is by a complete eye exam. The severity is divided into early, intermediate, and late types. The late type is additionally divided into "dry" and "wet" forms with the dry form making up 90% of cases.

Prevention includes exercising, eating well, and not smoking. Antioxidant vitamins and minerals do not appear to be useful for prevention. There is no cure or treatment that returns vision already lost. In the wet form, anti-VEGF medication injected into the eye or less commonly laser coagulation or photodynamic therapy may slow worsening. Supplements in those who already have the disease may slow progression.

In 2010 it affected 23.5 million people globally. In 2013 moderate to severe disease affected 13.4 million and it is the fourth most common cause of blindness after cataracts, preterm birth, and glaucoma. It most commonly occurs in people over the age of fifty and in the United States is the most common cause of vision loss in this age group. About 0.4% of people between 50 and 60 have the disease, while it occurs in 0.7% of people 60 to 70, 2.3% of those 70 to 80, and nearly 12% of people over 80 years old.

Signs and symptoms of macular degeneration include (a) distorted vision in the form of metamorphopsia, in which a grid of straight lines appears wavy and parts of the grid may appear blank; Patients often first notice this when looking at things like miniblinds in their home or telephone poles while driving. There may also be central scotomas, shadows or missing areas of vision: (b) slow recovery of visual function after exposure to bright light (photostress test); (c) visual acuity drastically decreasing (two levels or more), e.g., 20/20 to 20/80; (d) blurred vision: Those with nonexudative macular degeneration may be asymptomatic or notice a gradual loss of central vision, whereas those with exudative macular degeneration often notice a rapid onset of vision loss (often caused by leakage and bleeding of abnormal blood vessels); (e) trouble discerning colors, specifically dark ones from dark ones and light ones from light ones; (f) a loss in contrast sensitivity.

Macular degeneration by itself will not lead to total blindness. For that matter, only a very small number of people with visual impairment are totally blind. In almost all cases, some vision remains, mainly peripheral. Other complicating conditions may possibly lead to such an acute condition (severe stroke or trauma, untreated glaucoma, etc.), but few macular degeneration patients experience total visual loss.

The area of the macula comprises only about 2.1% of the retina, and the remaining 97.9% (the peripheral field) remains unaffected by the disease. Even though the macula provides such a small fraction of the visual field, almost half of the visual cortex is devoted to processing macular information.

The loss of central vision profoundly affects visual functioning. It is quite difficult, for example, to read without central vision. Pictures that attempt to depict the central visual loss of macular degeneration with a black spot do not really do justice to the devastating nature of the visual loss. This can be demonstrated by printing letters six inches high on a piece of paper and attempting to identify them while looking straight ahead and holding the paper slightly to the side. Most people find this difficult to do.

The pathogenesis of age-related macular degeneration is not well known, although a number of theories have been put forward, including oxidative stress, mitochondrial dysfunction, and inflammatory processes.

The imbalance between production of damaged cellular components and degradation leads to the accumulation of detrimental products, for example, intracellular lipofuscin and extracellular drusen. Incipient atrophy is demarcated by areas of retinal pigment epithelium (RPE) thinning or depigmentation that precede geographic atrophy in the early stages of AMD. In advanced stages of AMD, atrophy of the RPE (geographic atrophy) and/or development of new blood vessels (neovascularization) result in death of photoreceptors and central vision loss.

In the dry (nonexudative) form, cellular debris called drusen accumulates between the retina and the choroid, causing atrophy and scarring to the retina. In the wet (exudative) form, which is more severe, blood vessels grow up from the choroid (neovascularization) behind the retina which can leak exudate and fluid and also cause hemorrhaging.

Early work demonstrated a family of immune mediators was plentiful in drusen[1] Complement factor H (CFH) is an important inhibitor of this inflammatory cascade, and a disease-associated polymorphism in the CFH gene strongly associates with AMD. Thus, an AMD pathophysiological model of chronic low-grade complement activation and inflammation in the macula has been advanced. Lending credibility to this has been the discovery of disease-associated genetic polymorphisms in other elements of the complement cascade including complement component 3 (C3).

A powerful predictor of AMD is found on chromosome 10q26 at LOC 387715. An insertion/deletion polymorphism at this site reduces expression of the ARMS2 gene though destabilization of its mRNA through deletion of the polyadenylation signal. ARMS2 protein may localize to the mitochondria and participate in energy metabolism, though much remains to be discovered about its function. Other gene markers of progression risk include tissue inhibitor of metalloproteinase 3 (TIMP3), suggesting a role for intracellular matrix metabolism in AMD progression. Variations in cholesterol metabolizing genes such as the hepatic lipase, cholesterol ester transferase, lipoprotein lipase and the ABC-binding cassette A1 correlate with disease progression. The early stigmata of disease, drusen, are rich in cholesterol, offering face validity to the results of genome-wide association studies.

Diagnosis of age-related macular degeneration rests on signs in the macula, irrespective of visual acuity. Diagnosis of AMD may include the following procedures and tests. The transition from dry to wet AMD can happen rapidly, and if it is left untreated can lead to legal blindness in as little as six months. To prevent this from occurring and to initiate preventative strategies earlier in the disease process, dark adaptation testing may be performed. A dark adaptometer can detect subclinical AMD at least three years earlier than it is clinically evident.

There is a loss of contrast sensitivity, so that contours, shadows, and color vision are less vivid. The loss in contrast sensitivity can be quickly and easily measured by a contrast sensitivity test like Pelli Robson performed either at home or by an eye specialist. When viewing an Amsler grid, some straight lines appear wavy and some patches appear blank. When viewing a Snellen chart, at least 2 lines decline.

In dry macular degeneration, which occurs in 85-90 percent of AMD cases, drusen spots can be seen in Fundus photography. In wet macular degeneration, angiography can visualize the leakage of bloodstream behind the macula. Fluorescein angiography allows for the identification and localization of abnormal vascular processes. Using an electroretinogram, points in the macula with a weak or absent response compared to a normal eye may be found Famsworth-Munsell 100 hue test and Maximum Color Contrast Sensitivity test (MCCS) for assessing color acuity and color contrast sensitivity. Optical coherence tomography is now used by most ophthalmologists in the diagnosis and the follow-up evaluation of the response to treatment with antiangiogenic drugs.

In addition to the pigmented cells in the iris (the colored part of the eye), there are pigmented cells beneath the retina. As these cells break down and release their pigment, dark clumps of released pigment and later, areas that are less pigmented may appear. Exudative changes (hemorrhages in the eye, hard exudates, subretinal/sub-RPE % intraretinal fluid) and drusen, tiny accumulations of extracellular material that build up on the retina, also occur. While there is a tendency for drusen to be blamed for the progressive loss of vision, drusen deposits can be present in the retina without vision loss. Some patients with large deposits of drusen have normal visual acuity. If normal retinal reception and image transmission are sometimes possible in a retina when high concentrations of drusen are present, then, even if drusen can be implicated in the loss of visual function, there must be at least one other factor that accounts for the loss of vision.

Stroke. Stroke is the rapidly developing loss of brain functions due to a disturbance in the blood vessels supplying blood to the brain. This can be due to ischemia (lack of blood supply) caused by thrombosis or embolism, or due to a hemorrhage. It can cause permanent neurological damage, complications and death if not promptly diagnosed and treated. Risk factors for stroke include advanced age, hypertension (high blood pressure), previous stroke or transient ischemic attack (TIA), diabetes, high cholesterol, cigarette smoking, atrial fibrillation, estrogen-containing forms of hormonal contraception, migraine with aura, and thrombophilia (a tendency to thrombosis), patent foramen ovale and several rarer disorders. High blood pressure is the most important modifiable risk factor of stroke.

The traditional definition of stroke, devised by the World Health Organization in the 1970s, is a "neurological deficit of cerebrovascular cause that persists beyond 24 hours or is interrupted by death within 24 hours." The 24-hour limit divides stroke from transient ischemic attack, which is a related syndrome of stroke symptoms that resolve completely within 24 hours. With the availability of treatments that, when given early, can reduce stroke severity, many now prefer alternative concepts, such as brain attack and acute ischemic cerebrovascular syndrome (modeled after heart attack and acute coronary syndrome respectively), that reflect the urgency of stroke symptoms and the need to act swiftly.

Stroke is occasionally treated with thrombolysis ("clot-buster"), but usually with supportive care (physiotherapy and occupational therapy) and secondary prevention with antiplatelet drugs (aspirin and often dipyridamole), blood pressure control, statins and anticoagulation (in selected patients).

Strokes can be classified into two major categories: ischemic and hemorrhagic. Ischemia is due to interruption of the blood supply, while hemorrhage is due to rupture of a blood vessel or an abnormal vascular structure. 80% of strokes are due to ischemia; the remainder are due to hemorrhage.

In an ischemic stroke, blood supply to part of the brain is decreased, leading to dysfunction and necrosis of the brain tissue in that area. There are four reasons why this might happen: thrombosis (obstruction of a blood vessel by a blood clot forming locally), embolism (idem due to an embolus from elsewhere in the body, see below), systemic hypoperfusion (general decrease in blood supply, e.g., in shock) and venous thrombosis. Stroke without an obvious explanation is termed "cryptogenic" (of unknown origin).

In thrombotic stroke, a thrombus (blood clot) usually forms around atherosclerotic plaques. Since blockage of the artery is gradual, onset of symptomatic thrombotic strokes is slower. A thrombus itself (even if non-occluding) can lead to an embolic stroke (see below) if the thrombus breaks off at which point it is called an "embolus." Thrombotic stroke can be divided into two types depending on the type of vessel the thrombus is formed on—large vessel disease or small vessel disease.

Embolic stroke refers to the blockage of an artery by an embolus, a traveling particle or debris in the arterial bloodstream originating from elsewhere. An embolus is most frequently a thrombus, but it can also be a number of other substances including fat (e.g. from bone marrow in a broken bone), air, cancer cells or clumps of bacteria (usually from infectious endocarditis). Because an embolus arises from elsewhere, local therapy only solves the problem temporarily. Thus, the source of the embolus must be identified. Because the embolic blockage is sudden in onset, symptoms usually are maximal at start. Also, symptoms may be transient as the embolus is partially resorbed and moves to a different location or dissipates altogether. Emboli most commonly arise from the heart (especially in atrial fibrillation) but may originate from elsewhere in the arterial tree. In paradoxical embolism, a deep vein thrombosis embolizes through an atrial or ventricular septal defect in the heart into the brain.

Cardiac causes can be distinguished between high- and low-risk:

High risk: atrial fibrillation and paroxysmal atrial fibrillation, rheumatic disease of the mitral or aortic valve disease, artificial heart valves, known cardiac thrombus of the atrium or vertricle, sick sinus syndrome, sustained atrial flutter, recent myocardial infarction, chronic myocardial infarction together with ejection fraction <28 percent, symptomatic congestive heart failure with ejection fraction <30 percent, dilated cardiomyopathy, Libman-Sacks endocarditis, Marantic endocarditis, infective endocarditis, papillary fibroelastoma, left atrial myxoma and coronary artery bypass graft (CABG) surgery.

Low risk/potential: calcification of the annulus (ring) of the mitral valve, patent foramen ovale (PFO), atrial septal aneurysm, atrial septal aneurysm with patent foramen ovale, left ventricular aneurysm without thrombus, isolated left atrial "smoke" on echocardiography (no mitral stenosis or atrial fibrillation), complex atheroma in the ascending aorta or proximal arch.

Systemic hypoperfusion is the reduction of blood flow to all parts of the body. It is most commonly due to cardiac pump failure from cardiac arrest or arrhythmias, or from reduced cardiac output as a result of myocardial infarction, pulmonary embolism, pericardial effusion, or bleeding. Hypoxemia (low blood oxygen content) may precipitate the hypoperfusion. Because the reduction in blood flow is global, all parts of the brain may be affected, especially "watershed" areas—border zone regions supplied by the major cerebral arteries. Blood flow to these areas does not necessarily stop, but instead it may lessen to the point where brain damage can occur. This phenomenon is also referred to as "last meadow" to point to the fact that in irrigation the last meadow receives the least amount of water.

Cerebral venous sinus thrombosis leads to stroke due to locally increased venous pressure, which exceeds the pressure generated by the arteries. Infarcts are more likely to undergo hemorrhagic transformation (leaking of blood into the damaged area) than other types of ischemic stroke.

An ischemic stroke is due to a thrombus (blood clot) occluding a cerebral artery, a patient is given antiplatelet medication (aspirin, clopidogrel, dipyridamole), or anticoagulant medication (warfarin), dependent on the cause, when this type of stroke has been found.

Hemorrhagic stroke must be ruled out with medical imaging, since this therapy would be harmful to patients with that type of stroke.

Other immediate strategies to protect the brain during stroke include ensuring that blood sugar is as normal as possible (such as commencement of an insulin sliding scale in known diabetics), and that the stroke patient is receiving adequate oxygen and intravenous fluids. The patient may be positioned so that his or her head is flat on the stretcher, rather than sitting up, since studies have shown that this increases blood flow to the brain. Additional therapies for ischemic stroke include aspirin (50 to 325 mg daily), clopidogrel (75 mg daily), and combined aspirin and dipyridamole extended release (25/200 mg twice daily).

It is common for the blood pressure to be elevated immediately following a stroke. Studies indicated that while high blood pressure causes stroke, it is actually beneficial in the emergency period to allow better blood flow to the brain.

If studies show carotid stenosis, and the patient has residual function in the affected side, carotid endarterectomy (surgical removal of the stenosis) may decrease the risk of recurrence if performed rapidly after stroke.

If the stroke has been the result of cardiac arrhythmia with cardiogenic emboli, treatment of the arrhythmia and anticoagulation with warfarin or high-dose aspirin may decrease the risk of recurrence. Stroke prevention treatment for a common arrhythmia, atrial fibrillation, is determined according to the CHADS/CHADS2 system.

In increasing numbers of primary stroke centers, pharmacologic thrombolysis ("clot busting") with the drug tissue plasminogen activator (tPA), is used to dissolve the clot and unblock the artery. However, the use of tPA in acute stroke is controversial. Another intervention for acute ischemic stroke is removal of the offending thrombus directly. This is accomplished by inserting a catheter into the femoral artery, directing it into the cerebral circulation, and deploying a corkscrew-like device to ensnare the clot, which is then withdrawn from the body. Anticoagulation can prevent recurrent stroke. Among patients with nonvalvular atrial fibrillation, anticoagulation can reduce stroke by 60% while antiplatelet agents can reduce stroke by 20%. However, a recent meta-analysis suggests harm from anti-coagulation started early after an embolic stroke.

Cancer. Cancers comprise a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not. The branch of medicine concerned with the study, diagnosis, treatment, and prevention of cancer is oncology.

Nearly all cancers are caused by abnormalities in the genetic material of the transformed cells. These abnormalities may be due to the effects of carcinogens, such as tobacco smoke, radiation, chemicals, or infectious agents. Other cancer-promoting genetic abnormalities may be randomly acquired through errors in DNA replication, or are inherited, and thus present in all cells from birth. The heritability of cancers is usually affected by complex interactions between carcinogens and the host's genome. New aspects of the genetics of cancer pathogenesis, such as DNA methylation, and microRNAs are increasingly recognized as important.

Diagnosis usually requires the histologic examination of a tissue biopsy specimen by a pathologist, although the initial indication of malignancy can be symptoms or radiographic imaging abnormalities. Most cancers can be treated and some cured, depending on the specific type, location, and stage. Once diagnosed, cancer is usually treated with a combination of surgery, chemotherapy and radiotherapy.

Radiation therapy (also called radiotherapy, X-ray therapy, or irradiation) is the use of ionizing radiation to kill cancer cells and shrink tumors. Radiation therapy can be administered externally via external beam radiotherapy (EBRT) or internally via brachytherapy. Radiation therapy may be used to treat almost every type of solid tumor, including cancers of the brain, breast, cervix, larynx, lung, pancreas, prostate, skin, stomach, uterus, or soft tissue sarcomas. Radiation is also used to treat leukemia and lymphoma. Radiation dose to each site depends on a number of factors, including the radiosensitivity of each cancer type and whether there are tissues and organs nearby that may be damaged by radiation. Thus, as with every form of treatment, radiation therapy is not without its side effects.

Chemotherapy is the treatment of cancer with drugs that can destroy cancer cells. In current usage, the term "chemotherapy" usually refers to cytotoxic drugs which affect rapidly dividing cells in general, in contrast with targeted therapy (see below). Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can. Hence, chemotherapy has the potential to harm healthy tissue, especially those tissues that have a high replacement rate (e.g., intestinal lining). These cells usually repair themselves after chemotherapy. Because some drugs work better together than alone, two or more drugs are often given at the same time. This is called "combination chemotherapy." and indeed, most chemotherapy regimens are given in a combination.

Targeted therapy, which first became available in the late 1990's, has had a significant impact in the treatment of some types of cancer, and is currently a very active research area. This constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors imatinib and gefitinib.

Monoclonal antibody therapy is another strategy in which the therapeutic agent is an antibody which specifically binds to a protein on the surface of the cancer cells. Examples include the anti-HER2/neu antibody trastuzumab (Herceptin) used in breast cancer, and the anti-CD20 antibody rituximab, used in a variety of B-cell malignancies.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. Especially oligo- or multimers of these binding motifs are of great interest, since this can lead to enhanced tumor specificity and avidity.

Photodynamic therapy (PDT) is a ternary treatment for cancer involving a photosensitizer, tissue oxygen, and light (often using lasers). PDT can be used as treatment for basal cell carcinoma (BCC) or lung cancer; PDT can also be useful in removing traces of malignant tissue after surgical removal of large tumors.

Cancer immunotherapy refers to a diverse set of therapeutic strategies designed to induce the patient's own immune system to fight the tumor. Contemporary methods for generating an immune response against tumors include intravesical BCG immunotherapy for superficial bladder cancer and use of interferons and other cytokines to induce an immune response in renal cell carcinoma and melanoma patients. Vaccines to generate specific immune responses are the subject of intensive research for a number of tumors, notably malignant melanoma and renal cell carcinoma. Sipuleucel-T is a vaccine-like strategy in late clinical trials for prostate cancer in which dendritic cells from the patient are loaded with prostatic acid phosphatase peptides to induce a specific immune response against prostate-derived cells.

Allogeneic hematopoietic stem cell transplantation ("bone marrow transplantation" from a genetically non-identical donor) can be considered a form of immunotherapy, since the donor's immune cells will often attack the tumor in a phenomenon known as graft-versus-tumor effect. For this reason, allogeneic HSCT leads to a higher cure rate than autologous transplantation for several cancer types, although the side effects are also more severe.

The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

Angiogenesis inhibitors prevent the extensive growth of blood vessels (angiogenesis) that tumors require to survive. Some, such as bevacizumab, have been approved and are in clinical use. One of the main problems with anti-angiogenesis drugs is that many factors stimulate blood vessel growth, in normal cells and cancer. Anti-angiogenesis drugs only target one factor, so the other factors continue to stimulate blood vessel growth. Other problems include route of administration, maintenance of stability and activity and targeting at the tumor vasculature.

Risk. The present disclosure also contemplates treating individuals at risk for any of the aforementioned disease states. These individuals would include those persons suffering from atherosclerosis, obesity, asthma, arthritis, psoriasis and/or blindness.

C. Combined Therapy

In another embodiment, it is envisioned to use a modulator of lncEGFL7OS in combination with other therapeutic modalities. Thus, in addition to the therapies described above, one may also provide to the patient more "standard" pharmaceutical therapies. Combinations may be achieved by contacting cells, tissues or subjects with a single composition or pharmacological formulation that includes both agents, or by contacting the cell with two distinct compositions or formulations, at the same time, wherein one composition includes the expression construct and the other includes the agent. Alternatively, the therapy using a modulator of lncEGFL7OS may precede or follow administration of the other agent(s) by intervals ranging from minutes to weeks. In embodiments where the other agent and expression construct are applied separately to the cell, one would generally ensure that a significant period of time did not expire between each delivery, such that the agent and expression construct would still be able to exert an advantageously combined effect on the cell, tissue or subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a modulator of lncEGFL7OS, or the other agent will be desired. In this regard, various combinations may be employed. By way of illustration, where the modulator of lncEGFL7OS is "A" and the other agent is "B," the following permutations based on 3 and 4 total administrations are exemplary:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are likewise contemplated.

D. Pharmacological Therapeutic Agents

Pharmacological therapeutic agents and methods of administration, dosages, etc., are well known to those of skill in the art (see for example, the "Physicians' Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the disclosure in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present disclosure include an anti-hyperlipoproteinemic agent, an anti-arteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. Also contemplated for combination with an lncEGFL7OS modulator are any of the agents/therapies discussed in Sections IIIA-B, above.

E. Regulation of Therapies

The present disclosure also contemplates methods for scavenging or clearing lncEGFL7OS agonists or antagonists following treatment. The method may comprise overexpressing binding sites for the lncEGFL7OS antagonists in target tissues. In another embodiment, the present disclosure provides a method for scavenging or clearing lncEGFL7OS following treatment. In one embodiment, the method comprises overexpression of binding site regions for lncEGFL7OS in target tissues. The binding site regions preferably contain a binding sequence for lncEGFL7OS. In some embodiments, the binding site may contain a sequence from one or more targets of lncEGFL7OS, such as miR-126. In another embodiment, a lncEGFL7OS antagonist may be administered after lncEGFL7OS to attenuate or stop the function of the lncRNA. In another embodiment, overexpression or silencing of the lncEGFL7OS regulative genes, including ETS1, ETS2 and MAX, can be used to modulate the function of lncEGFL7OS.

F. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector or cells, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the externporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial or antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present disclosure generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. KITS

Any of the compositions described herein may be comprised in a kit. In a non-limiting example, an individual sgRNA modulator (e.g., sgRNA, expression construct) is included in a kit. The kit may further include water and hybridization buffer to facilitate hybridization to the lncRNAs. The kit may also include one or more transfection reagent(s) to facilitate delivery of the lncRNA to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present disclosure will also typically include a means for containing the vials in close confinement for commercial sale, such as, e.g., injection and/or blow-molded plastic containers into which the desired vials are retained.

Such kits may also include components that preserve or maintain the lncRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

It is contemplated that such reagents are embodiments of kits of the disclosure. Such kits, however, are not limited to the particular items identified above and may include any reagent used for the manipulation or characterization of lncRNA.

V. SCREENING METHODS

The present disclosure further comprises methods for identifying modulators of lncEGFL7OS that are useful in the prevention or treatment of the diseases discussed above. These assays may comprise random screening of large libraries of candidate substances; alternatively, the assays may be used to focus on particular classes of compounds selected with an eye towards structural attributes that are believed to make them more likely to modulate the expression and/or function of lncEGFL7OS.

To identify a modulator of lncEGFL7OS, one generally will determine the function of a lncEGFL7OS in the presence and absence of the candidate substance. For example, a method generally comprises:

(a) providing a candidate modulator:
(b) admixing the candidate modulator with a lncEGFL7OS;
(c) measuring lncEGFL7OS activity; and
(d) comparing the activity in step (c) with the activity in the absence of the candidate modulator, wherein a difference between the measured activities indicates that the candidate modulator is, indeed, a modulator of lncEGFL7OS. Assays also may be conducted in isolated cells, organs, or in living organisms.

It will, of course, be understood that all the screening methods of the present disclosure are useful in themselves notwithstanding the fact that effective candidates may not be found. The disclosure provides methods for screening for such candidates, not solely methods of finding them.

A. Modulators

As used herein the term "candidate substance" refers to any molecule that may potentially modulate angiogenic-regulating aspects of lncEGFL7OS. One will typically acquire, from various commercial sources, molecular libraries that are believed to meet the basic criteria for useful drugs in an effort to "brute force" the identification of useful compounds. Screening of such libraries, including combinatorially-generated libraries (e.g., compound libraries), is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564. Large numbers of small nucleic acids may be synthesized on a solid substrate, such as plastic pins or some other surface. Such molecules can be rapidly screening for their ability to inhibit lncEGFL7OS.

C. In Cyto Assays

The present disclosure also contemplates the screening of compounds for their ability to modulate lncEGFL7OS activity and expression in cells. Various cell lines, including those derived from endothelial cells and hematopoietic cells, can be utilized for such screening assays, including cells specifically engineered for this purpose.

D. In Vivo Assays

In vivo assays involve the use of various animal models of vascular diseases, discussed above, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria. Also, measuring toxicity and dose response can be performed in animals in a more meaningful fashion than in in vitro or in cyto assays.

VI. VECTORS FOR CLONING, GENE TRANSFER AND EXPRESSION

Within certain embodiments expression vectors are employed to express agonists or antagonists of lncEGFL7OS, EGFL7, and miR-126. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" is meant to include any type of genetic construct containing a nucleic acid coding for a gene product in which part or all of the nucleic acid encoding sequence is capable of being transcribed. Generally, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present disclosure, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance: this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |

TABLE 1-continued

| Promoter and/or Enhancer | |
|---|---|
| Promoter/Enhancer | References |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | ElA | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | ElA, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are endothelial cell promoters, such as Tie1, Tie2, Ve-cadherin, EGFL7/lncEGFL7OS or promoters, and muscle specific promoters, including cardiac specific promoters. These include the myosin light chain-2 promoter (Franz et al., 1994; Kelly et al., 1995), the α-actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the α7 integrin promoter (Ziober and Kramer. 1996), the brain natriuretic peptide promoter (LaPointe et al., 1996) and the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Selectable Markers

In certain embodiments of the disclosure, the cells contain nucleic acid constructs of the present disclosure, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

C. Delivery of Expression Vectors

There are a number of ways in which expression vectors may introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway. 1988; Baichwal and Sugden, 1986) and adenoviruses (Ridgeway. 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubinstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1-liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK)(5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^2$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1%3; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991 Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present disclosure. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al, introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu. 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or “episomes” encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo. HeLa and hepatoma cells. Nicolau et al., (1987) accomplished successful liposome-mediated gene transfer in rats after intravenous injection.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/00710%, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

VIII. DEFINITIONS

The term "treatment" or grammatical equivalents encompasses the improvement and/or reversal of the symptoms of disease. "Improvement in the physiologic function" of the heart may be assessed using any of the measurements described herein, as well as any effect upon the animal's survival. In use of animal models, the response of treated transgenic animals and untreated transgenic animals is compared using any of the assays described herein (in addition, treated and untreated non-transgenic animals may be included as controls).

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present disclosure. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "agonist" refers to molecules or compounds that mimic or promote the action of a "native" or "natural" compound. Agonists may be homologous to these natural compounds in respect to conformation, charge or other characteristics. Agonists may include proteins, nucleic acids, carbohydrates, small molecule pharmaceuticals or any other molecules that interact with a molecule, receptor, and/or pathway of interest.

As used herein, the terms "antagonist" and "inhibitor" refer to molecules, compounds, or nucleic acids that inhibit the action of a factor. Antagonists may or may not be homologous to these natural compounds in respect to conformation, charge or other characteristics. Antagonists may have allosteric effects that prevent the action of an agonist. Alternatively, antagonists may prevent the function of the agonist. Antagonists and inhibitors may include proteins, nucleic acids, carbohydrates, small molecule pharmaceuticals or any other molecules that bind or interact with a receptor, molecule, and/or pathway of interest.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

IX. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Animals and in vivo angiogenesis assay. Animal studies were conducted in accordance with the ARVO statement for the Use of Animals in Ophthalmic and Vision Research and were approved by the Institutional Animal Care and Use Committees at the Tulane University. BALB/cAnN-nu (Nude) female mice (6 to 8 weeks of age) from Jackson lab were used for in vivo angiogenesis assay. In vivo Matrigel analysis was performed as described[61]. HUVEC cells transfected with control si-RNA or mix of si-LncEGFL7OS #1 and si-LncEGFL7OS #2 (50 nM each) for 2 days. Cells were then trypsinized and about $5\times10^5$ cells were mixed with 50 μl EBM-2 medium and 350 μl ice-cold Matrigel (BD Biosciences). The mixture was then applied under the back skin of 8-week-old BALB/cAnN-nu (Nude) female mice (Jackson lab). After 14 days, The Matrigel plugs were extracted and snap-frozen in OCT and processed for immunostaining with human EC marker PECAM-1 (DAKO), mouse red blood cell marker Ter-119 (Thermo Fisher), mouse smooth muscle marker αSMA (Abcam), and tube length quantification using image J (National Institute of Health).

Cell Culture, siRNAs and miRNAs. HUVEC (ATCC) cells were grown in EC growth medium EGM-2 (Lonza). HCEC and HREC cells were kindly provided by Dr. Ashwath Jayagapol from Vanderbilt University and grown in EGM2 media (Lonza). EC identity of cells has been confirmed by immunostaining and acetyl-LDL uptake assay (FIG. 0C). ARPE-19 (ATCC) cells were growth in DMEM/F12 (HyClone) media with 10% FBS. HDF (ATCC) cells were grown in DMEM (HyClone) with 10% FBS. All cells have been tested negative for *mycoplasma* contamination. For VEGF treatment, HUVECs were starved with EC basal medium-2 with 0.1% FBS for 24 h and then treated with VEGF (20 ng/mL) for the indicated periods of time. SiRNA transfection in cell culture was performed as described[62]. SiRNAs for LncEGFL7OS were purchased from sigma. Sequences for siRNAs are as follows: si-lncEGFL7OS #1: 5'-GCGUUUCCCUAGCAAUGUUdTdT-3' (SEQ ID NO: 12) and 5'-AACAUUGCUAGGGAAACGCdTdT-3' (SEQ ID NO: 13); si-lncEGFL7OS #2: 5'-CAGCUUUGCCC-UAUCCCAUdTdT-3' (SEQ ID NO: 14) and 5'-AUGG-GAUAGGGCAAAGCUGdTdT-3' (SEQ ID NO: 15). Two pair of siRNAs for MAX gene include: 5'-CC-AGUAUAUGCGAAGGAAAdTdT-3' (SEQ ID NO: 16) and 5'-UUUCCUUCGCAUAUACUGGdTdT-3' (SEQ ID NO: 17), 5'-CACACACCAGCAAGAUAUUdTdT-3' (SEQ ID NO: 18) and 5'-AAUAUCUUGCUGGUGUGUGdTdT-3' (SEQ ID NO: 19). SiRNAs for ETS1 include: 5'-CCGACGAGUGAUGGCACUGAAdTdT-3' (SEQ ID NO: 20) and 5'-UUCAGUGCCAUCACUCGUCGG-3' (SEQ ID NO: 21). SiRNAs for ETS2 include: 5'-CAGU-CAUUCAUCAGCUGGA[dT][dT]-3' (SEQ ID NO: 22) and 5'-UCCAGCUGAUGAAUGACUG[dT][dT]-3' (SEQ ID NO: 23).

LncRNA microarray. RNAs from five cell lines were purified by mirVana™ total RNA Isolation Kit (Ambion. Invitrogen). These RNAs were subjected to microarray-based global transcriptome analysis (Arraystar Human LncRNA array (version 2.0), Arraystar Inc, Rockville, Md.). The lncRNA microarray is designed to detect about 30,586 LncRNAs and 26,109 coding transcripts. The lncRNAs were constructed using the most highly-respected public transcriptome databases (Refseq, UCSC known genes, Gencode, etc), as well as landmark publications. The lncRNA probes include 19590 intergenic lncRNAs (lincRNAs), 4409 intronic lncRNAs, 1299 bidirectional lncRNAs, 1597 sense overlapping lncRNAs and 3691 antisense lncRNAs. Data analyses, including hierarchy clustering analysis and functional enrichment analysis, were performed using Genescript software. The data has been deposited into NCBI GEO database (GSE105107). Tissue distribution data of the top-50 candidates was downloaded from the Stanford Source database[32].

lncEGFL7OS-expressing adenovirus generation and infection. LncEGFL7OS-, lncEGFL7OS-F (2+3), miR-126-, GFP-, or LacZ-expressing adenoviruses were generated as described[63]. Briefly, lncEGFFL7 cDNA was amplified by PCR using Phusion High-Fidelity DNA Polymerase from HUVEC cDNAs (ThermoFisher Scientific) and cloned into TOPO vector using the following primers: lncEGFL7up: 5'-GCCCTTTGGGCTCAGGCCCAGA-3' (SEQ ID NO: 24) and lncEGFL7dn: 5'-GCCCTTTGGGTTTGAGTAATAATTAC-3' (SEQ ID NO: 25). After confirmation by sequencing, the fragment was cloned into pshuttle-CMV vector after HindIII/XhoI digestion. For lncEGFL7OS-F (2+3) cloning into pshuttle-CMV vector, the following primers were used: 5'-aaaagatc-tATGGCGTGTGAGTGCATGGCGAGC-3' (SEQ ID NO: 26) and 5'-tataagcttTGGGTTTGAGTAATAATTACATCAT-3' (SEQ ID NO: 27). For making miR-126 adenovirus, miR-126-containing genomic DNA was PCR amplified from mouse using the following primers: 5'-ATGCGAAT-TCGAGTGAAAGAGCCCCACACTG-3' (SEQ ID NO: 28) and 5'-ATGCAAGCTTAGTGCCAGCCGTGGTCCT-TAC-3' (SEQ ID NO: 29) and cloned into pshuttle-CMV vector after ECORI/HindIII digestion. The positive clones were cut with PmeI and transformed into *E. coli* with adenovirus vector for recombination. Positive clones were then cut with PacI and transfected into Ad-293 cells using ViralPack Transfection Kit from Stratagene. Viral titers were determined by End-Point Dilution Assay. For adenovirus infection, the cells were switched to serum free EBM-2 medium and adenovirus was added at an MOI of 10. The infection medium was removed after 3 hrs. Cells were washed with PBS and overlaid with fresh growth medium and cultured for 48 h before further experiments.

Cell Proliferation, Cell cycle analysis, TUNEL assay, Scratch-Wound, and in vitro EC-fibroblast co-culture angiogenesis assay. EC cell proliferation, TUNEL assay and scratch-wound assays were performed using HUVEC cells as described[62]. For cell proliferation assay, about $2\times10^3$ transfected HUVECs were seeded in 96-well plates. After starvation with 0.1% serum for overnight, the cells were stimulated with 20 ng/mL VEGF-A for 20 hours and then subjected to BrDU labeling for 4 hours. DNA synthesis as determined by BrDU incorporation was quantified using a commercial ELISA kit from Roche according to the manufacturer's instructions. Cell cycle analysis was performed using Guava® Cell Cycle Reagents (Guava Technologies) on a Guava instrument and analyzed using Cytosoft™ software according to the manufactural manual. For scratch wound assay, scratch-wound was made using a 200-μL pipette tip in lncRNA or control siRNA-transfected HUVEC monolayer before VEGF (20 ng/mL) stimulation. 1 μM of 5-fluouracil (Sigma) was then added to the cells right after scratch wound to block cell proliferation. Post-scratch EC migration was scored at 14 h after wound scratch. For in vitro angiogenesis assay, at 3 days after lncRNA or control siRNA transfection with Liptofectamine RNAiMAX™ reagent (Invitrogen), cells were harvested for RNA or in vitro Matrigel assay and branch point analysis as described before.

In vitro EC-Fibroblast co-culture was performed as described[44]. Briefly, human dermal fibroblast cells (HDF) were seeded into each well of a 24 well plate and maintained in DMEM at $6\times10^3$ cells/well until they developed confluent monolayers. HUVECs were maintained as described above and transfected with siRNA one day prior to seeding on HDF monolayers. Approximately $6\times10^3$ HUVECs were seeded onto each monolayer and the HDF/HUVEC co-culture was maintained for 7 days in EGM-2 medium with medium changes every 2-3 days to allow endothelial cell polarization, migration, networking, and the formation of an in vitro primitive vascular plexus. For rescue experiments, some wells were transfected with Ad-miR-126 (MOI of 10) and EGFL7 (Abcam) protein was added to the medium at 10 nM every other day. After 7 days the wells were fixed with 100% Methanol at −20° C. for 20 minutes and then stained with anti-PECAM-1 (DAKO). After hybridizing a secondary antibody, the endothelial tissue was visualized and imaged under a Nikon microscope. Multiple images were automatically stitched with Nikon software to provide a large image (several $mm^2$) and the resulting image was analyzed on ImageJ software to determine the degree of vasculanzation. Three wells were used for each condition and results are representative of the mean of each three well group. The experiments were repeated for at least three repeats with similar results.

Ex vivo human choroid sprouting assay. Ex vivo human choroid sprouting assay was adapted from a mouse protocol[64]. Donated human eye balls were obtained from Southern eye bank (New Orleans. LA). The use of deceased human eye balls for the study was EXEMPT under DHHS regulations (46.101(b)) after consultation with the Tulane IRB committee. Informed consent has been obtained from all subjects by Southern eye bank. Eyes were collected within 24 hours of decease of the donors and cleaned and kept in sterile ice-cold PBS with Penicillin/Streptomycin before dissection. Using fine forceps, the cornea and the lens from the anterior of the eye were removed. The peripheral choroid-scleral complex was separated from the retina and the RPE layer was peeled away using fine forceps. The choroid-scleral complex was then cut into approximately 4 $mm^2$ pieces using sterile scalpel blade under laminar airflow. The choroid was then washed with sterile ice-cold PBS and transferred into endothelial base medium (EBM2) with 0.1% FBS (300 μl/well in 24-well plates). The choroid was transfected with control si-RNA or mix of si-LncEGFL7OS #1 and si-LncEGFL7OS #2 (50 nM each) for overnight. Choroid fragments were then washed by EGM2 media then placed in growth factor-reduced Matrigel™ (BD Biosciences) in 24-well plate. Briefly, 30 μl of matrigel was used to coat the bottom of 24 well plates without touching the edge of the well. After seeding the choroid, the plate was incubated in a 37° C. cell culture incubator to make the Matrigel solidify. 500 μl EC growth medium (EGM-2) were added slowly to the plate without disturbing the Matrigel, and the plate was incubated at 37° C. cell culture incubator with 5% CO2. Cell culture medium was changed every 48 hours. The EC sprouts normally start to appear on the day 5 and grow rapidly between day 8 and 10. Phase contrast photos of individual explants were taken using a Nikon microscope. The sprouting distance was quantified with computer software ImageJ (National Institute of Health). Sprouting ECs were stained with ICAM-2 (BD Pharmingen) or isolectin B4 (Vector Lab).

RNA, Western blot analysis and Immunofluorescence. Human total RNA master panel II was purchased from clontech (Takara). Total RNA was isolated from human choroid tissues or cell lines using TRIzol reagent (Invitrogen). Cytoplasmic and nuclear RNA was purified using a Cytoplasmic & Nuclear RNA Purification Kit (Norgen Biotek Corp., Thorold, ON, Canada) according to manufacturer's supplied protocol. In brief, cells growing in monolayer were rinsed with 1×PBS and lysed directly on the plate with ice-cold Lysis Buffer. Next cell lysate was transfer to the RNase-free microcentrifuge tube and spun for 3 minutes at 14,000×g. Supernatant containing cytoplasmic RNA was mixed with manufacturer's supplied buffer (Buffer SK) and 100% ethanol and applied onto a spin column. The pellet containing the nuclear RNA was mixed with Buffer SK and 100% ethanol and applied onto a spin column. Both columns were washed with supplied Wash Solution, and RNA was eluted with supplied elution buffer (Elution Buffer E). For maximum recovery two rounds of elution were performed. Quantitative (q) RT-PCR or regular RT-PCR was performed using iScript™ cDNA Synthesis system (BioRad), miRNA qRT-PCR was performed using qScript™ cDNA Synthesis and microRNA Quantification System (Quanta Biosciences). lncEGFL7OS RACE PCR was performed using Marathon®-ready cDNA from human placenta (Clontech, Mountain View, Calif.). 5'RACE and 3'RACE PCR was carried out using lncEGFL7OS primers and primers from the kit. Then a second round of PCR was performed using the combination of the RACE products and the RACE primers from the kit. The derived PCR product was then cloned using TOPO vector and sequenced. Primers for real-time PCRs include human β-actin, 5'-GAGCAAGAGATGGCCACGG-3' (SEQ ID NO: 30) and 5'-ACTCCATGCCCAGGAAGGAA-3' (SEQ ID NO: 31); lnc-FLI1-AS1 (also named SENCR), up: 5'-CCTGAGGCCATCTTACCACC-3' (SEQ ID NO: 32), down: 5'-AATCCGCTTCGATGAGTGGG-3' (SEQ ID NO: 33); SENCR (for regular PCR), up: 5'-GCGCATTGTTAGGAGAAGGG-3' (SEQ ID NO: 34), down: 5' CCTGCTGACTGTCCTAGAGG-3' (SEQ ID NO: 35); lnc-GATA2-AS, up: 5'-CGGGCAGCTTACGATTCTTC-3' (SEQ ID NO: 36), down: 5'-CGGTGTCTTTCAGAGGGTCT-3' (SEQ ID NO: 37): lnc-ECE1, up: 5'-CCATGTCGCCTCAGCCTAAA-3' (SEQ ID NO: 38), down: 5'-GGGCAGTCTCAGGGTAACAC-3' (SEQ ID NO: 39); lnc-ESAM, up: 5'-CTCGGAAAACGGAGGGTTGA-3' (SEQ ID NO: 40), down: 5'-CGCTGCCCTTAATTCCTTGC-3' (SEQ ID NO: 41): lnc-ROBO4-AS, up: 5'-ACCAGCAGACCCTGAAACTC-3' (SEQ ID NO: 42), down: 5'-GGCAGGGATCAGGCATTCAT-3' (SEQ ID NO: 43); lnc-EGFL7OS, up: 5'-AGTGCCAGCTTTGCCCTATC-3' (SEQ ID NO: 44), down: 5'-GAGAACACAGGACGTCCACA-3' (SEQ ID NO: 45); EGFL7-A, up: 5'-CTTCAGAGGCCAAAAGCACC-3' (SEQ ID NO: 46), down: 5'-GAATCAGTCATCCCCCGGAC-3' (SEQ ID NO: 47); EGFL7-B, up: 5'-AAGGGAGGCTCCTGTGGA-3' (SEQ ID NO: 48), down: 5'-CCTGGGGGCTGCTGATG-3' (SEQ ID NO: 49); EGFL7-C, up: 5'-CGGATCCGGCGGCCA-3' (SEQ ID NO: 50), down: 5'-CGAACGACTCGGAGACAGG-3' (SEQ ID NO: 51); Neatl. up: 5'-AGATACAGTGTGGGTGGTGG-3' (SEQ ID NO: 52), down: 5'-AGTCTTCCCCACCTTGTAGC-3' (SEQ ID NO: 53). Human primiR-126, up: 5'-TGGCGTCTTCCAGAATGC-3' (SEQ ID NO: 54), down: 5'-TCAGCCAAGGCAGAAGT-3' (SEQ ID NO: 55). Human Cyclin D2, up: 5'-GCTGTGCATTTACACCGACA-3' (SEQ ID NO: 56); down: 5'-TGCGCAAGATGTGCTCAATG-3' (SEQ ID NO: 57). Human DFHR, up: 5'-ATTTCGCGCCAAACTTGACC-3' (SEQ ID NO: 58); down: 5'-TCTGAATTCATTCCTGAGCGGT-3' (SEQ ID NO: 59).

For Western blot analysis, protein lysates were resolved by SDS-PAGE and blotted using standard procedures. Antibodies used were as follows: ERK1/2 (Cell signaling), Phospho-ERK1/2 (Cell signaling), AKT (Cell signaling), Phospho-AKT (Cell signaling), EGFL-7 (Abcam) and β-Tublin (Abcam). For immunofluorescence experiments, samples were fixed with 4% paraformaldehyde or methanol for 30 min. After treatment with 1% Triton X-100 in PBS, samples were incubated in PBS containing 4% goat serum for 30 min. The samples were then incubated with primary antibodies overnight at 4° C., followed by incubation with appropriate secondary antibodies. Antibody used for immunofluorescence include: ICAM-2 (BD Pharmingen), PECAM-1 (DAKO).

Single-cell RNA copy number determination. Single-cell lncEGFL7OS RNA copy number was determined as modified from a previous publication[65]. Briefly, $10^6$ HUVEC cells were harvested for total RNA isolation using Trizol. 16% (8 μl out of 50 μl) of the total RNA was used for reverse transcription reaction as described above, and 1/100 of the cDNA was used as template in each well for the subsequent qRT-PCR. Therefore, for each well, the total lncEGFL7OS came from about ~1600 cells. For establishing the standard curve, pCRII-TOPO-lncEGFL7OS plasmid was linearized for generating lncEGFL7OS RNA by in vitro transcription. After concentration determination and copy number calculation, a given amount of RNA was employed to carry out the reverse transcription under the same conditions for HUVEC total RNA. The derived cDNA was diluted for PCR to generate a standard curve for lncEGFL7OS PCR. The copy number of RNA per cell was calculated based on the CT number.

High resolution RNA FISH experiments. 25 Stellaris RNA Fluorescence In situ Hybridization (FISH) probes for lncEGFL7OS were designed according to Stellaris FISH probe designer (world-wide-web at biosearchtech.com/Account/Login?return=/stellaris-designer). RNA-FISH was performed following the manufacturer's protocol. Briefly, HUVECs cultured on 18-mm coverglasses were fixed and permeabilized by methanol-acetic acid solution for 10 minutes. After removing the fixation solution, cells were washed by Wash Buffer A (Biosearch Tech) at room temperature for three minutes, and then transferred to a humidified chamber to incubate with Hybridization Buffer (Biosearch Tech) containing the probes. The coverglasses were put upside-down on Parafilm for overnight. After washing with Wash Buffer A (Biosearch Tech) at 37° C. for 30 minutes, the cells were incubated with Wash Buffer A containing 5 ng/ml DAPI in the dark at 37° C. for 30 minutes. Finally, Wash Buffer B was added and the cells were incubated at room temperature for 5 minutes before mounting coverglass onto the slides with mounting medium. Pictures were taken under a Nikon A1 confocal microscope. For RNA copy quantification, hybridization signals and DAPI positive nucleus were counted manually.

Co-immunoprecipitation (Co-IP), Chromatin Immunoprecipitation (ChIP) and RNA immunoprecipitation (RIP) assays. Co-immunoprecipitation assay was carried out following the Abcam protocol. Briefly, $10^7$ HUVEC cells were scraped and resuspended in ice-cold lysis buffer (20 mM Tris.Hcl pH8, 137 mM NaCl, 1% NP-40, 2 mM EDTA, 10 mM beta-mercaptoethanol, 15 U/mi DNAse I, protease Inhibitors). After 30 minutes on ice, cell lysate was centrifuged at 12000 g for 15 min at 4° C. The supernatant was transferred to another pre-chilled tubes and pre-cleared by 2 μg off-target rabbit antibody (Santa Cruz) followed by 40 μl of protein G magnetic bead slurry (Bio-rad) at 4° C. 25 μl pre-cleared cell lysate was reserved as input control. The rest was divided into two parts and added 2 μg of off-target rabbit IgG (Santa Cruz) and anti-P300 antibody (Abcam) respectively. The samples were incubated with antibodies at 4° C. for overnight under gentle rotation. Then, 60 μl of protein G magnetic bead slurry (Bio-Rad) was added into each sample. Incubate the lysate beads mixture at 4° C. under rotation for 4 hours, then centrifuge the tubes and discard supernatant. The beads were washed with lysis buffer gently for three times. The proteins were eluted by SDS loading buffer (supplemented with 10 mM beta-mercaptoethanol and protease Inhibitors). Western blot was used to analyze the content of samples.

ChIP experiments were performed as described with some modifications[66]. Briefly, HUVEC cells were cultured in the 10-cm dishes to 80-90% of confluence. After adding 400 μl of 37% formaldehyde to 10 ml medium and incubation for 15 minutes to fix the cells, cells were rinsed by pre-chilled PBS buffer and collected in 1 ml IP buffer (150 mM NaCl, 50 mM Tris-HCl (pH 7.5), 5 mM EDTA, NP-40 (0.5% vol/vol), Triton X-100 (1.0% vol/vol), 1% proteinase inhibitor cocktails). After half an hour of sonication, 2 μg of antibodies were added into cell lysate and incubated in ultrasonic bath for 30 minutes. Protein G Magnetic Beads were used to pull down antibodies in 4° C. rotating platform for 2 h. Once beads were washed for 5 times by cold IP buffer, 100 μl 10% (wt/vol) Chelex-100 was mixed with washed beads, and the mixture was boiled for 10 minutes. Each sample was added 1 μl of 20 μg/μl proteinase K and incubated at 55° C. for 30 minutes. Samples were boiled for 10 minutes again and centrifuged. Supernatant were collected for real-time PCR ChIP grade antibodys used in ChIP assay: Max (Santa Cruz, sc-197), Myc (Sigma-Aldrih, c3956), Anti-RNA Polymerase II (Abcam, ab5408), Tri-Methel-Histon H3(Lys4) (Cell Signaling, #9751), ETS1 (Santa Cruz, sc-111), H3K27Ac antibody (Abcam, Ab4729), Normal Rabbit IgG (Cell Signaling, #2729). ChIP samples were analyzed by using normal PCR with following parameters: (1) initial denaturation at 94° C. for 10 min, (2) denaturation at 94° C. for 20 s, (3) anneal at 58° C. for 30 s, (3) extension at 72° C. for 1 min. Steps from 2 to 4 were repeated 35 times. Primers to amplify conserved transcription factors binding region in the lncEGFL7OS enhancer/promoter region were as follows: Primers 1: 5'-CTGGCTGTTTTGGGGCTAGA-3' (SEQ ID NO: 60) and 5'-CCTGTGTGTGTTCTCCGCT-3' (SEQ ID NO: 61). Primers 2 (control region): 5'-AGATCCCAGGGCTGTTTAGC-3' (SEQ ID NO: 62) and 5'-AACACTCCTCCCAGCGAATC-3 (SEQ ID NO: 63). Primers for Cyclin D2 and DFHR promoter regions are as follows: Cyclin D2 promoter-F: 5'-GCAGGGAACCTAGTGTACGG-3' (SEQ ID NO: 64); Cyclin D2 promoter-R: 5'-CGCGCCCTTTGGTGTATTTC-3' (SEQ ID NO: 65); DHFR promoter-F: 5'-CGGGGCTACAAATTGGGTGA-3' (SEQ ID NO: 66); DHFR promoter-R: 5'-TAAAAGACGCACCCCTTGCC-3' (SEQ ID NO: 67).

RNA immunoprecipitation (RIP) was performed following a protocol from Abcam. Briefly, $10^7$ Ad-GFP or Ad-lncEGFL7OS-infected HUVEC cells were harvested by trypsinization and resuspended in PBS buffer respectively when the confluence was about 90%. Freshly prepared nuclear isolation buffer (1.28 M sucrose, 40 mM Tris-HCL pH7.5, 20 mM $MgCl_2$, 4% Triton X-100) was diluted by 3×ddH2O and used to resuspend the above cell pellets. After incubation on ice for 20 minutes with frequent mixing, cell nuclei were collected by centrifugation at 2500 g for 15 min at 4° C. and resuspended in 1 ml freshly prepared RIP buffer (150 mM KCl, 25 mM Tris pH7.4, 5 mM EDTA, 0.5 mM DTT, 0.5% NP40, 100 U/ml RNAase inhibitor, protease inhibitors). After chromatin shearing, RNA supernatants were collected by centrifugation at 13000 rpm for 10 min to remove nuclear membrane and debris. 2 μg mock and anti-Max IgG were added into 500 μl supernatant respectively and incubated overnight at 4° C. 40 μl protein G magnetic beads (Bio-rad) was added and incubated for 2 hours at 4° C. with gentle rotation. Coprecipitated RNAs were resuspended in 1 ml TRIzol reagent (Invitrogen™) according to manual. Extracted RNAs were employed for subsequent reverse transcription and cDNA analysis. Some RNA samples were used as controls.

Determination of MAX binding domain in lncEGFL7OS. LncEGFL7OS was separated into three domains according to its predicted secondary structure. Briefly, F1 domain contains 1-239 nt of lncEGFL7OS, F2 domain contains 208-393 nt and F3 domain contains 377-557 nt. The separated domains were PCR amplified and sub-cloned into pShuttle-CMV vectors (Agilent Technologies) respectively and transfected into APRE-19 cells together at 3 ug per vector per dish. After 48 hours, cells were harvested, the expression of the lncRNA fragments was confirmed by RT-PCR, and RNA immunoprecipitation (RIP) was performed by using MAX antibody as described above. Wild-type ARPE 19 cells were harvested as background control since its lncEGFL7OS level is under the detection threshold. Dnase I was used to remove potential DNA contamination from the RNA samples before first-strand cDNAs were synthesized. Primers for construction and detection as below:

```
                                   (SEQ ID NO: 68)
F1-5': 5'-AATAGATCTTGGGCTCAGGCCCAGAGTGCCCA-3';

                                   (SEQ ID NO: 69)
F1-3': 5'-AAAAAGCTTCTGGAGGCGCTCGCCATGCAC-3';

                                   (SEQ ID NO: 70)
F2-5': 5'-AATAGATCTATGGCGTGTGAGTG CATGGC-3';

                                   (SEQ ID NO: 71)
F2-3': 5'- AAAAAGCTTTCAGGTAGCTGCGAGTTCAAG-3';

                                   (SEQ ID NO: 72)
F3-5': 5'-AATAGATCTACTCGCAGCTACCTGAGTCAGA-3';

                                   (SEQ ID NO: 73)
F3-3': 5'-AAAAAGCTTTG GGTTTGAGTAATAATTACATC-3'.
```

CRISPRi (dCas9-KRAB) Assay. CRISPRi (dCas9-KRAB) assay was perform as described[67], pHR-SFFV-dCas9-BFP-KRAB (Addgene: 46911) and control (PLJM1-EGFP) vectors were packaged into lentivirus vectors respectively. sgRNA-1 (TGCTTACAGGCAA-GGGGCGA; SEQ ID NO: 2) and sgRNA-2 AAGAAT-TGCTTCAGCTCGGA: SEQ ID NO: 3), which target IncEGFL7OS promoter and intron respectively, were sub cloned into lentiGuide-Puro vector (Addgene: 52963), which could express sgRNAs to assemble with dCas9-Krab. Empty lentiGuide-Puro vector serves as control. For the assay, HUVEC cells were transduced by control or dCas9-Krab vector, combing with lentiGuide-gRNA1, lentiGuide-gRNA2 and empty lentiGuide-Puro respectively. All lentivirus vectors were employed at 10 MOI. EC-fibroblast co-culture was performed as described above. The total sgRNA sequences after cloning are: sgRNA-1 (TGCTTA-CAGGCAAGGGGCGAgttttagagctagaaatagcaagttaaaa ta-aggctagtccgttatcaacttgaaaaagtggcaccgagtcggtgc; SEQ ID NO: 4) and sgRNA-2 (AAGAATT G-CTTCAGCTCG-GAgttttagagctagaaatagcaagttaaaataaggctagtccgttatcaactt-gaaaaagtggcaccgagtcgg-tgc; SEQ ID NO: 5). Empty lenti-Guide-Puro vector serves as control. For the assay, HUVEC cells were transduced by control or dCas9-Krab vector, combing with lentiGuide-gRNA1, lentiGuide-gRNA2 and empty lentiGuide-Puro respectively. All lentivirus vectors were employed at 10 MOI. EC-fibroblast co-culture was performed as described below.

Luciferase assay. Luciferase assays were performed as described[34]. The putative bidirectional promoter for lncEGFL7OSEGFL7 was PCR amplified from human DNA and cloned into promoterless PGL3 Basic luciferase vector (Promega). Primers include: plncEGFL7OSup (XhoI); 5'-atcgCTCAGATAGACTCTGATGGCCCAGG-3' (SEQ ID NO: 74) and plncEGFL7OSdn (XhoI): 5'-atcgCTCA-GACCAGCTTGGTGCAGGGAG-3' (SEQ ID NO: 75). 293T cells in 24-well plates were transfected with 50 ng of reporter plasmids in the presence or absence of increasing amount of Ets1 or Ets1 DNA-binding mutant expression plasmid.

Human samples. The human study was performed according to the principles of the Declaration of Helsinki. Patient information was described previously[68]. The procedure was approved by the Institutional Ethics Committee of the National Institute of Cardiovascular Diseases, Bratislava. Slovakia. Briefly, left ventricular tissues from 7 patients with terminal-stage heart failure and 5 control healthy donors were dissected and snap frozen, and used for RNA isolation and gene expression study.

Statistics. In the bar graphs without P-value analysis, the central values are the means, and the error bars are standard deviation. In the bar graphs with P-value analysis, the central values are the means, and the error bars are standard error of means. Significant differences between groups were analyzed via Student's unpaired t-test (default). For multiple group analysis, significances between multiple groups were analyzed by ordinary ANOVA followed by Tukey honest significant difference testing. P-values of less than 0.05 were considered to be statistically significant.

```
Primers for PCR. lnc-EGFL7OS, up:
                                    (SEQ ID NO: 6)
5'-AGTGCCAGCTTTGCCCTATC-3',

down:
                                    (SEQ ID NO: 7)
5'-GAGAACACAGGACGTCCACA-3';

EGFL7-B, up:
                                    (SEQ ID NO: 8)
5'-AAGGGAGGCTCCTGTGGA-3',

down:
                                    (SEQ ID NO: 9)
5'-CCTGGGGGCTGCTGATG-3';

Human primiR-126, up:
                                   (SEQ ID NO: 10)
5'-TGGCGTCTTCCAGAATGC-3,

down:
                                   (SEQ ID NO: 11)
5'-TCAGCCAAGGCAGAAGT-3'.
```

Example 2—Results

Figure 1B:
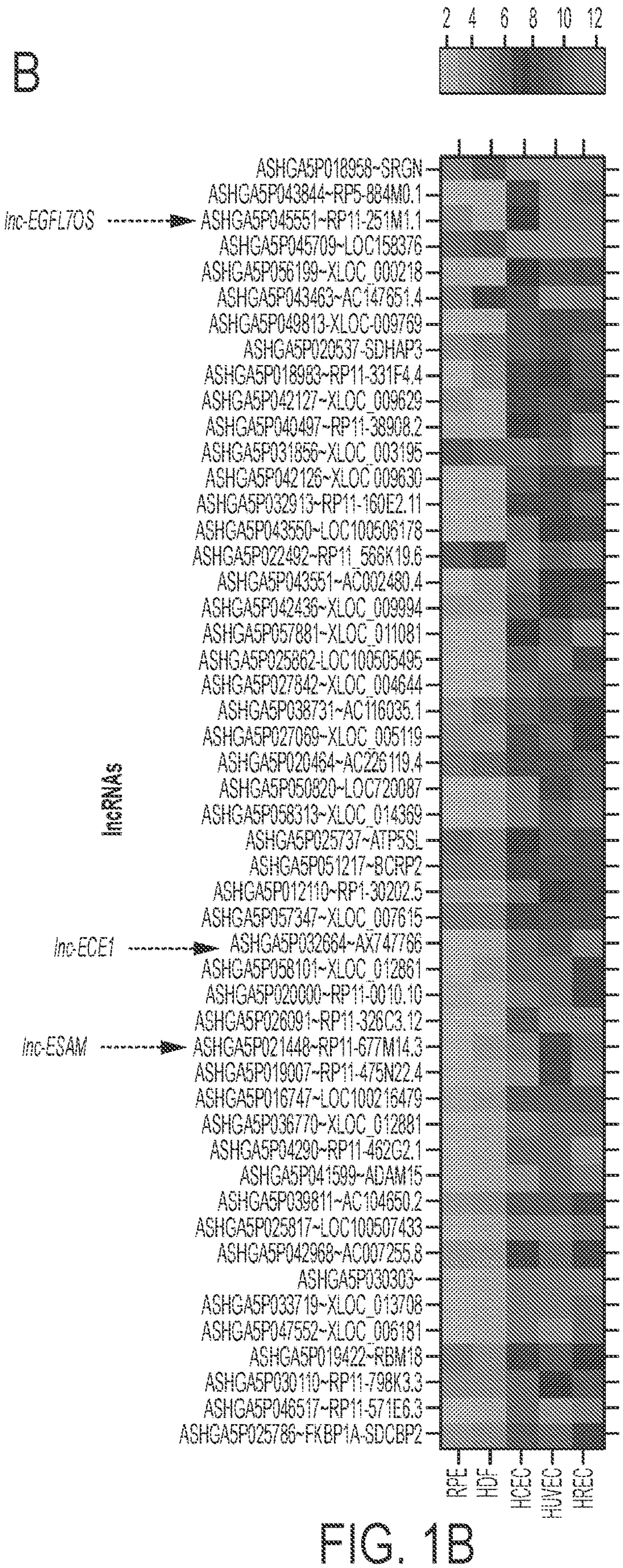
Figure 10A:
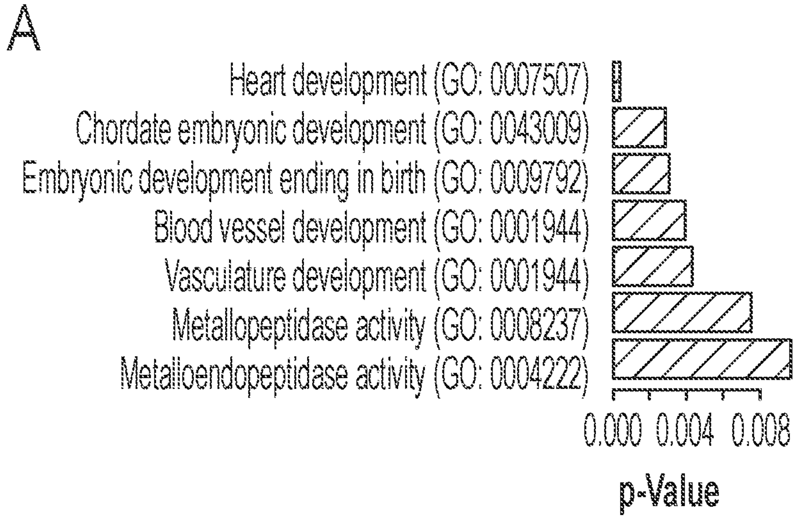
Figure 10C:
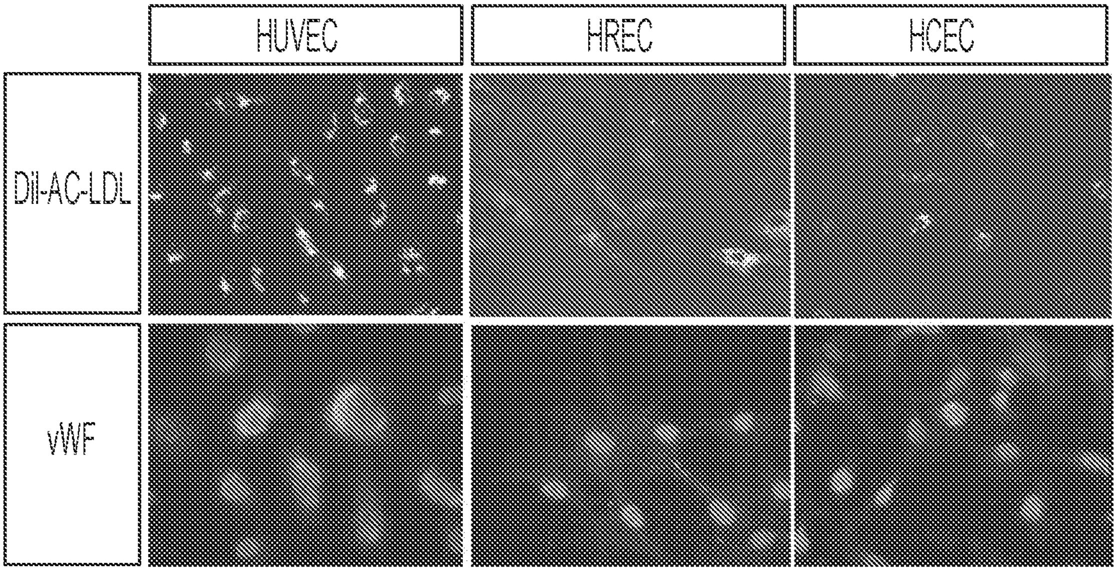

Microarray profiling of lncRNAs in ECs and confirmation of the EC-restricted lncRNAs. To identify lncRNAs specific in ECs, a microarray was performed to profile ~30,000 lncRNAs and ~26,000 coding transcripts using an Arraystar human LncRNA microarray v3.0 system (Arraystar, Rockville, Md.). Three primary human EC lines and two non-EC lines at low passages, namely, human umbilical vein EC (HUVEC), human retinal EC (HREC), human choroidal EC (HCEC), human dermal fibroblast cell (HDF) and human retinal pigment epithelial (RPE) cell lines, were used in the array. Purity of EC lines was confirmed by acetyl-LDL uptake and EC marker staining (FIGS. 1A-D; FIG. 10C). Hierarchical cluster analysis of the array results validated the clustering of EC lines, which clearly separates from the HDF and RPE cell lines based on lncRNA and mRNA expression (FIG. 1A). Moreover, lncRNAs appeared to be a stronger classifier to distinguish between EC and non-ECs than mRNAs. 498 lncRNAs are enriched in all three EC lines for more than 2 folds compared to the non-ECs (see FIG. 1B for top 50 hits). Among them, 308 are intergenic lncRNAs, 62 are sense overlapping lncRNAs, 83 are antisense lncRNAs, 23 are bidirectional lncRNAs, and 22 lncRNAs were previously identified as pseudogenes (FIG. 1C). When these lncRNAs were cross-referenced with the enhancer-like lncRNAs, 19 of them are known enhancer-like lncRNAs with nearby coding genes within 300 kb (data not shown)[30]. The inventors also took advantage of their microarray system in profiling both lncRNAs and mRNAs and examined the lncRNA/mRNA regulation relationship for the EC-restricted lncRNAs. Since many lncRNAs have been shown to exert locus specific effect on nearby genes, they first performed a bioinformatics search for protein-coding genes that are within 10 kb of the 498 EC-restricted lncRNAs. 91 lncRNAs have protein-coding genes within 10 kb of the lncRNA gene (data not shown). Moreover, 27 of the 91 lncRNAs exhibited parallel expression pattern to the neighboring mRNAs in all 5 cell lines tested, while three of them showed inverse expression pattern relationship with the neighboring mRNAs. For some lncRNAs, including those near to SRGN, FOXC2, STEAP1B, ECE1, GOT2, EGFL7 and PRKAR1B, the specificity for lncRNA in ECs is more robust than the neighboring mRNAs; for some other lncRNAs, including those near to HHIP, ESAM, and UBE2L3, their EC-specificity is less robust than their neighboring mRNAs. These results suggest that some lncRNAs can serve as robust EC-restricted gene expression markers, the inventors also carried out a functional enrichment analysis based on the EC-restricted lncRNAs and the associated genes. The following biological processes and genes are highly represented in the associated lncRNAs with a false discovery rate (FDR) of less than 10% (FIG. 10A): (1) heart development (NRP1, ECE1, FOXC2, PKD1, ZFPM2, FKBPIA, FOXP4); (2) chordate embryonic development (GATA2, SATB2, ECE1, LMX1B, FOXC2, PKD1, ZFPM2); (3) embryonic development ending in birth (GATA2, SATB2, ECE1, LMX1B, FOXC2, PKD1, ZFPM2); (4) blood vessel development (NRP1, EGFL7, ROBO4, FOXC2, PKD1, ZFPM2); (5) vasculature development (NRP1, EGFL7, ROBO4, FOXC2, PKD1, ZFPM2); and (6) metallopeptidase activity (ECE1, ADAMTS16, LTA4H, MMP25, ADAM15). From above, genes involved in embryonic development, especially vascular development, are associated with the EC-restricted lncRNAs. Taken together, the inventors have established the lncRNA expression profile in ECs by comparative lncRNA microarray, and identified hundreds of EC-restricted lncRNAs, with a list of them having associated genes involved in vascular development.

Quantitative (q) RT-PCR was used to confirm a selected list of EC-enriched lncRNAs from the microarray. Friend leukemia integration 1 (FLI1) antisense lncRNA (FLI1 AS, also named as SENCR[3], ASHGA5P026051), GATA binding protein 2 (GATA2) antisense lncRNA (IncGATA2, ASHGA5P019223. RP11-475N22.4), endothelial converting enzyme 1 (ECE1) intron sense-overlapping lncRNA (lncECE1, ASHGA5P032664, AX747766), endothelial cell-selective adhesion molecule (ESAM) bidirectional lncRNA (lncESAM, ASHGA5P021448, RP11-677M14.3), roundabout homolog 4 (ROBO4) nature antisense RNA (lncROBO4, ASHGA5P026882, RP11-664121.5), and epidermal growth factor-like domain 7 (EGFL7) opposite strand lncRNA (lncEGFL7OS, ASHGA5PO45551, RP11-251M1.1) were chosen because of their EC restriction and potential relevance to EC function. As shown in FIG. 1D, the expression of lncECE1, lncGATA2, lncESAM, lncROBO4, lncFLI1 and lncEGFL7OS was found to be highly enriched in EC cell lines compared to the non-EC lines. Among different EC lines, lncECE1 and lncESAM were more enriched in HUVECs, while FLI1AS and lncEGFL7OS were more enriched in HCECs, supporting heterogeneity of ECs and suggesting differential expression of the lncRNAs in different ECs.

The inventors also used a bioinformatics approach to determine the tissue distribution of the EC-restricted lncRNAs. The tissue expression information of the top 50 EC-restricted lncRNAs was obtained from the Stanford Source database[32]. FIG. 10B showed the tissue distribution heatmap of the candidate lncRNAs with information available. The majority of the lncRNAs are enriched in the lung and placenta, which are highly vascularized tissues. Taken together, these data support the EC- and vasculature-restriction of the candidate lncRNAs from the inventors' microarray.

Figure 2A:
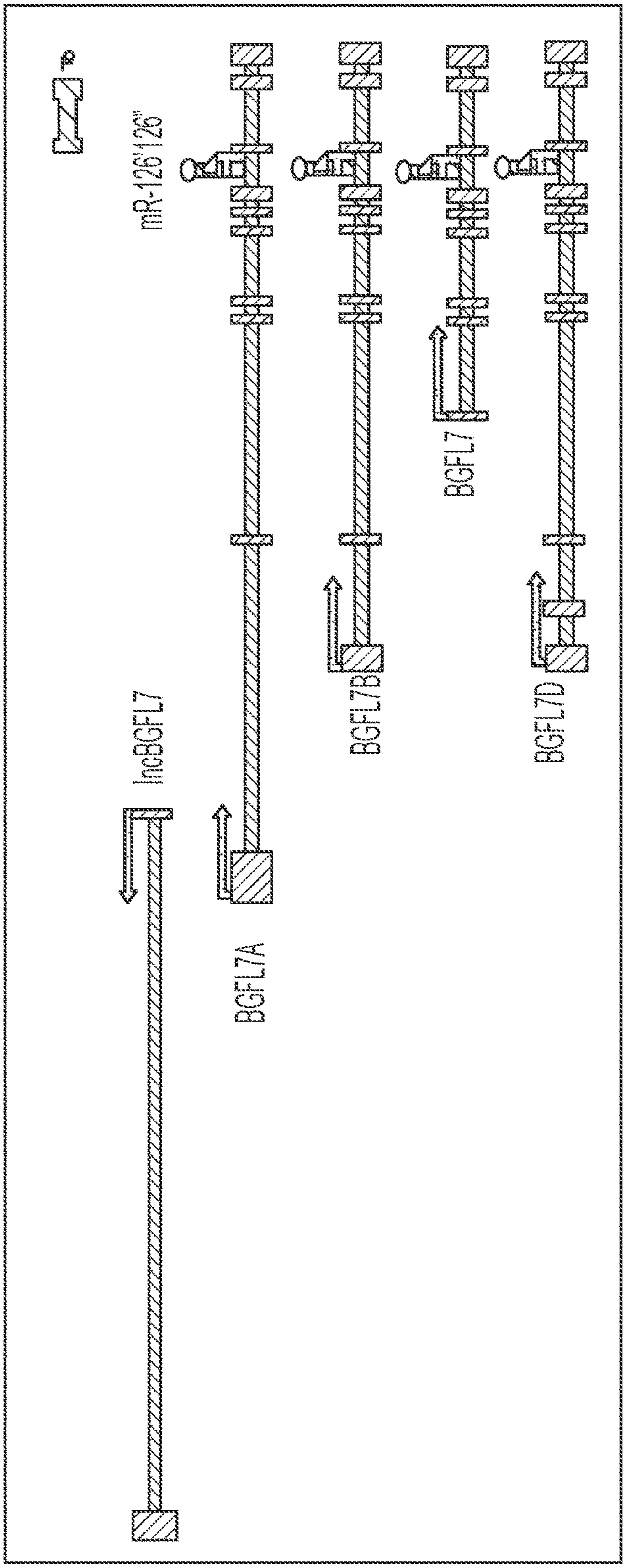
Figure 2B:
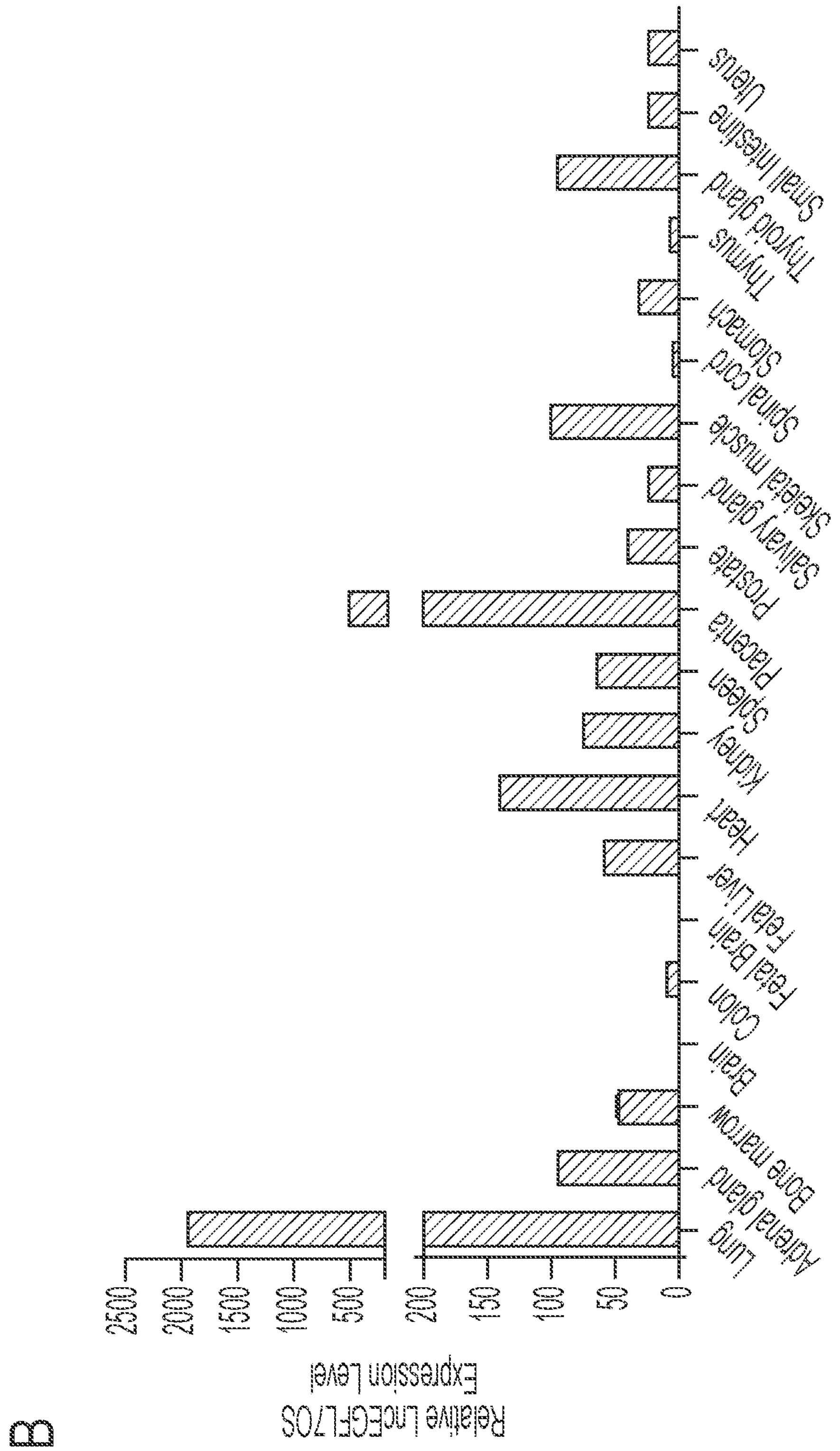
Figure 11A:
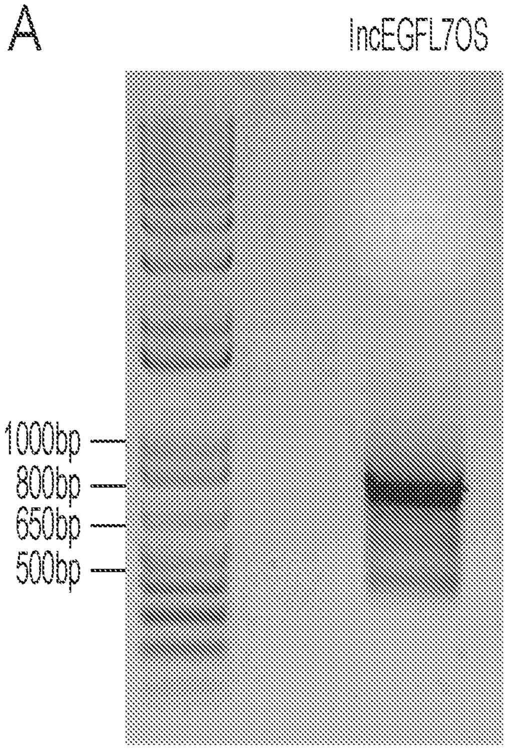
Figure 11B:
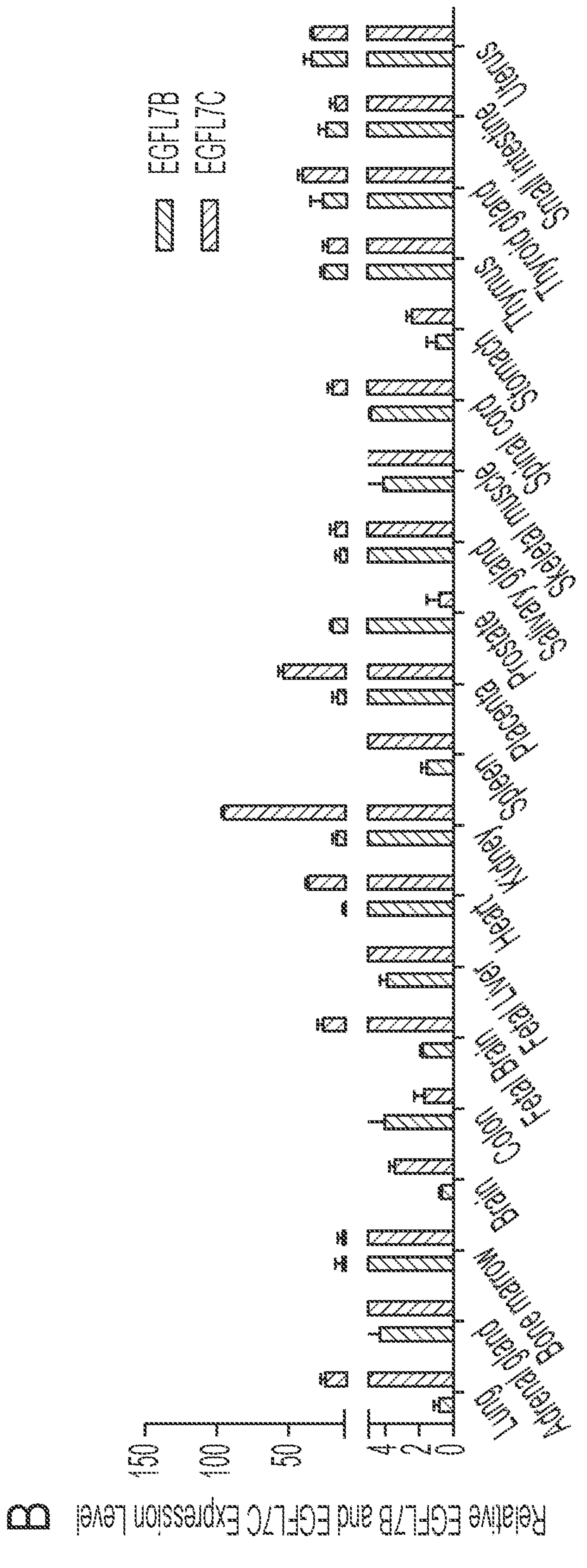
Figure 11C:
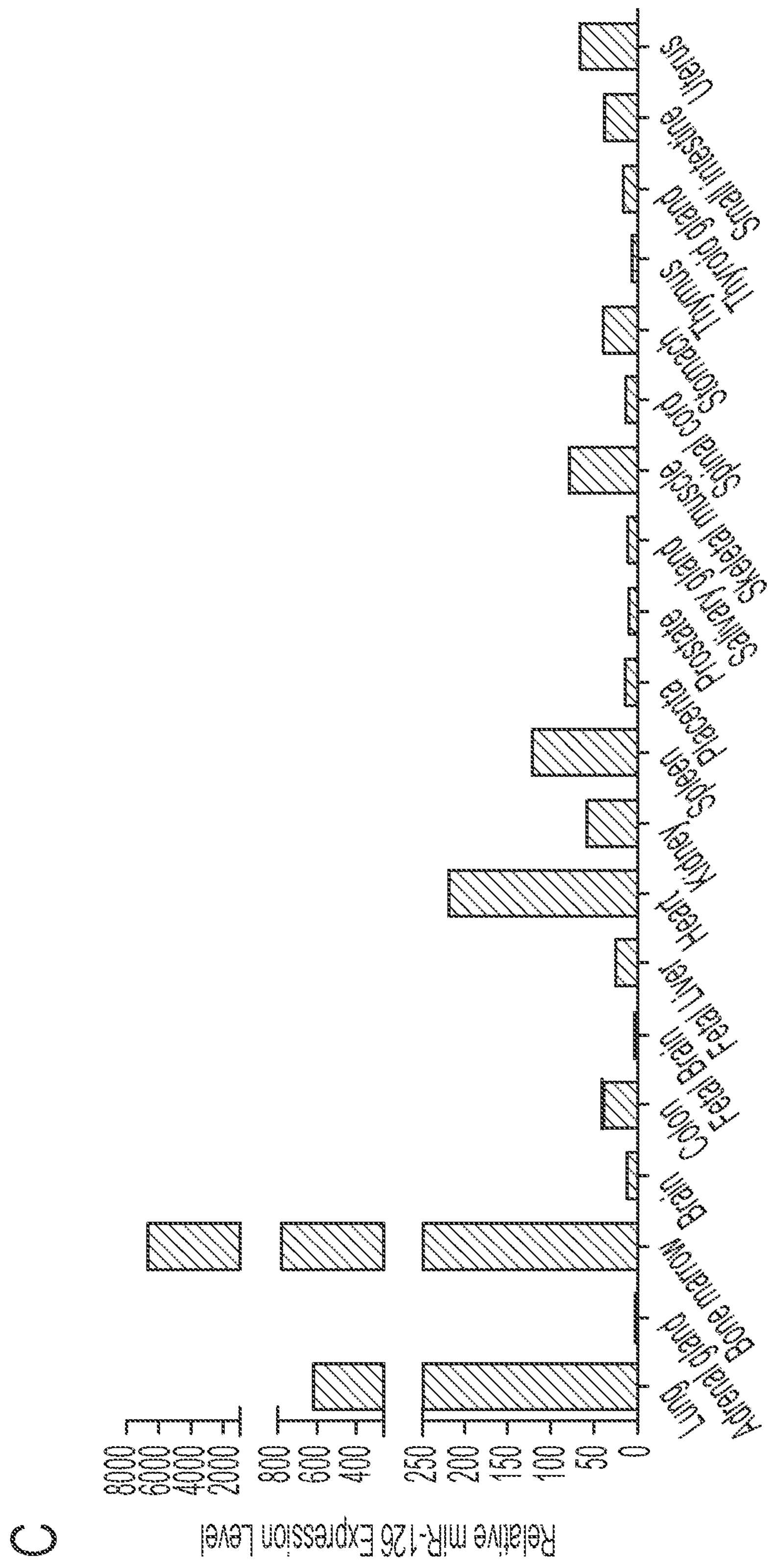

Expression of lncEGFL7OS in human tissues and DCM patients. Given the involvement of EGFL7/miR-126 locus in regulating angiogenesis, the inventors focused on lncEGFL7OS, which partially overlaps with EGFL7/miR-126 gene but is transcribed in opposite direction (FIG. 2A)[33,38]. The existence of lncEGFL7OS was confirmed by RT-PCR cloning using human placental RACE-ready cDNAs and subsequent sequencing, and the size of lncEGFL7OS is consistent with deposited gene AF161442 (FIG. 11A). Interestingly, conserved homologous sequence of lncEGFL7OS only exists in humans and primates Rhesus monkey, but not in other lower vertebrate species including mice, suggesting lncEGFL7OS is an evolutionarily new gene in mammals. The inventors performed qRT-PCR to examine the tissue expression pattern of lncEGFL7OS. LncEGFL7OS was found to be highly enriched in the human lung, placenta and heart, which are highly vascularized tissues (FIG. 2B). Since lncEGFL7OS overlaps with EGFL7, miR-126, the expression of EGLF7 and miR-126 was also examined in parallel to lncEGFL7OS. Human EGFL 7 has four isoforms, named as EGFL7A-D, but only EGFL7B and EGFL7C are detectable by RT-PCR in human tissues. By qRT-PCR, both EGFL7B and EGFL7C are enriched in heart, kidney, bone marrow, uterus, thymus, thyroid, small intestine and placenta. Besides that, EGFL7B is more enriched in prostate, while EGFL7C is more enriched in lung and brain, suggesting a differential expression pattern of EGFL7 isoforms in humans (FIG. 11B). miR-126 is highly enriched in the bone marrow, lung and heart (FIG. 11B). Taken together, these results suggest there are both common and differential expression pattern of lncEGFL7OS and EGFL7/miR-126 in different human tissues.

The inventors also examined the subcellular localization of lncEGFL7OS using both semi-quantitative RT-PCR and high-resolution RNA fluorescence in situ hybridization (FISH). By RT-PCR, lncEGFL7OS was shown to be expressed in both the cytoplasm and nucleus, but more in the nucleus of HUVECs (FIG. 2C). SENCR was used a marker for cytoplasmic-enriched lncRNA, while NEAT-1 was used as a marker for nuclear enriched-lncRNA[31,39]. These results were confirmed by high-resolution RNA FISH experiment. RNA FISH with single-molecule sensitivity was performed using oligonucleotide (oligo) probe pools specific for lncEGFL7OS[40]. The inventors observed variable numbers of lncEGFL7OS molecules in both the nucleus and cytoplasm of HUVECs (FIG. 2D). RNaseA-treated samples were used as negative control and adeno-lncEGFL7OS-overexpressed HUVECs were used as positive control for specificity of the probe. By quantification, the average copy number of lncEGFL7OS RNA in HUVECs is ~19, which is in agreement with the copy number (23-28 copies) by qRT-PCR using in vitro transcribed lncEGFL7OS as control for copy number calculation (data not shown). Taken together, these data indicate that lncEGFL7OS is expressed at relatively low copy numbers in both the nucleus and cytoplasm of HUVEC cells.

Figure 2E:
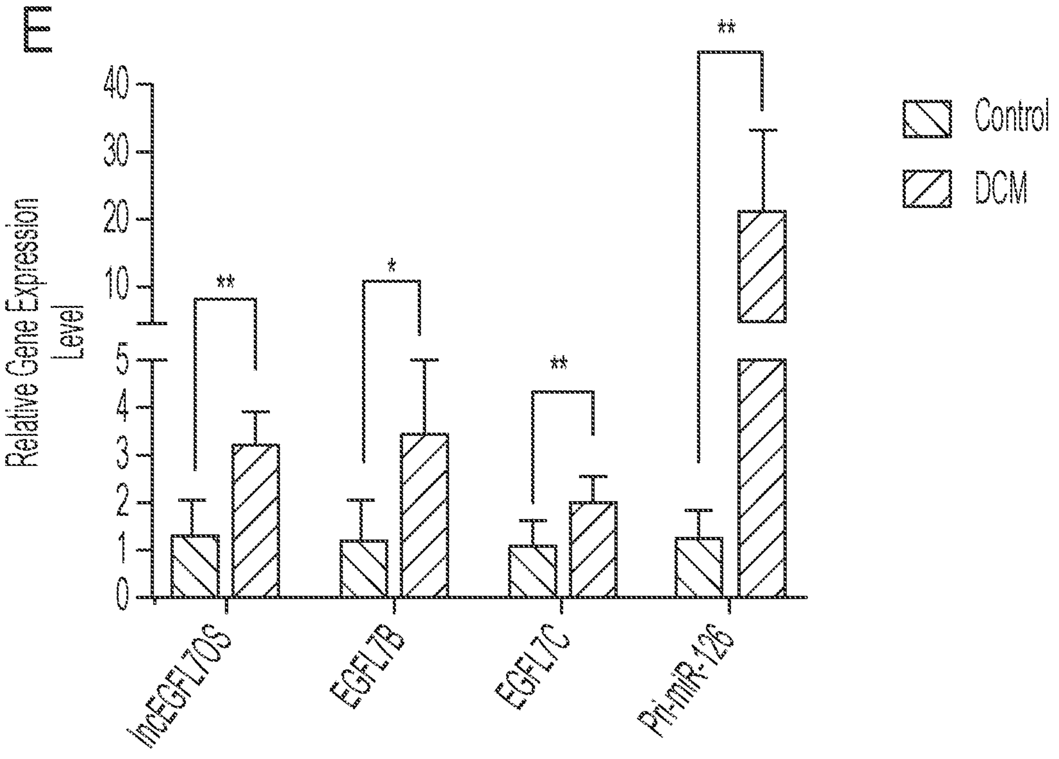
Figure 11D:
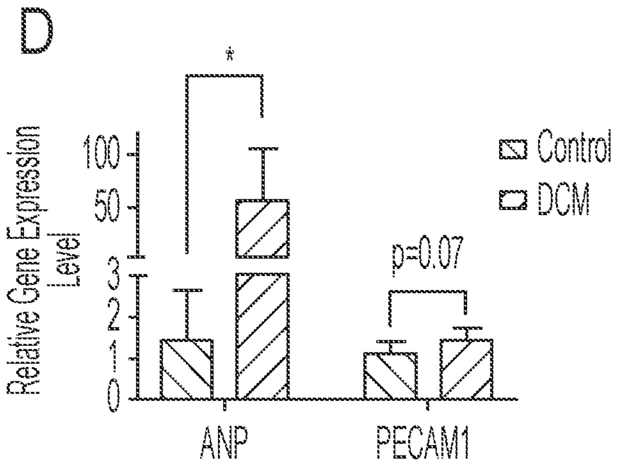

To study the involvement of lncEGFL7OS in cardiovascular disease, the inventors asked whether lncEGFL7OS expression correlates with human dilated cardiomyopathy (DCM), a disease with defective vascularization[2-4]. Increased expression of proangiogenic factors, including hypoxia-inducible factor 1α (HIF-1α) and VEGF-A, have been found in DCM, likely due to the compensatory angiogenesis and/or increased mobilization of endothelial progenitor cells (EPCs) to the diseased heart[2] The expression of lncEGFL7OS was examined by qRT-PCR in the hearts of 7 DCM patients, with 5 healthy hearts used as controls. In the DCM hearts, the expression of atrial natriuretic peptide (ANP), a prominent marker for heart failure, was drastically upregulated (FIG. 11D). In line with the increased angiogenic factors, the expression of EC/EPC marker PECAM-1 was also marginally increased. The inventors found lncEGFL7OS expression was significantly elevated in the hearts of DCM patients (FIG. 2E). Interestingly, the expression of EGFL7B and EGFL7C, as well as pri-miR-126, was also significantly upregulated in the hearts of DCM patients.

Figure 2F:
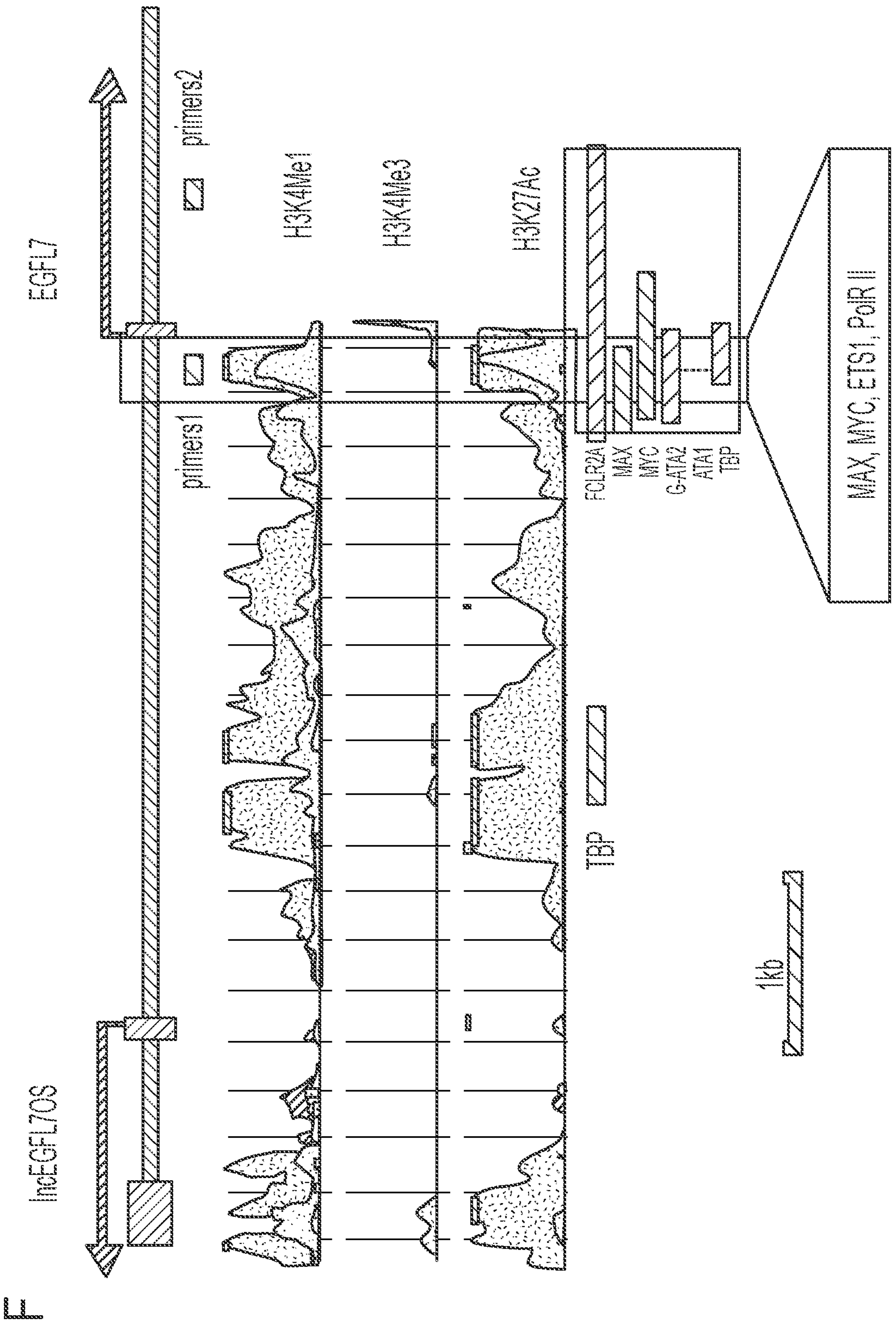

Regulation of lncEGFL7OS expression by ETS factors through a bidirectional promoter in HUVECs. To dissect the lncEGFL7OS regulation mechanism in relation to its host gene EGFL7/miR-126, the inventors aimed to identify the potential regulatory elements for lncEGFL7OS. They have analyzed the cell type-specific active element of the locus from online database UCSC genome browser (FIG. 2F). A critical regulatory element is located on EGFL7B promoter between lncEGFL7OS and EGFL7/miR-126. Bioinformatics data from ENCODE indicate that LncEGFL7OS DNA contains a region positive for epigenetic marks including histone H3 trimethylated lysine 4 methylation (H3K4Me1) and H3K27Ac (mark poised and active enhancers), H3K4Me3 (marks promoter of protein coding genes), and binding sites for transcription factors MAX, MYC and RNA Polymerase (PoIR) II. Several binding sites for ETS transcription factors were found in region. The inventors have shown that its homologous region drives the EC-enriched LacZ reporter gene expression in mice[34]. Consistently, chromatin immunoprecipitation (ChIP) PCR assay using antibodies against MAX/MYC, RNA Pol II and histone H3 trimethylated lysine 4 (H3K4me3) demonstrated the binding of these factors specifically to the region but not a non-relevant nearby region, indicating that this region is transcriptional active (FIG. 11E). Additional potential promoters were not found in the region between lncEGFL7OS and EGFL7 transcripts by bioinformatics approach. Instead, CpG islands were found in the region. CpG islands in mammalian promoter regions tend to show bidirectional promoter activity[41]. Bidirectional promoters have been proposed to drive head-to-head gene transcription involving ncRNAs[42]. Based on these, the inventors tested a novel hypothesis that a bidirectional promoter (lncEGFL7OS/EGFL7/miR-126 promoter) regulated by ETS factors drives the expression of both lncEGFL7OS and EGFL7/miR-126 in human ECs. The putative lncEGFL7OS promoter was cloned into a promoter-less luciferase reporter construct in either sense or anti-sense direction. By luciferase assay, the promoter in either direction exhibited similar activity under baseline in 293T cells (FIG. 2G). Moreover. ETS1 transcription factor significantly activated the promoter activity in either direction, while the ETS1mut that lacks the DNA binding domain showed significantly reduced activation of the promoter[34]. ETS factors have been shown to regulate miR-126 expression in ECs[43]. To further test whether ETS factors are required to regulate lncEGFL7OS expression, ETS1 and ETS2 genes were silenced in HUVEC cells, and lncEGFL7OS and pri-miR-126 expression were examined by qRT-PCR. Both genes were significantly reduced by ETS1/2 silencing, suggesting ETS factors control the expression of both lncEGFL7OS and EGFL7/miR-126 (FIG. 2H).

Regulation of angiogenesis by lncEGFL7OS in vitro and in vivo. To define the potential role for lncEGFL7OS in angiogenesis, the inventors performed EC-fibroblast co-culture assays after silencing lncEGFL7OS using two independent siRNAs in HUVEC cells[44] (FIGS. 12A-B). When ECs are cultured on the top of a confluent fibroblast cell layer, ECs will proliferate to form "islands" of ECs, and then sprout to form three-dimensional vascular tubules resembling capillaries which can be visualized by immunostaining with an antibody to EC-enriched human PECAM-1 (FIG. 3A). Of note, control siRNA has a mild but not significant effect in angiogenesis in this model. Compared to the control siRNA, si-lincEGFL7 #1 or si-lncEGFL7OS #2 significantly repressed the formation of vascular tubules at 7 days after co-culture as shown by PECAM-1 staining and the subsequent quantification of the vascular tube length (FIGS. 3A-B). Taken together, the inventors conclude that lncEGFL7OS is required for proper angiogenesis in vitro.

Figure 12C:
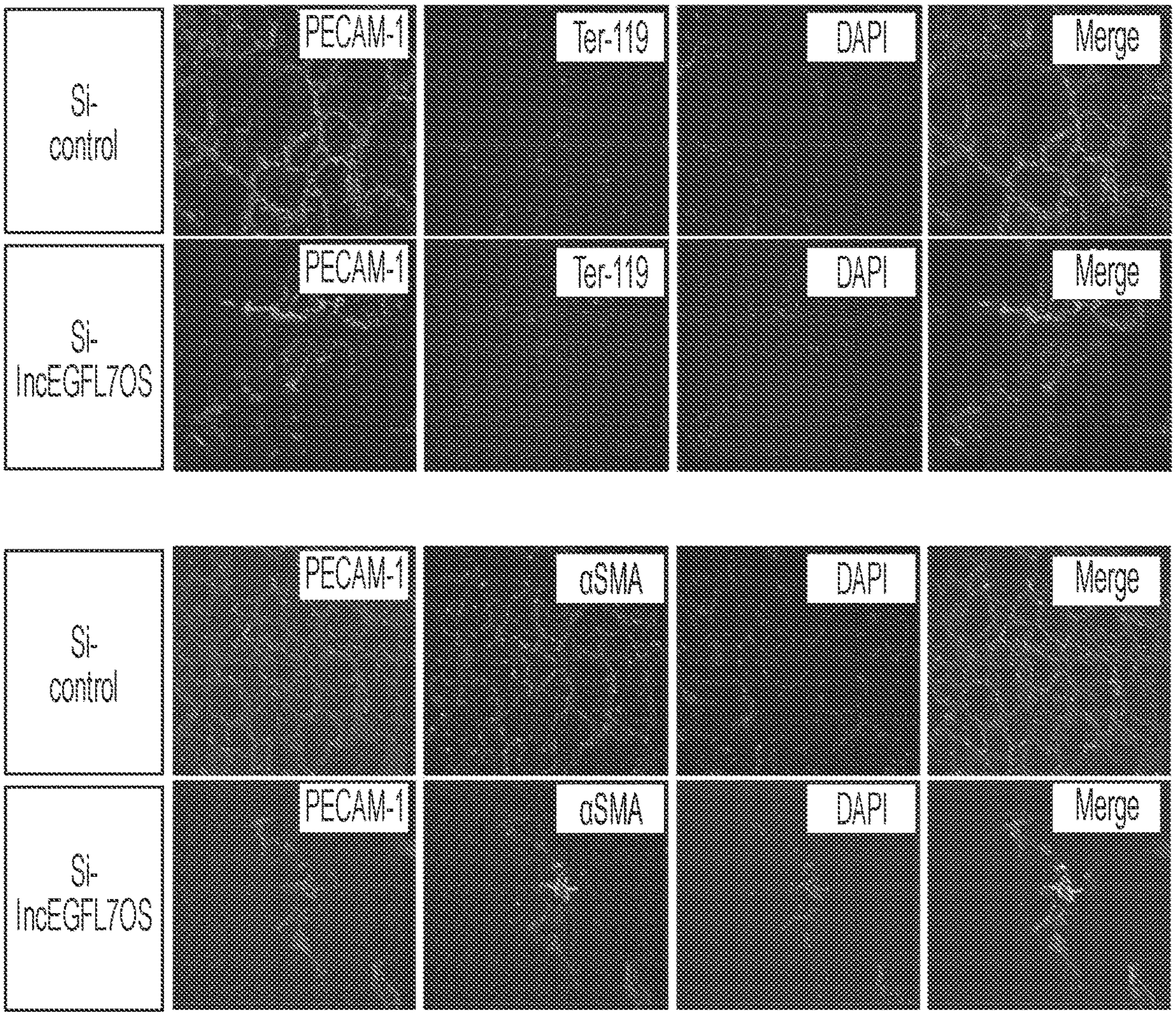

To examine the requirement of lncEGFL7OS in vasculogenesis/angiogenesis in vivo, si-lncEGFL7OS or control transfected HUVEC cells were mixed with Matrigel and injected subcutaneously on the back midline of nude mice, and the primary vascular network was stained with antibody against human PECAM-1 at 14 days after Matrigel implantation. Compared to the well-connected vessel structure in the controls, fewer networking was observed in the lncEGFL7OS-silenced EC group (FIGS. 3C-D). Red blood cells and smooth muscle cells recruiting was detected in the formed vessels as proved by co-staining of human PECAM-1 and mouse Ter-119 (red blood cell marker) or mouse α-SMA (smooth muscle marker) staining, which suggests functionality of the vessels (FIG. 3C; FIG. 12C). These results indicate that lncEGFL7OS is required for proper angiogenesis in vivo.

Figure 3H:
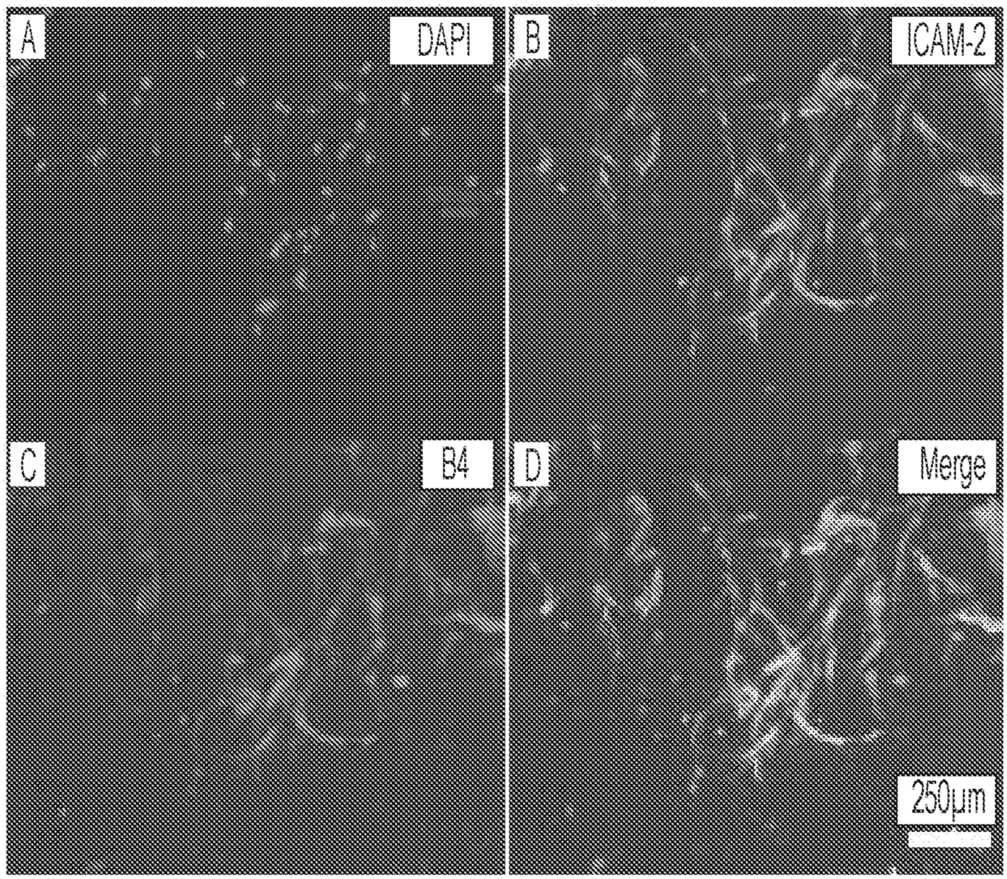

To directly test the function of lncEGFL7OS in angiogenesis in human tissues, the inventors developed a unique human choroid sprouting assay based on a previous publication[45]. Briefly, human choroids were dissected from the donor eyes from the eye bank and were cut into approximately 4 $mm^2$ pieces and transfected with control or lncEGFL7OS siRNAs ovemight. The choroids were then seeded in the Matrigel and cultured in EGM-2 medium for up to 10 days. Silencing of lncEGFL7OS by siRNAs (a mix of siRNA #1 and 2 at half concentration used for other assays) in the system was confirmed by qRT-PCR (FIG. 3E). In the control choroid, significant sprouting was observed at day 10 with an average distance of ~1200 μm (FIG. 3F). Compared to the control, lncEGFL7OS siRNAs drastically repressed human choroid sprouting, establishing a critical role for lncEGFL7OS in angiogenesis in human tissues (FIGS. 3F-G). The EC identity of the sprouting cells was confirmed by ICAM-2 and isolectin B4 co-staining (FIG. 3H).

Figure 4A:
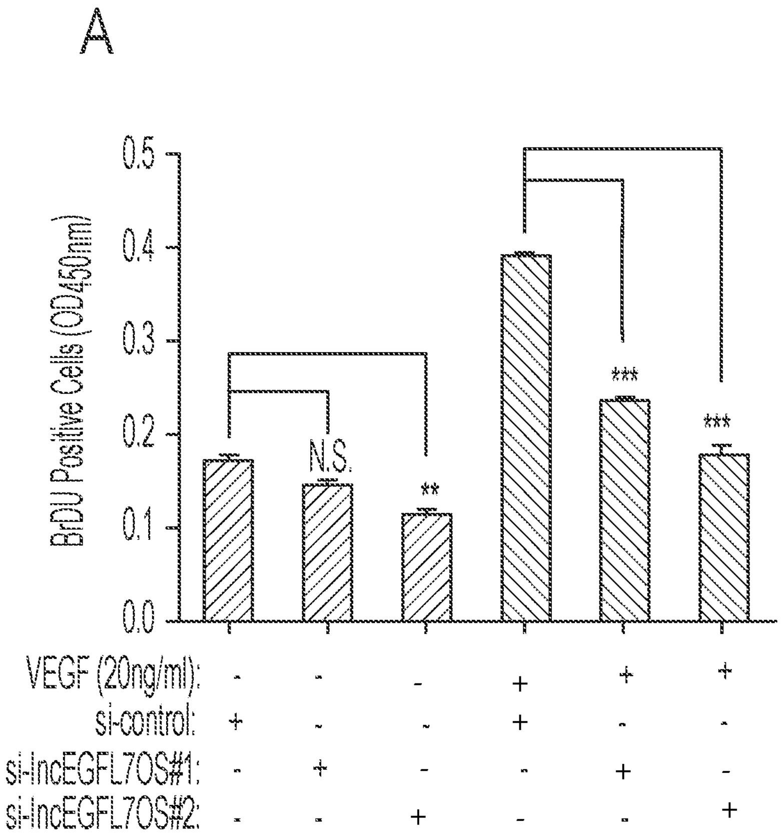
Figure 4B:
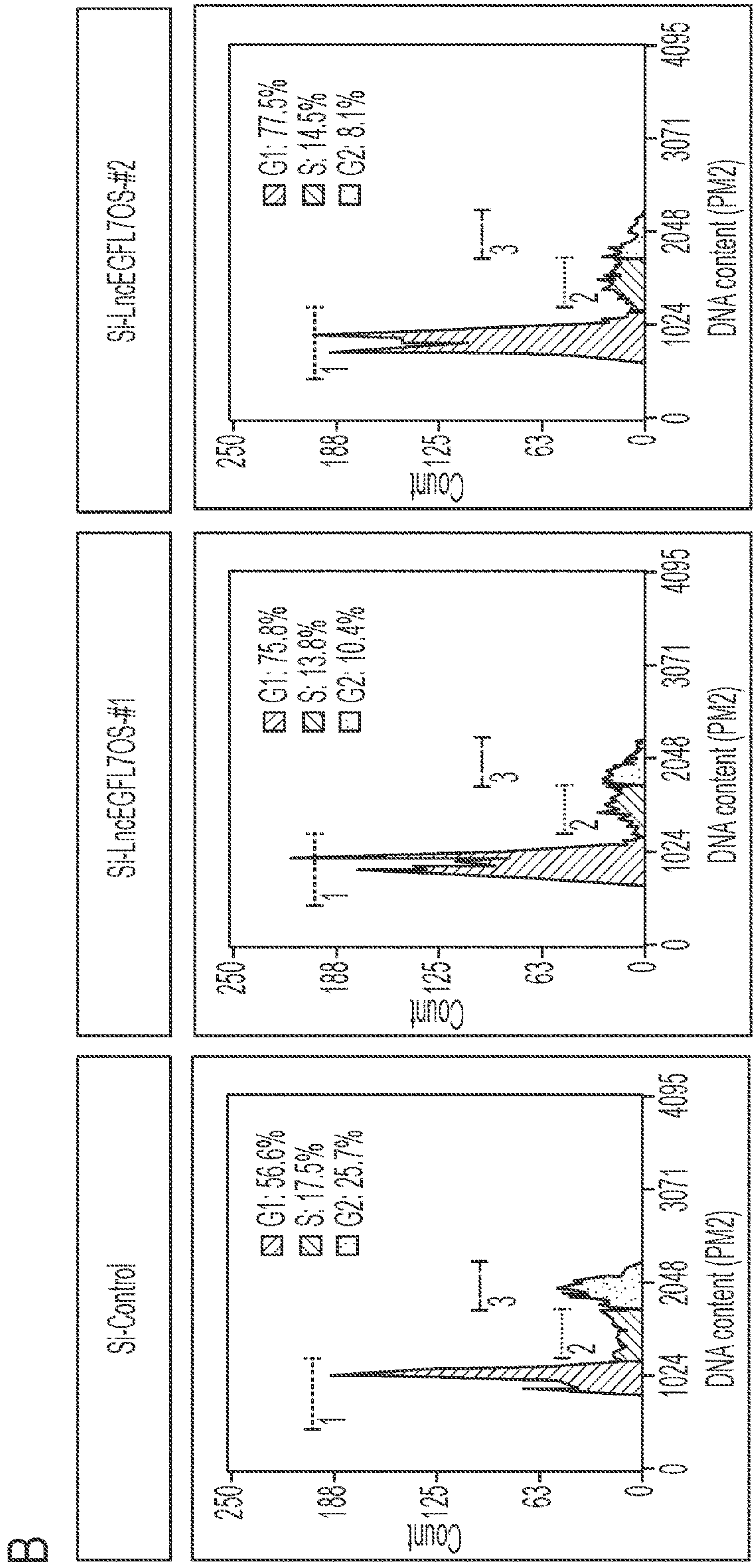
Figure 4C:
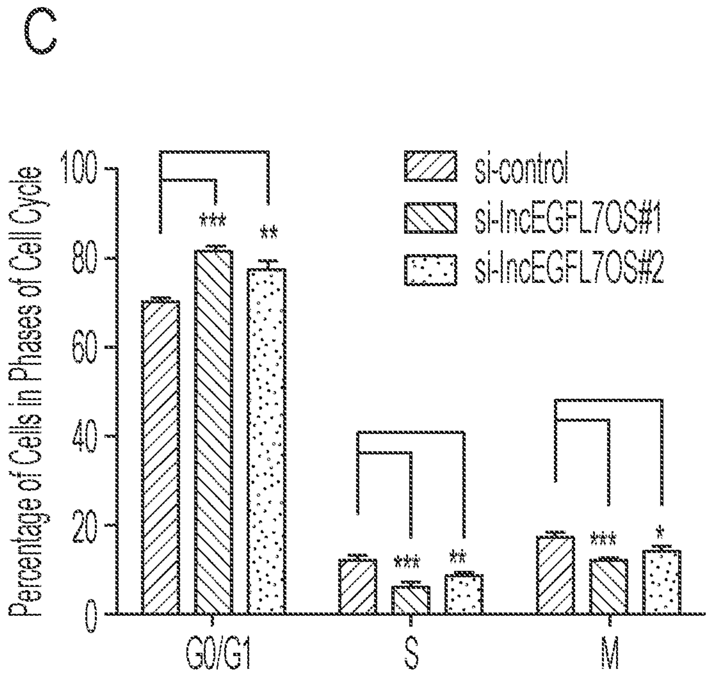

Regulation of EC proliferation and migration by lncEGFL7OS in vivo. To dissect the cellular mechanism whereby lncEGFL7OS regulates angiogenesis, a BrDU incorporation assay was carried out to analyze EC proliferation upon lncEGFL7OS silencing. Under starvation condition, si-lincEGFL7 #2 significantly decreased EC proliferation as shown by BrdU incorporation compared to the random control, while the effect from si-lncEGFL7OS #1 was not statistically significant (FIG. 4A). However, the EC proliferation induced by VEGF treatment was significantly repressed by either si-lncEGFL7OS #1 or si-lncEGFL7OS #2. To further characterize the reduced EC proliferation after lncEGFL7OS knockdown, the cell cycle profile was quantified after flow cytometry under normal culture conditions. A significant increase in the percentage of cells in the G0/G1 phase was observed upon lncEGFL7OS knockdown (FIGS. 4B-C). Accordingly, cells in the S and G2/M phase are significantly decreased. This indicates a G1 arrest in the si-lncEGFL7OS treated cells. The inventors also determined whether EC migration is affected by lncEGFL7OS knockdown. Using a scratch wound assay, the inventors found that compared to the control, lncEGFL7OS silencing significantly repressed EC migration in response to VEGF treatment after wound scratch (FIGS. 4D-E). To assess whether lncEGFL7OS silencing results in EC death, TUNEL assay was performed. In the control condition, ~0.4% of EC cells undergo cell death, silencing of lncEGFL7OS by siRNA #1 and #2 significantly increased EC death to ~0.55% and ~0.64%, respectively (FIG. 13E). Therefore, the increase of EC death by si-lncEGFL7OS is statistically significant, but probably not biologically important with regard to the angiogenic phenotypes observed. These results indicate that lncEGFL7OS is required for proper EC proliferation and migration in vitro.

Overexpression of lncEGFL7OS enhances angiogenesis in an EC/Fibroblast co-culture angiogenesis model. The inventors further examined whether overexpression of lncEGFL7OS in ECs enhances angiogenesis. To do so, lncEGFL7OS or control LacZ adenoviruses were generated, and used to infect HUVEC cells at multiplicity of infection at 50. Infected ECs were cultured on a fibroblast mono layer, and their angiogenic response was examined by staining with an antibody to PECAM-1 at 7 days after co-culture. The efficiency of the virus was verified by qRT-PCR. Over 2000-fold lncEGFL7OS was achieved in ECs after virus infection (FIG. 13A). No significant differences were observed in Ad-lacZ infected samples compared to noninfection controls. LncEGFL7OS overexpression enhanced angiogenesis as shown by the significantly increased total tube length compared to the controls (FIGS. 13B-C). These data indicate that overexpression of lncEGFL7OS is sufficient to enhance EC angiogenesis.

Figure 5C:
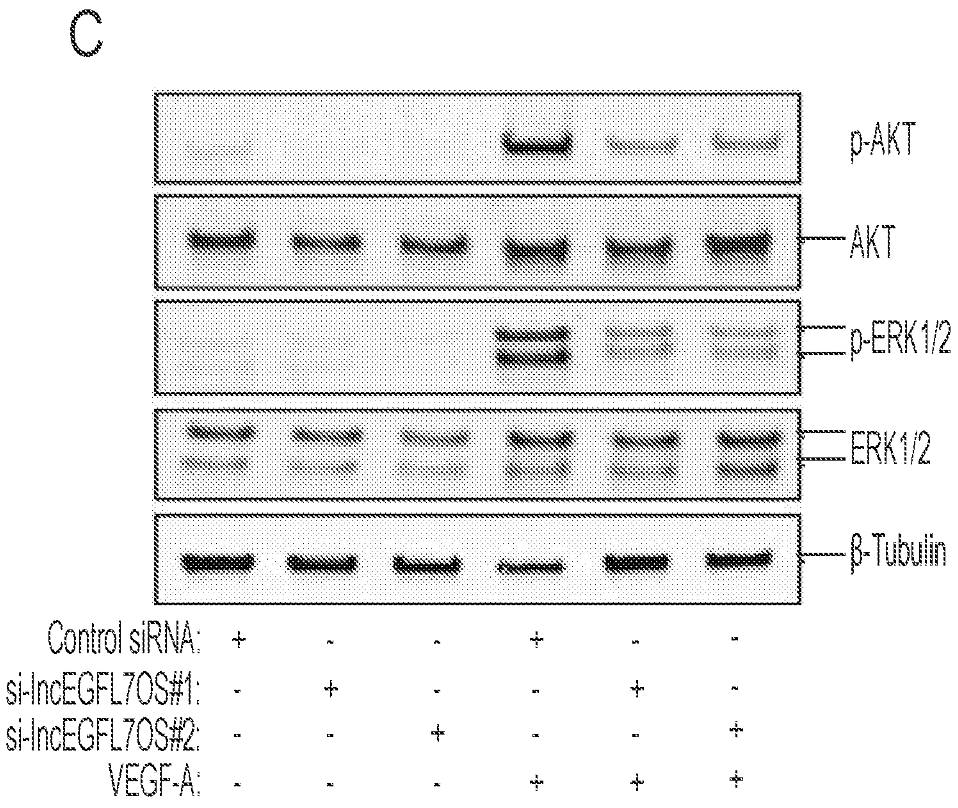
Figure 5D:
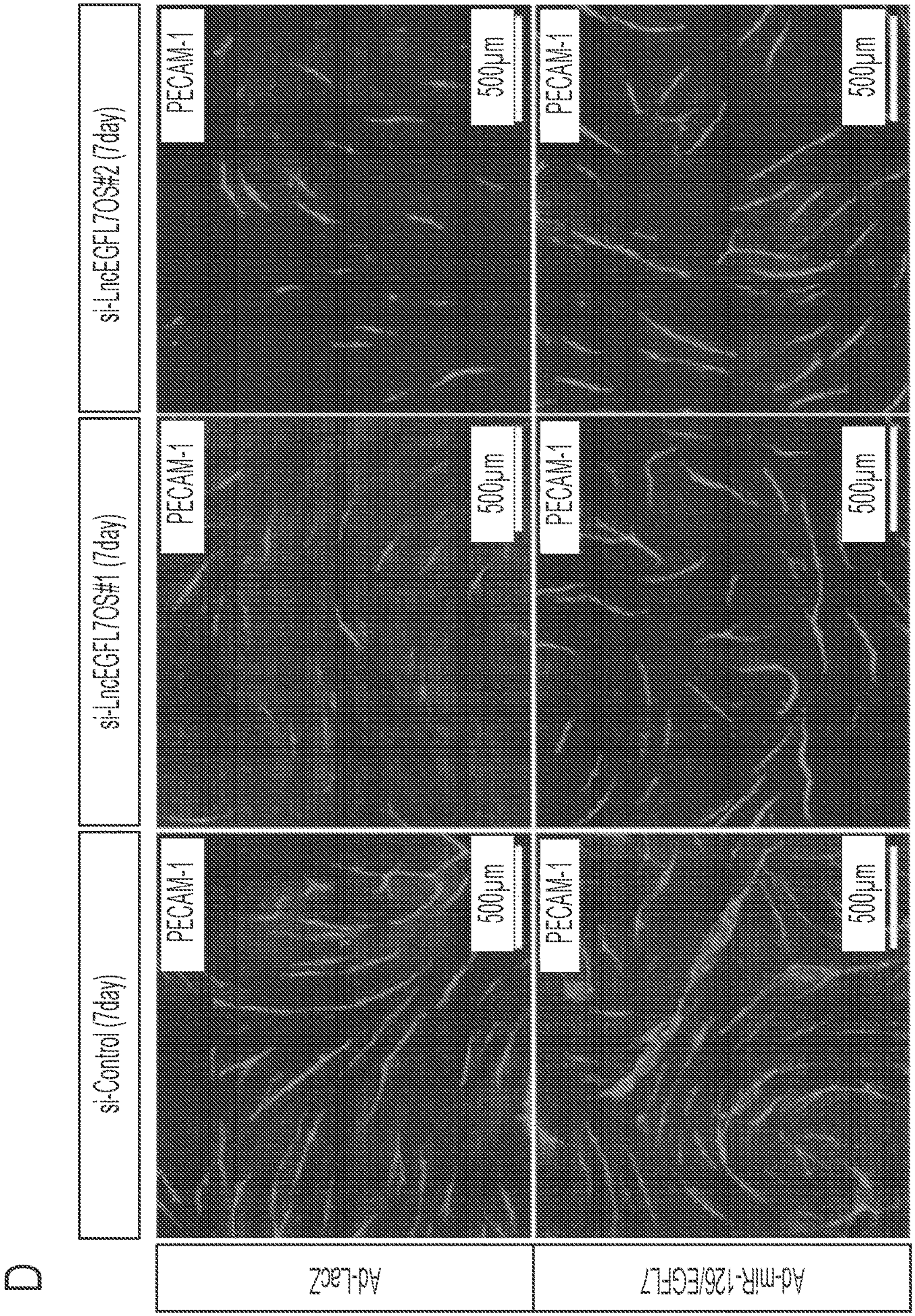
Figure 5E:
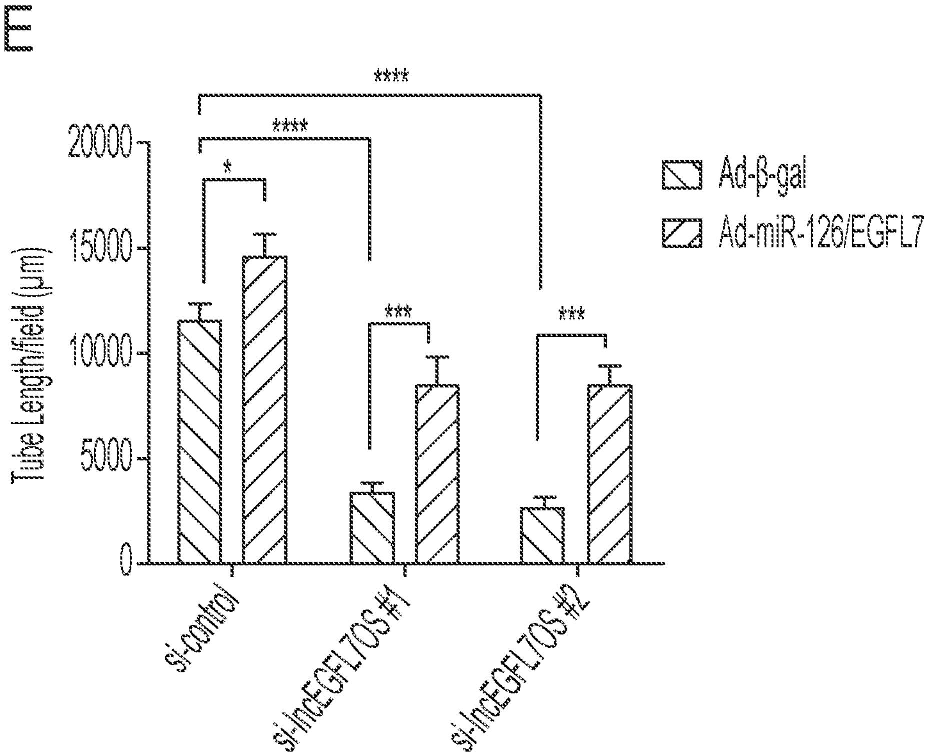

Regulation of EGFL7/miR-126 expression by lncEGFL7OS. lncRNAs could exert regulatory function in cis on the neighboring genes in the nucleus[30]. Since lncEGFL7OS is located in the opposite strand neighboring EGFL7/miR-126, the inventors surmised that lncEGFL7OS regulates angiogenesis by controlling EGFL7/miR-126 expression. The expression of EGFL7B-C and miR-126 was examined by qRT-PCR upon lncEGFL7OS knockdown. As shown in FIG. 5A, EGFL7B and C expression was dramatically decreased upon lncEGFL7OS knockdown. The downregulation of EGFL7 at protein level by lncEGFL7OS knockdown was confirmed by Western blot analysis (FIG. 14C). Similarly, the expression of both miR-126 and miR-126*, a microRNA located in the intron of EGFL7 gene, is also downregulated by lncEGFL7OS knockdown (FIG. 5B). miR-126 has been shown to modulate MAP kinase signaling and PI3K-AKT signaling by targeting Spred-1 and PI3KR2, respectively[33-35]. Consistent with the downregulation of miR-126, phosphorylation of ERK1/2 and AKT induced by VEGF was significantly reduced in ECs transfected with si-lncEGFL7OS #1 or si-lncEGFL7OS #2 compared to the controls (FIG. 5C). The inventors also examined whether lncEGFL7OS overexpression increases the expression of EGFL7 and miR-126. As expected, a ~2-fold upregulation of miR-126 and a ~3-fold increase of EGFL7B were observed when lncEGFL7OS is overexpressed in ECs (FIGS. 14A-B). To determine whether EGFL7 and miR-126 can mediate the angiogenic response of lncEGFL7OS, the inventors tested the capability of miR-126 expressing adenovirus and EGFL7 protein in rescuing the anti-angiogenic phenotype of si-lncEGFL7OS. The combination of miR-126 and EGFL7 enhanced angiogenesis in the wild-type HUVECs and rescued the anti-angiogenic effect of lncEGFL7OS silencing to a great extent in an EC-Fibroblast cell co-culture model (FIGS. 5D-E). These results indicate that lncEGFL7OS is critical for maintaining maximal expression of EGLF7/miR-126, which is required for VEGF signaling and angiogenesis through MAPK and PI3K/AKT pathways.

lncEGFL7OS regulates EGFL7/miR-126 promoter activity by interacting with MAX transcription factor. To study the mechanism whereby lncEGFL7OS regulates EGFL7/miR-126 expression, the inventors hypothesized that lncEGFL7OS regulates EGFL7/miR-126 promoter/enhancer activity by interacting with MAX transcription factor. MAX was predicted as one of the top lncEGFL7OS-interacting proteins by lncRNA interaction prediction program catRAPID[46]. Online database UCSC genome browser predicts the existence of MAX binding sites between lncEGFL7OS and EGFL7/miR-126 genes (FIG. 6A). The inventors first tested whether lncEGFL7OS interacts with MAX protein in ECs. RNA immunoprecipitation (RIP) assays showed that lncEGFL7OS RNA was pulled down in the nuclear lysate by a Chip-grade antibody to MAX, and this interaction was increased by lncEGFL7OS overexpression (FIG. 6B). To dissect the domains in lncEGFL7OS that interact with MAX, lncEGFL7OS was separated into three fragments according to the predicted secondary structure (FIG. 6C). Three different fragments (F1 to F3) were cloned into expression vectors and transfected into RPE cells that have undetectable endogenous lncEGFL7OS expression. Similar RIP RT-PCR assays demonstrated that F1 fragment in the 5' end of lncEGFL7OS is the major domain that interacts with MAX protein (FIG. 6D).

The inventors further examined whether MAX protein binds to the bidirectional lncEGFL7OS/EGFL7/miR-126 promoter/enhancer. ChIP-PCR assays confirmed the specific binding of MAX to this region in ECs (FIG. 6E). Moreover, overexpression of lncEGFL7OS significantly increased MAX binding to this region. As control, MAX protein was not enriched in a non-relevant control DNA region (FIG. 15A). MAX has been shown to dimerize with MYC and stimulate histone acetylation and gene transcription[47]. The inventors' co-immunoprecipitation assay confirmed the interaction of MAX with p300, a component in the p300/CBP co-activator complex that has intrinsic histone acetyltransferase activities, in ECs (FIG. 15B). The inventors therefore determined whether acetylated H3K27 (H3K27ac), a marker for active enhancer, is enriched in this region, and found H3K27ac was indeed enriched in the region, and this enrichment was further increased by lncEGFL7OS overexpression (FIG. 6F). To confirm whether the interaction of lncEGFL7OS with MAX is required for angiogenesis, lncEGFL7OS-F (2+3) that does not contain the F1 region was cloned and used to make adenovirus. Overexpression of lncEGFL7OS-F (2+3) by adenovirus neither affected EGFL7B and miR-126 expression, nor impacted angiogenesis in an EC-fibroblast co-culture assay (FIGS. 15C-F), suggesting the requirement of lncEGFL7OS/MAX interaction in angiogenesis. Together, these results suggest that lncEGFL7OS promotes the binding of MAX protein to the bidirectional promoter/enhancer region of lncEGFL7OS/EGFL7/miR-126, and enhances their transcription, and therefore angiogenesis.

To examine whether MAX is required for regulating lncEGFL7OS/EGFL7/miR-126 expression, two specific siRNAs were used to silence MAX expression (FIG. 6G). MAX silencing resulted in significantly decreased expression of EGFL7, lncEGFL7OS and miR-126 (FIGS. 6H-J). Consistently, MAX silencing led to repressed angiogenesis as shown by EC-Fibroblast co-culture assays (FIG. 6K). The inventors further determine whether MAX silencing overrides the increased expression of miR-126 induced by adenovirus expressing lncEGFL7OS. As shown in FIG. 6L, the induction of miR-126 expression by lncEGFL7OS overexpression was blunted by MAX knockdown. To determine whether lncEGFL7OS is required for MAX recruiting to the EGFL7/nmiR-126 promoter/enhancer, similar ChIP-PCR was performed after lncEGFL7OS knockdown. As shown in FIGS. 7A-B, silencing of lncEGFL7OS significantly reduced MAX binding to the EGFL7/miR-126 promoter/enhancer as well as H3K27 acetylation at the locus. Together, these data indicate that lncEGFL7OS regulates EGFL7/miR-126 expression by interaction with MAX transcription factor, which enhances H3K27 acetylation in the lncEGFL7OS/EGFL7/miR-126 enhancer/promoter region.

Since lncEGFL7OS interacts with MAX, the inventors asked whether other known MAX target genes, including Cyclin D2 and DHFR, are regulated by lncEGFL7OS[48,49] These two genes were confirmed to be MAX targets in ECs by siRNA experiments and ChIP assays (FIGS. 7C-D and FIGS. 7G-H). Overexpression of lncEGFL7OS enhanced the expression of Cyclin D2 and DHFR (FIGS. 7E-F), which could be explained by the increased binding of MAX and increased H3K27 acetylation at their respective promoters (FIGS. 7G-J). However, neither Cyclin D2 nor DHFR expression was repressed by lncEGFL7OS knockdown (FIGS. 7K-L). These data suggest that, although lncEGFL7OS is capable of regulating other MAX target genes when overexpressed, lncEGF7OS does not act in trans to regulate angiogenesis through MAX under normal conditions.

Figure 8A:
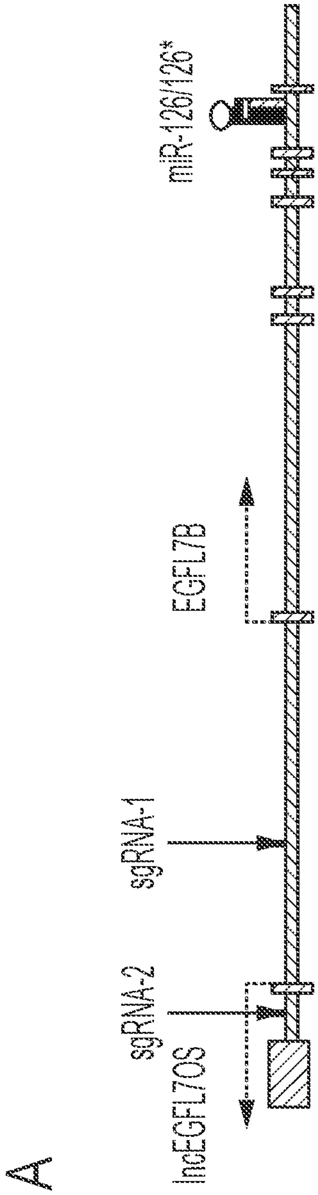
Figure 8B:
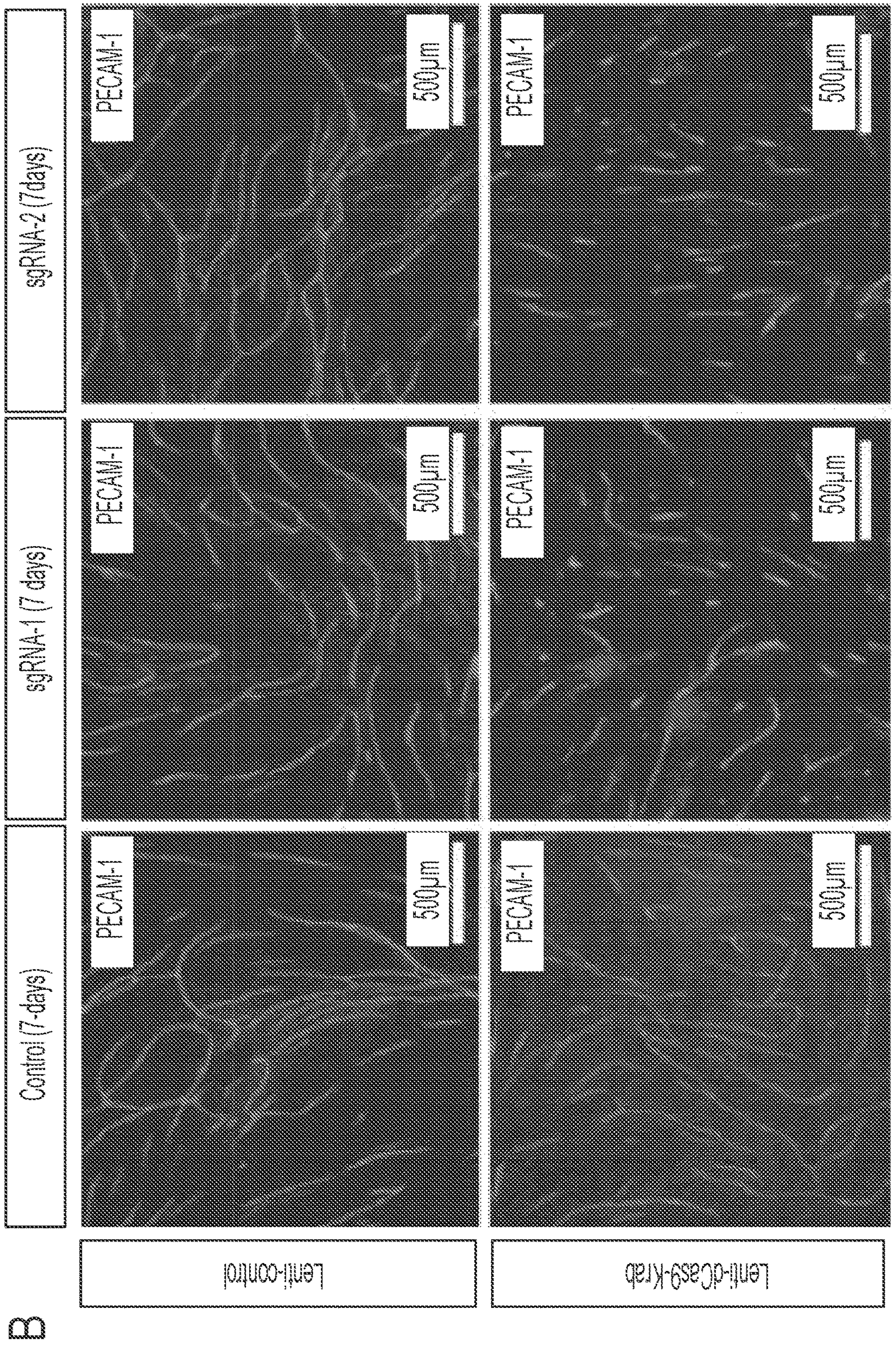

Inhibition of angiogenesis by CRISPR-mediated targeting of the EGFL7/miR-126/lncEGFL7OS locus. To further study the regulatory mechanism and the therapeutic targeting potential of the EGFL7/miR-126/1lncEGFL7OS locus, a dCas9-KRAB system, in which a catalytically inactive Cas9 is fused to KRAB transcriptional repressor, was utilized to test the effect of silencing this locus on angiogenesis[50]. Two guide RNAs (sgRNAs), with one targeting the genomic region between the EGFL7B and lncEGFL7OS transcription start sites and the other targeting the lncEGFL7OS intron region, were designed to guide sequence-specific transcription repression mediated by dCas9-KRAB (FIG. 8A). By EC-fibroblast co-culture assay, lentivirus expressing sgRNA-1 or sgRNA-2 significantly repressed EC angiogenesis only when dCas9-KRAB was co-expressed (FIGS. 8B-C). Of note, Lenti-dCas9-KRAB alone did not significantly impact angiogenesis, ruling out the potential side-effects of dCas9-KRAB overexpression. When gene expression near this locus was examined, the expression of EGFL7B, miR-126 and lncEGFL7OS was drastically repressed by sgRNA-1, and to a less extent by sgRNA-2 (FIG. 8D). These data support the co-regulation of EGFL7/miR-126 and lncEGFL7OS in the locus and suggest the potential of therapeutic targeting angiogenesis by simultaneously targeting these three genes using a CRISPR-mediated approach.

Example 3—Discussion

Figure 9:
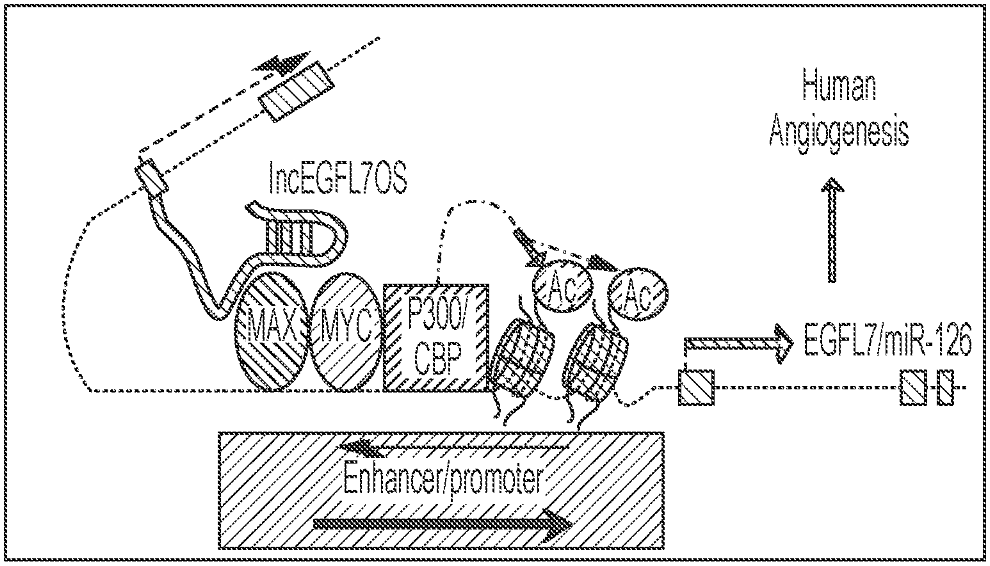
FIG. 9. A model for lncEGFL7OS in human angiogenesis. LncEGFL7OS is transcribed in the opposite strand of EGFL7/miR-126 gene under the control of an ETS transcription factors-regulated bidirectional promoter. In turn, lncEGFL7OS transcripts recruit MAX, which interacts with p300 and increase the acetylation of Histone H3K27. This in turn enhances the transcription of EGFL7/miR-126 gene and therefore angiogenesis through MAPK and AKT pathways in human ECs.

In this study, the inventors have identified ~500 EC-restricted lncRNAs by comparing the lncRNA/mRNA profile from EC and non-EC lines. The EC- or vasculature-restriction of a list of candidate lncRNAs was confirmed by qRT-PCR and bioinformatics approaches. The inventors further reported a human/primate-specific EC-enriched lncEGFL7OS that is located in the opposite strand neighboring the EGFL7/miR-126 gene. Expression of lncEGFL7OS in ECs is regulated by ETS transcription factors through a bidirectional promoter. Silencing of lncEGFL7OS represses EC proliferation and migration, therefore impairing angiogenesis in vitro and human choroid sprouting angiogenesis ex vivo; while overexpression of lncEGFL7OS enhances angiogenesis in ECs. Moreover, CRISPR-mediated targeting of EGLF7/miR-126/lncEGFL7OS locus inhibited angiogenesis, suggesting therapeutic potential of targeting this locus. Upregulation of lncEGFL7OS and EGFL7/miR-126 was observed in the hearts of DCM patients, which may reflect the compensatory vascularization/angiogenesis in DCM. Mechanistically, lncEGFL7OS regulates angiogenic signaling through enhancing EGFL7/miR-126 transcription by interaction with MAX transcription factor, which regulates EGLF7/miR-126/lncEGFL7OS promoter activity (FIG. 9).

Identification of EC-restricted lncRNAs. The inventors' data is consistent with a recent publication that identified EC-restricted lncRNAs[29]. Several lncRNAs, including lncEGFL7OS, HHIP-AS1 and SENCR, were in the short list from both microarrays. The difference from the inventors' results may reflect the different cell types used in the microarrays. The inventors found 498 lncRNAs are enriched in three different primary EC lines compared to non-EC lines using a cutoff of 2. By hierarchical cluster analysis, lncRNA-based clustering appeared to be a stronger classifier for EC lines than mRNA clustering. This is consistent with the general perception that lncRNAs exhibit better tissue specificity than mRNAs[51]. They also found significant variability in lncRNA expression among EC lines, consistent the observed heterogeneity among ECs. Given the central importance of ECs in vascular biology, this dataset may provide a foundation to study the regulation and function for lncRNAs in various vascular development and disease models. Of note, the inventors also found many lncRNAs are highly expressed in ECs, but those lncRNAs are not necessarily EC-specific (data not shown). Those lncRNAs may also important function in cell types including ECs.

Looking deep into the gene list, 91 lncRNAs of the 498 EC-restricted genes have protein coding genes within 10-kb, and about a third of them showed parallel or inverse expression pattern to the associated genes. Functional enrichment analysis indicates that EC-restricted lncRNAs are associated with genes involved in vascular development. Those lncRNAs may be good candidates for further functional studies.

Evolution of lncEGFL7OS/EGFL7/miR-126 locus. The evolution of EGFL7/miR-126 locus exemplifies the evolution of the vascular system. EGFL7 encodes an EGF-like domain containing protein that is specifically secreted by vascular ECs[37]. It is conserved among vertebrates but an orthologue is also found in *Drosophila melanogaster* (CG7447)[52]. miR-126 and miR-126* are encoded by the intron of EGFL7, and are conserved from Fugu in vertebrates to *Homo sapiens*[34]. They are the only miRNAs that are known to be specifically in EC lineage and hematopoietic stem cells. Loss-of-function studies in mice and zebrafish revealed an important function of miR-126 in governing vascular integrity and angiogenesis[33,34]. Egfl7$^{-/-}$ mice display similar vascular abnormalities to MiR126$^{-/-}$ mice, including edema, defective cranial vessel and retinal vascularization[38]. However, an independent study suggests that the vascular phenotype of Egfl7$^{-/-}$ mice could be attributed to the MiR126 deletion (or downregulation) in the mice[35]. The important regulatory function of miR-126 in vascular integrity and angiogenesis is correlated with its appearance during the evolution of vascular system in vertebrates. Besides, miR-126 also has documented functions in vascular inflammation, as well as innate and adaptive immunity[53-55]. That also correlates with the evolutionary innovation of adaptive immune system in vertebrates. These support an important function of EGFL7/miR-126 locus from the evolutionary point of view. To further dissect the function and regulation of the locus during evolution from vertebrates to humans, the inventors identified lncEGFL7OS, which is located in the opposite strand neighboring the EGFL7/miR-126 gene. It only exists in humans and several other primates, including rhesus monkeys, but not in other lower vertebrate species including mice. Although they showed significant function of lncEGFL7OS in human angiogenesis, the full spectrum of lncEGFL7OS function remains to be established.

lncEGFL7OS is a human/primate-specific EC-restricted lncRNA required for proper human angiogenesis. The expression of lncEGFL7OS is restricted to ECs and highly vascularized tissues, which is consistent with the expression of its host genes EGFL7 and miR-126. As to its regulatory mechanisms, the inventors found that both lncEGFL7OS and miR-126 are regulated by ETS1/2 factors in ECs through a bidirectional promoter. They found that lncEGFL7OS is required for proper angiogenesis in vitro by using EC-fibroblast co-culture vasculogenesis/angiogenesis assays. Conversely, overexpression of lncEGFL7OS enhances angiogenesis. Using a human choroid sprouting angiogenesis model the inventors developed, they further demonstrated that lncEGFL7OS is required for human sprouting angiogenesis. This study indicates that three different transcripts from the EGFL7/miR-126 locus, including lncEGFL7OS, EGFL7 and miR-126, have important functions in angiogenesis. EGFL7 and miR-126 have been previously shown to regulate angiogenesis[52]. EGFL7 is essential for vascular tube formation during vasculogenesis in zebrafish[37]. The importance of miR-126 in angiogenesis was demonstrated by loss-of-function studies in both mouse and zebrafish. Targeted deletion of miR-126 in mice or miR-126 knockdown in zebrafish resulted in loss of vascular integrity and defective angiogenesis, while overexpression of miR-126 regulates angiogenesis in a cell-type and strand-specific manner[33-35,56]. It is intriguing that, in contrast to EGFL7 and miR-126, lncEGFL7OS represents a human/primate-specific mechanism in regulating angiogenesis, since lncEGFL7OS only exists in human and several other primates. New angiogenesis mechanism through lncEGF7OS has evolved during evolution, which underscores the importance and delicacy of EFGL7/miR-126 locus in angiogenesis. This study also highlights the importance of using human (and/or primate) system to study the mechanism of angiogenesis.

Mechanism of lncEGFL7OS action. The inventors showed that the action of lncEGFL7OS reflects at least partially the regulation of expression of EGFL7 and miR-126, miR-126 has been shown to promote MAP kinase and PI3K signaling in response to VEGF and FGF by targeting negative regulators of these signaling pathways, including Spred-1 and PIK3R2. Consistent with the downregulation of miR-126 by lncEGFL7OS silencing, they found that the phosphorylation of ERK1/2 and AKT in response to VEGF is repressed by lncEGFL7OS silencing. Mechanistically, MAX transcription factor was identified as a lncEGFL7OS interaction protein required for lncEGFL7OS-regulated gene expression and angiogenesis in ECs. Under normal conditions, the lncEGFL7OS/MAX interaction is likely locus dependent since several other MAX target genes were not affected by lncEGFL7OS silencing. This is possibly due to the low expression of lncEGFL7OS. LncEGFL7OS enhances the transcription of EGFL7/miR-126 by binding to MAX protein that is recruited to the bidirectional promoter/enhancer region in EGFL7/miR-126. MAX knockdown blunts the induction of miR-126 by lncEGFL7OS in ECs. MAX transcription factor has been shown to interact with MYC to control cell proliferation and cell death[57]. MYC has been shown to stimulate histone acetylation and gene transcription by recruitment of cAMP-response-element-binding protein (CBP) and p300[47]. Based on the results showing interaction of MAX and p300, the enrichment of H3K27 acetylation by lncEGFL7OS likely result from the recruitment of CBP and P300 by MAX/MYC. Taken together, lncEGFL7OS acts in cis by interacting with MAX transcription factor to enhance H3K7 acetylation and promote EGFL7/miR-126 expression.

Therapeutic implications. Identifying angiogenic mechanisms that are conserved to human is critical for developing therapeutics for human vascular disorders. These studies have demonstrated that lncEGFL7OS is a human/primate-specific lncRNA critical for human angiogenesis. This may be directly translatable for human diseases involving abnormal angiogenesis. These studies showed increased expression of both lncEGFL7OS and EGFL7/miR-126 in the heart of DCM patients. Although the causative role of lncEGFL7OS in DCM is still unclear, lncEGFL7OS upregulation may reflect the compensatory vascularization/angiogenesis in DCM. It would be intriguing to test whether manipulating the lncEGFL7OS/EGFL7/miR-126 axis has therapeutic benefits for DCM patients. AMD is the leading cause of blindness in the elderly, and choroidal neovascularization is a hallmark for wet AMD[58]. Although anti-VEGF agents can markedly improve the clinical outcome of wet AMD, they have been unable to induce complete angiogenesis regression, and only 30-40% of individuals experienced vision improvement after treatment[59,60]. The inventors developed a human choroid sprouting angiogenesis model and showed that silencing of lncEGFL7OS represses human choroid sprouting angiogenesis. It would be appealing to develop and test lncEGFL7OS-based therapy to treat choroidal neovascularization in wet AMD and other vascular disorders in the future. In this regard, these data that CRISPR-mediated targeting of EGLF7/miR-126/lncEGFL7OS locus inhibits angiogenesis could have therapeutic implications in angiogenesis-related diseases. Targeting this locus could be a potent approach for inhibiting angiogenesis than targeting the three genes individually.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

X. REFERENCES

The following references, to the extent that they provide exemplary procedural or other details supplementary to those set forth herein, are specifically incorporated herein by reference.

1 Carmeliet, P. Angiogenesis in health and disease. *Nat Med* 9, 653-660, doi:10.1038/nm0603-653 (2003).

2 Roura, S. et al. Idiopathic dilated cardiomyopathy exhibits defective vascularization and vessel formation. *Eur J Heart Fail* 9, 995-1002, doi:10.1016/j.ejheart.2007.07.008 (2007).

3 Gavin, J. B., Maxwell, L. & Edgar, S. G. Microvascular involvement in cardiac pathology. *J Mol Cell Cardiol* 30, 2531-2540, doi:10.1006/jmcc.1998.0824 (1998).

4 De Boer, R. A., Pinto, Y. M. & van Veldhuisen, D. J. The imbalance between oxygen demand and supply as a potential mechanism in the pathophysiology of heart failure; The role of microvascular growth and abnormalities. *Microcirculation* 10, 113-126, doi:10.1038/sj.mn.7800188 (2003).

5 Yla-Herttuala. S., Bridges, C., Katz, M. G. & Korpisalo, P. Angiogenic gene therapy in cardiovascular diseases: dream or vision? *Eur Heart J* 38, 1365-1371, doi: 10.1093/eurheartj/ehw547 (2017).

6 Brown, D. M. et al. Ranibizumab versus verteporfin for neovascular age-related macular degeneration. *N Engl J Med* 355, 1432-1444, doi:10.1056/NEJMoa062655 (2006).

7 Rosenfeld, P. J. et al. Ranibizumab for neovascular age-related macular degeneration. *N Engl J Med* 355, 1419-1431, doi:10.1056/NEJMoa054481 (2006).

8 Zampros, I., Praidou, A., Brazitikos, P., Ekonomidis, P. & Androudi, S. Antivascular endothelial growth factor agents for neovascular age-related macular degeneration. *J Ophthalmol* 2012, 319728, doi: 10.1155/2012/319728 (2012).

9 Hurwitz, H. et al. Bevacizumab plus irinotecan, fluorouracil, and leucovorin for metastatic colorectal cancer. *N Engl J Med* 350, 2335-2342, doi:10.1056/NEJMoa032691 (2004).

10 Miller, K. et al. Paclitaxel plus bevacizumab versus paclitaxel alone for metastatic breast cancer. *N Engl J Med* 357, 2666-2676, doi:10.1056/NEJMoa072113 (2007).

11 Sandler, A. et al. Paclitaxel-carboplatin alone or with bevacizumab for non-small-cell lung cancer. *N Engl J Med* 355, 2542-2550, doi:10.1056; NEJMoa061884 (2006).

12 Shojaei, F. & Ferrara, N. Antiangiogenic therapy for cancer: an update. *Cancer J* 13, 345-348, doi:10.1097/PPO.0b013e31815a7b69 (2007).

13 Kapranov, P., Willingham, A. T. & Gingeras, T. R. Genome-wide transcription and the implications for genomic organization. *Nature Reviews Genetics* 8, 413-423, doi:Doi 10.1038/Nrg2083 (2007).

14 Gerstein, M. ENCODE leads the way on big data. *Nature* 489, 208-208 (2012).

15 Ecker, J. R. FORUM: Genomics ENCODE explained. *Nature* 489, 52-53 (2012).

16 Wang, S. & Olson, E. N. AngiomiRs—key regulators of angiogenesis. *Curr Opin Genet Dev* 19, 205-211, doi:S0959-437X(09)00071-9 [pii]10.1016/j.gde.2009.04.002 (2009).

17 Ulitsky, I. & Bartel, D. P. lincRNAs: genomics, evolution, and mechanisms. *Cell* 154, 26-46, doi: 10.1016/j.cell.2013.06.020 (2013).

18 Yu, B. & Wang, S. Angio-LncRs: LncRNAs that regulate angiogenesis and vascular disease. *Theranostics* 8, 3654-3675, doi:10.7150/thno.26024 (2018).

19 M, M. K. & Goyal, R. LncRNA as a Therapeutic Target for Angiogenesis. *Curr Top Med Chem* (2016).

20 Michalik, K. M. et al. Long noncoding RNA MALATI regulates endothelial cell function and vessel growth. *Circ Res* 114, 1389-1397, doi:10.1161/CIRCRESAHA.114.303265 (2014).

21 Liu, J. Y. et al. Pathogenic role oflncRNA-MALATI in endothelial cell dysfunction in diabetes mellitus. *Cell Death Dis* 5, e1506, doi:10.1038/cddis.2014.466 (2014).

22 Leisegang, M. S. et al. Long Noncoding RNA MANTIS Facilitates Endothelial Angiogenic Function. *Circulation*, doi:10.1161/CIRCULATIONAHA.116.026991 (2017).

23 Kurian, L. et al. Identification of novel long noncoding RNAs underlying vertebrate cardiovascular development. *Circulation* 131, 1278-1290, doi:10.1161/CIRCULATIONAHA. 114.013303 (2015).

24 Chao, H. et al. Long Noncoding RNA MEG3 Negatively Regulates Proliferation and Angiogenesis in Vascular Endothelial Cells. *DNA and Cell Biology* 36, 475481, doi:10.1089/dna.2017.3682 (2017).

25 Qiu, G. Z., Tian, W., Fu, H. T., Li, C. P. & Liu, B. Long noncoding RNA-MEG3 is involved in diabetes mellitus-related microvascular dysfunction. *Biochem Biophys Res Commun* 471, 135-141, doi:10.1016/j.bbrc.2016.01.164 (2016).

26 Yan, B. A. et al. lncRNA-MIAT Regulates Microvascular Dysfunction by Functioning as a Competing Endogenous RNA. *Circulation Research* 116, 1143-+, doi:10.1161/Circresaha. 116.305510 (2015).

27 Boulberdaa, M. et al. A Role for the Long Noncoding RNA SENCR in Commitment and Function of Endothelial Cells. *Mol Ther* 24, 978-990, doi:10.1038/mt.2016.41 (2016).

28 Neumann, P. et al. The lncRNA GATA6-AS epigenetically regulates endothelial gene expression via interaction with LOXL2. *Nat Commun* 9, 237, doi:10.1038/s41467-017-02431-1 (2018).

29 Man, H. S. J. et al. Angiogenic patterning by STEEL, an endothelial-enriched long noncoding RNA. *Proc Natl Acad Sci USA*, doi:10.1073/pnas.1715182115 (2018).

30 Orom. U. A. et al. Long noncoding RNAs with enhancer-like function in human cells. *Cell* 143, 46-58, doi:10.1016/j.cell.2010.09.001 (2010).

31 Bell, R. D. et al. Identification and initial functional characterization of a human vascular cell-enriched long noncoding RNA. *Arterioscler Thromb Vasc Biol* 34, 1249-1259, doi:10.1161/ATVBAHA.114.303240 (2014).

32 Diehn, M. et al. SOURCE: a unified genomic resource of functional annotations, ontologies, and gene expression data. *Nucleic Acids Res* 31, 219-223 (2003).

33 Fish, J. E. et al. miR-126 regulates angiogenic signaling and vascular integrity. *Dev Cell* 15, 272-284, doi: 10.1016/j.devcel.2008.07.008 (2008).

34 Wang, S. et al. The endothelial-specific microRNA miR-126 governs vascular integrity and angiogenesis. *Developmental cell* 15, 261-271, doi:10.1016/j.devcel.2008.07.002 (2008).

35 Kuhnert, F. et al. Attribution of vascular phenotypes of the murine Egfl7 locus to the microRNA miR-126. *Development* 135, 3989-3993, doi:10.1242/dev.029736 (2008).

36 Durrans, A. & Stuhlmann, H. A role for Egfl7 during endothelial organization in the embryoid body model system. *J Angiogenes Res* 2, 4, doi:2040-2384-2-4 [pii]10.1186/2040-2384-24 (2010).

37 Parker, L. H. et al. The endothelial-cell-derived secreted factor Egfl7 regulates vascular tube formation. *Nature* 428, 754-758, doi:10.1038/nature02416 (2004).

38 Schmidt, M. et al. EGFL7 regulates the collective migration of endothelial cells by restricting their spatial distribution. *Development* 134, 2913-2923, doi: 10.1242/dev.002576 (2007).

39 Zhang, Q., Chen, C. Y., Yedavalli, V. S. & Jeang, K. T. NEATi long noncoding RNA and paraspeckle bodies modulate HIV-1 posttranscriptional expression. *MBio* 4, e00596-00512, doi:10.1128/mBio.00596-12 (2013).

40 Cabili, M. N. et al. Localization and abundance analysis of human lncRNAs at single-cell and single-molecule resolution. *Genome Biol* 16, 20, doi:10.1186/s13059-015-0586-4 (2015).

41 Antequera, F. Structure, function and evolution of CpG island promoters. *Cell Mol Life Sci* 60, 1647-1658, doi:10.1007/s00018-003-3088-6 (2003).

42 Uesaka, M. et al. Bidirectional promoters are the major source of gene activation-associated non-coding RNAs in mammals. *BMC Genomics* 15, 35, doi:10.1186/1471-2164-15-35 (2014).

43 Harris, T. A., Yamakuchi, M., Kondo, M., Oettgen, P. & Lowenstein, C. J. Ets-1 and Ets-2 regulate the expression of microRNA-126 in endothelial cells. *Arterioscler Thromb Vasc Biol* 30, 1990-1997, doi:10.1161/ATVBAHA.110.211706 (2010).

44 Hetheridge, C., Mavria, G. & Mellor, H. Uses of the in vitro endothelial-fibroblast organotypic co-culture assay in angiogenesis research. *Biochem Soc Trans* 39, 1597-1600, doi:10.1042/BST20110738 (2011).

45 Shao, Z. et al. Choroid sprouting assay: an ex vivo model of microvascular angiogenesis. *PLoS One* 8, e69552, doi:10.1371/journal.pone.0069552 (2013).

46 Bellucci, M., Agostini, F., Masin, M. & Tartaglia, G. G. Predicting protein associations with long noncoding RNAs. *Nat Methods* 8, 444-445, doi:10.1038/nmeth.1611 (2011).

47 Vervoorts, J. et al. Stimulation of c-MYC transcriptional activity and acetylation by recruitment of the cofactor CBP. *EMBO Rep* 4, 484-490, doi:10.1038/sj.embor.embor821 (2003).

48 Mai, S. & Jalava, A. c-Myc binds to 5' flanking sequence motifs of the dihydrofolate reductase gene in cellular extracts: role in proliferation. *Nucleic Acids Res* 22, 2264-2273 (1994).

49 Bouchard, C. et al. Regulation of cyclin D2 gene expression by the Myc/Max/Mad network: Myc-dependent TRRAP recruitment and histone acetylation at the cyclin D2 promoter. *Genes Dev* 15, 2042-2047, doi: 10.1101/gad.907901 (2001).

50 Qi, L. S. et al. Repurposing CRISPR as an RNA-Guided Platform for Sequence-Specific Control of Gene Expression. *Cell* 152, 1173-1183, doi:10.1016/j.cell.2013.02.022 (2013).

51 Derrien, T. et al. The GENCODE v7 catalog of human long noncoding RNAs: Analysis of their gene structure, evolution, and expression. *Genome Research* 22, 1775-1789, doi:10.1101/gr.132159.111 (2012).

52 Nikolic, I., Plate, K. H. & Schmidt, M. H. EGFL7 meets miRNA-126: an angiogenesis alliance. *J Angiogenes Res* 2, 9, doi:10.1186/2040-2384-2-9 (2010).

53 Harris, T. A., Yamakuchi, M., Ferlito, M., Mendell, J. T. & Lowenstein, C. J. MicroRNA-126 regulates endothelial expression of vascular cell adhesion molecule 1. *Proc Natl Acad Sci USA* 105, 1516-1521, doi:10.1073/pnas.0707493105 (2008).

54 Mattes, J., Collison, A., Plank, M., Phipps, S. & Foster, P. S. Antagonism of microRNA-126 suppresses the effector function of TH2 cells and the development of allergic airways disease. *Proc Natl Acad Sci USA* 106, 18704-18709, doi:0905063106 [pii]10.1073/pnas.0905063106 (2009).

55 Agudo, J. et al. The miR-126-VEGFR2 axis controls the innate response to pathogen-associated nucleic acids. *Nat Immunol* 15, 54-62, doi:10.1038/ni.2767 (2014).

56 Zhou, Q. et al. Strand and Cell Type-specific Function of microRNA-126 in Angiogenesis. *Mol Ther* 24, 1823-1835, doi:10.1038/mt.2016.108 (2016).

57 Amati, B. & Land, H. Myc-Max-Mad: a transcription factor network controlling cell cycle progression, differentiation and death. *Curr Opin Genet Dev* 4, 102-108 (1994).

58 Jager, R. D., Mieler, W. F. & Miller, J. W. Age-related macular degeneration. *N Engl J Med* 358, 2606-2617, doi:10.1056/NEJMra0801537 (2008).

59 Folk, J. C. & Stone, E. M. Ranibizunab therapy for neovascular age-related macular degeneration. *N Engl J Med* 363, 1648-1655, doi:10.1056/NEJMct1000495 (2010).

60 Kruger Falk, M., Kemp, H. & Sorensen, T. L. Four-year treatment results of neovascular age-related macular degeneration with ranibizumab and causes for discontinuation of treatment. *Am J Ophthalmol* 155, 89-95 e83, doi:10.1016/j.ajo.2012.06.031 (2013).

61 Skovseth, D. K., Kuchler, A. M. & Haraldsen, G. The HUVEC/Matrigel assay: an in vivo assay of human angiogenesis suitable for drug validation. *Methods Mol Biol* 360, 253-268, doi:10.1385/1-59745-165-7:253 (2007).

62 Zhou, Q. et al. Repression of choroidal neovascularization through actin cytoskeleton pathways by microRNA-24. *Mol Ther* 22, 378-389, doi: 10.1038/mt.2013.243 (2014).

63 Wang, S. et al. Control of endothelial cell proliferation and migration by VEGF signaling to histone deacetylase 7. *Proc Natl Acad Sci USA* 105, 7738-7743, doi:10.1073/pnas.0802857105 (2008).

64 Shao, Z. et al. Choroid sprouting assay: an ex vvo model of microvascular angiogenesis. *PLoS One* 8, e69552, doi:10.1371/journal.pone.0069552 (2013).

65 Wagatsuma, A. et al. Determination of the exact copy numbers of particular mRNAs in a single cell by quantitative real-time RT-PCR. *J Exp Biol* 208, 2389-2398, doi:10.1242/jeb.01625 (2005).

66 Nelson, J. D., Denisenko, O. & Bomsztyk, K. Protocol for the fast chromatin immunoprecipitation (ChIP) method. *Nat Protoc* 1, 179-185, doi:10.1038/nprot.2006.27 (2006).

67 Larson, M. H. et al. CRISPR interference (CRISPRi) for sequence-specific control of gene expression. *Nat Prowc* 8, 2180-2196, doi:10.1038/nprot.2013.132 (2013).

68 Huang, Z. P. et al. Cardiomyocyte-enriched protein CIP protects against pathophysiological stresses and regulates cardiac homeostasis. *J Clin Invest* 125, 4122-4134, doi:10.1172/JC182423 (2015).

What is claimed is:

1. A composition comprising an antagonist of each of lncEGFL7OS, EGFL7, and miR-126 function in a pharmaceutically acceptable buffer, diluent or medium, wherein the antagonist is a single guide RNA (sg-RNA) plus dead Cas9-Krüppel associated box (dCas9-KRAB), wherein said sg-RNA is sg-RNA-1 (SEQ ID NO: 2) or sg-RNA-2 (SEQ ID NO: 3).

2. The composition of claim 1, wherein said antagonist is encoded by an expression vector that is a viral vector.

3. The composition of claim 1, wherein said antagonist is encoded by an expression vector that is a non-viral vector.

* * * * *

SEQUENCE LISTING

```
<160> NUMBER OF SEQ ID NOS: 75

<210> SEQ ID NO 1
<211> LENGTH: 557
<212> TYPE: DNA
<213> ORGANISM: Artificial sequence
<220> FEATURE:
<223> OTHER INFORMATION: Synthetic oligonucleotide

<400> SEQUENCE: 1

tgggctcagg cccagagtgc cagctttgcc ctatcccata gcctggagcc accacaggag     60

gggcactcca ctctcttggg ctcctggagc ctcagaggca gagccagccg ggagtgcagg    120

agggagaact ttcctgtgga cgtcctgtgt tctccagacg cagagaaccc tcatcaaccg    180

agggggaggt cacttccgaa tccacagatg gcgtgtgagt gcatggcgag cgcctccagg    240

acacacttac tgttcccttg ctctggccag acgccagccg gaccctgtgt gtgcgcgccg    300

tgctgctctt tgcagctgcc tgcaaggggt tcctgcgaag accagcacct tggggaagag    360

cctgcggctg aacttgaact cgcagctacc tgagtcagac ctgtgctttt tcacctctac    420

ggaagatgtc agagcgtttc cctagcaatg ttttagaagt tacttctgtc tggaaaaaaa    480

tggaaaaaat ggcaaattat gttatgtata atttgataat tttaaagaat taatgatgta    540

attattactc aaaccca                                                   557


<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2

tgcttacagg caaggggcga                                                 20


<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3

aagaattgct tcagctcgga                                                 20


<210> SEQ ID NO 4
<211> LENGTH: 96
<212> TYPE: DNA
<213> ORGANISM: Artificial sequence
<220> FEATURE:
<223> OTHER INFORMATION: Synthetic oligonucleotide

<400> SEQUENCE: 4

tgcttacagg caaggggcga gttttagagc tagaaatagc aagttaaaat aaggctagtc     60
```

-continued cgttatcaac ttgaaaaagt ggcaccgagt cggtgc 96

<210> SEQ ID NO 5
<211> LENGTH: 96
<212> TYPE: DNA
<213> ORGANISM: Artificial sequence
<220> FEATURE:
<223> OTHER INFORMATION: Synthetic oligonucleotide

<400> SEQUENCE: 5
aagaattgct tcagctcgga gttttagagc tagaaatagc aagttaaaat aaggctagtc 60
cgttatcaac ttgaaaaagt ggcaccgagt cggtgc 96

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
agtgccagct ttgccctatc 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gagaacacag gacgtccaca 20

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
aagggaggct cctgtgga 18

<210> SEQ ID NO 9
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 9
cctgggggct gctgatg 17

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
tggcgtcttc cagaatgc 18

<210> SEQ ID NO 11
<211> LENGTH: 17

<212> TYPE: DNA
<213> ORGANISM: Artificial sequence
<220> FEATURE:
<223> OTHER INFORMATION: Synthetic oligonucleotide

<400> SEQUENCE: 11
tcagccaagg cagaagt 17

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
gcguuucccu agcaauguut t 21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
aacauugcua gggaaacgct t 21

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
cagcuuugcc cuaucccaut t 21

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
augggauagg gcaaagcugt t 21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
ccaguauaug cgaaggaaat t 21

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17

-continued uuuccuucgc auauacuggt t 21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
cacacaccag caagauauut t 21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
aauaucuugc uggugugugt t 21

<210> SEQ ID NO 20
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 20
ccgacgagug auggcacuga att 23

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
uucagugcca ucacucgucg g 21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
cagucauuca ucagcuggat t 21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
uccagcugau gaaugacugt t 21

<210> SEQ ID NO 24
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 24
gccctttggg ctcaggccca ga 22

<210> SEQ ID NO 25
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 25
gccctttggg tttgagtaat aattac 26

<210> SEQ ID NO 26
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 26
aaaagatcta tggcgtgtga gtgcatggcg agc 33

<210> SEQ ID NO 27
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 27
tataagcttt gggtttgagt aataattaca tcat 34

<210> SEQ ID NO 28
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 28
atgcgaattc gagtgaaaga gccccacact g 31

<210> SEQ ID NO 29
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 29
atgcaagctt agtgccagcc gtggtcctta c 31

<210> SEQ ID NO 30
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 30
gagcaagaga tggccacgg 19

-continued

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
actccatgcc caggaaggaa 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
cctgaggcca tcttaccacc 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
aatccgcttc gatgagtggg 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcgcattgtt aggagaaggg 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
cctgctgact gtcctagagg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cgggcagctt acgattcttc 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 37
cggtgtcttt cagagggtct 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ccatgtcgcc tcagcctaaa 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gggcagtctc agggtaacac 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ctcggaaaac ggagggttga 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cgctgccctt aattccttgc 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
accagcagac cctgaaactc 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ggcagggatc aggcattcat 20

<210> SEQ ID NO 44

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
agtgccagct ttgccctatc 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gagaacacag gacgtccaca 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cttcagaggc caaaagcacc 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gaatcagtca tcccccggac 20

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
aagggaggct cctgtgga 18

<210> SEQ ID NO 49
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 49
cctgggggct gctgatg 17

<210> SEQ ID NO 50
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 50
cggatccggc ggcca 15

<210> SEQ ID NO 51
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 51
cgaacgactc ggagacagg 19

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
agatacagtg tgggtggtgg 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
agtcttcccc accttgtagc 20

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
tggcgtcttc cagaatgc 18

<210> SEQ ID NO 55
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 55
tcagccaagg cagaagt 17

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gctgtgcatt tacaccgaca 20

<210> SEQ ID NO 57
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 57
tgcgcaagat gtgctcaatg 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
atttcgcgcc aaacttgacc 20

<210> SEQ ID NO 59
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 59
tctgaattca ttcctgagcg gt 22

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
ctggctgttt tggggctaga 20

<210> SEQ ID NO 61
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 61
cctgtgtgtg ttctccgct 19

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
agatcccagg gctgtttagc 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
aacactcctc ccagcgaatc 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gcagggaacc tagtgtacgg 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cgcgcccttt ggtgtatttc 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
cggggctaca aattgggtga 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
taaaagacgc accccttgcc 20

<210> SEQ ID NO 68
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 68
aatagatctt gggctcaggc ccagagtgcc a 31

<210> SEQ ID NO 69
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 69
aaaaagcttc tggaggcgct cgccatgcac 30

<210> SEQ ID NO 70
<211> LENGTH: 29
<212> TYPE: DNA
<213> ORGANISM: Artificial sequence
<220> FEATURE:

-continued

```
<223> OTHER INFORMATION: Synthetic oligonucleotide

<400> SEQUENCE: 70

aatagatcta tggcgtgtga gtgcatggc                                29


<210> SEQ ID NO 71
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 71

aaaaagcttt caggtagctg cgagttcaag                               30


<210> SEQ ID NO 72
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 72

aatagatcta ctcgcagcta cctgagtcag a                             31


<210> SEQ ID NO 73
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 73

aaaaagcttt gggtttgagt aataattaca tc                            32


<210> SEQ ID NO 74
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 74

atcgctcaga tagactctga tggcccagg                                29


<210> SEQ ID NO 75
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 75

atcgctcaga ccagcttggt gcagggag                                 28
```